(12) United States Patent
Reed et al.

(10) Patent No.: US 12,303,564 B2
(45) Date of Patent: May 20, 2025

(54) COMPOSITE CHITOSAN-TANNIN-ACTIVE AGENT COMPOSITIONS AND METHODS OF MAKING AND USING SAME

(71) Applicant: WISCONSIN ALUMNI RESEARCH FOUNDATION, Madison, WI (US)

(72) Inventors: Jess Reed, Verona, WI (US); Christian Krueger, Cambridge, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/522,334

(22) Filed: Nov. 9, 2021

(65) Prior Publication Data

US 2022/0296720 A1 Sep. 22, 2022

Related U.S. Application Data

(60) Provisional application No. 63/163,322, filed on Mar. 19, 2021.

(51) Int. Cl.
| | |
|---|---|
| *A61K 47/36* | (2006.01) |
| *A61K 9/00* | (2006.01) |
| *A61K 9/70* | (2006.01) |
| *A61K 31/4045* | (2006.01) |
| *A61K 31/661* | (2006.01) |
| *A61K 31/7016* | (2006.01) |
| *A61K 47/22* | (2006.01) |

(52) U.S. Cl.
CPC .............. *A61K 47/36* (2013.01); *A61K 9/006* (2013.01); *A61K 31/4045* (2013.01); *A61K 31/661* (2013.01); *A61K 31/7016* (2013.01); *A61K 47/22* (2013.01); *A61K 9/70* (2013.01)

(58) Field of Classification Search
CPC .... A61K 47/36; A61K 9/006; A61K 31/4045; A61K 31/661; A61K 31/7016; A61K 47/22; A61K 9/70
See application file for complete search history.

(56) References Cited

U.S. PATENT DOCUMENTS

| | | | |
|---|---|---|---|
| 4,090,919 A | 5/1978 | Chibata | |
| 4,559,157 A | 12/1985 | Smith | |
| 4,608,392 A | 8/1986 | Jacquet | |
| 4,820,508 A | 4/1989 | Wortzman | |
| 4,938,949 A | 7/1990 | Borch | |
| 4,992,478 A | 2/1991 | Geria | |
| 5,153,281 A | 10/1992 | Shimizu | |
| 6,020,422 A | 2/2000 | Connors | |
| 6,780,504 B2 | 8/2004 | Rupprecht | |
| 6,960,617 B2 | 11/2005 | Omidian | |
| 7,122,574 B2 | 10/2006 | Romanczyk, Jr. et al. | |
| 7,288,532 B1 | 10/2007 | Payne | |
| 7,482,503 B2 | 1/2009 | Gregory | |
| 7,767,235 B2 | 8/2010 | Shrikhande | |
| 8,642,088 B2 | 2/2014 | Reed | |
| 9,545,423 B2 | 1/2017 | Reed | |
| 10,104,888 B2 | 10/2018 | Reed | |
| 2001/0051189 A1 | 12/2001 | Alonso Fernandez et al. | |
| 2003/0232895 A1 | 12/2003 | Omidian et al. | |
| 2004/0151778 A1 | 8/2004 | Richard et al. | |
| 2005/0049472 A1 | 3/2005 | Manda et al. | |
| 2005/0147656 A1 | 7/2005 | McCarthy et al. | |
| 2005/0150489 A1 | 7/2005 | Dunfield et al. | |
| 2005/0281886 A1 | 12/2005 | Cattaneo | |
| 2007/0066924 A1 | 3/2007 | Hopman et al. | |
| 2007/0071871 A1 | 3/2007 | Shrikhande et al. | |
| 2007/0196401 A1 | 8/2007 | Naruse | |
| 2007/0292539 A1 | 12/2007 | Vorsa et al. | |
| 2008/0069779 A1* | 3/2008 | Tamarkin ............... | A61K 8/498 424/45 |
| 2008/0095810 A1 | 4/2008 | Alonso Fernandez et al. | |
| 2008/0286254 A1 | 11/2008 | Sakamoto et al. | |
| 2009/0035440 A1 | 2/2009 | Velikov | |
| 2009/0143331 A1* | 6/2009 | Stroumpoulis ......... | A61K 8/678 514/59 |
| 2011/0059162 A1* | 3/2011 | Reed ..................... | A61L 29/085 424/488 |
| 2011/0250812 A1 | 10/2011 | Pourdeyhimi et al. | |
| 2011/0274726 A1 | 11/2011 | Guo et al. | |
| 2013/0291878 A1 | 11/2013 | Takayama | |
| 2015/0335593 A1* | 11/2015 | Zolotarsky ........... | A61K 9/2031 514/654 |
| 2019/0046688 A1 | 2/2019 | Miller et al. | |
| 2020/0056057 A1 | 2/2020 | Nagarajan et al. | |

FOREIGN PATENT DOCUMENTS

| | | |
|---|---|---|
| CN | 109395170 A1 | 3/2019 |
| CZ | 3066691 B6 | 5/2017 |
| DE | 4141889 A1 | 6/1993 |

(Continued)

OTHER PUBLICATIONS

Garlea et al., Chitosan-Polyphenols Nanostructured Matrices Drug Release Kinetics Studies, Analele Stiintifice ale Universitatii "Al. I. Cuza" din Iași (Serie Noua), Tomul IV, Biofizica, Fizica Medicala, Fizica Mediului, (2008), pp. 25-30, ISSN 1841-5318.

Choi, J.S., Lee, S.W., Jeong, L., Bae, S.H., Min, B.C., Youk, J.H., & Park, W.H. (2004). Effect of organosoluble salts on the nanofibrous structure of electrospun poly(3-hydroxybutyrate-co-3-hydroxyvalerate). *International Journal of Biological Macromolecules*, 34, 249.

Mogoşanu, G. D., & Grumezescu, A. M. (2014). Natural and synthetic polymers for wounds and burns dressing. *International journal of pharmaceutics*, 463(2), 127-136.

Varoni, E. M., Iriti, M., & Rimondini, L. (2012). Plant products for innovative biomaterials in dentistry. *Coatings*, 2(3), 179-194.

(Continued)

Primary Examiner — Robert A Wax
Assistant Examiner — Olga V. Tcherkasskaya
(74) Attorney, Agent, or Firm — Daniel A. Blasiole; DeWitt LLP

(57) ABSTRACT

Composite composition comprising chitosan, tannin, and an active agent and methods of making and using same.

20 Claims, 35 Drawing Sheets

(56) References Cited

FOREIGN PATENT DOCUMENTS

| | | |
|---|---|---|
| EP | 507272 A1 | 10/1992 |
| EP | 1304346 A2 | 4/2003 |
| JP | 4308525 A | 10/1992 |
| JP | 7236419 A | 9/1995 |
| JP | 11057314 A | 3/1999 |
| JP | 2001335698 A | 12/2001 |
| JP | 2004026785 A | 1/2004 |
| KR | 101309546 B1 | 9/2013 |
| WO | WO 1999/004764 A1 | 2/1999 |
| WO | WO 2003/091237 A1 | 11/2003 |
| WO | WO 2010/078660 A1 | 7/2010 |
| WO | WO 2011/129230 A1 | 10/2011 |

OTHER PUBLICATIONS

Aadil, K. R., Mussatto, S. I., & Jha, H. (2018). Synthesis and characterization of silver nanoparticles loaded poly (vinyl alcohol)-lignin ESNFs and their antimicrobial activity. *International journal of biological macromolecules*, 120, 763-767.

Abdel-Hady, F., Alzahrany, A., & Hamed, M. (2011). Experimental validation of upward electrospinning process. *ISRN nanotechnology*, 2011, pp. 1-14.

Agarwal, S., Wendorff, J. H., & Greiner, A. (2008). Use of electrospinning technique for biomedical applications. *Polymer*, 49(26), 5603-5621.

Al-Omair, M. (2015). Synthesis of antibacterial silver-poly (ε-caprolactone)-methacrylic acid graft copolymer nanofibers and their evaluation as potential wound dressing. *Polymers*, 7(8), 1464-1475.

Alborzi, S., Lim, L. T., & Kakuda, Y. (2014). Release of folic acid from sodium alginatepectin-poly (ethylene oxide) electrospun fibers under in vitro conditions. *LWT-FoodScience and Technology*, 59(1), 383-388.

Angammana, C. J., & Jayaram, S. H. (2011). Analysis of the effects of solution conductivity on electrospinning process and fiber morphology. *IEEE Transactions on industry applications*, 47(3), 1109-1117.

Arce-Urbina, M. E., Hun-Opfer, C., & Mata-Segreda, J. F. (2003). The aqueous extract of Triumfetta semitriloba (Tiliaceae) does not inhibit the in-vitro hydrolytic activity of the major pancreatic enzymes. *Revista de biología tropical*, 51(2), 313-316.

Avila, G., Misch, K., Galindo-Moreno, P., & Wang, H. L. (2009). Implant surface treatment using biomimetic agents. *Implant dentistry*, 18(1), 17-26.

Bauer, A. W., Kirby, W. M. M., Sherris, J. C., & Turck, M. (1966). Antibiotic susceptibility testing by a standardized single disk method. *American journal of clinical pathology*, 45(4_ts), 493-496.

Beecher, Overview of dietary flavonoids: nomenclature, occurrence and intake, J. Nutrition, 2003, 3248S-3254S.

Bhardwaj, N., & Kundu, S. C. (2010). Electrospinning: a fascinating fiber fabrication technique. *Biotechnology advances*, 28(3), 325-347.

Bhattarai, D., Aguilar, L., Park, C., & Kim, C. (2018). A review on properties of natural and synthetic based electrospun fibrous materials for bone tissue engineering. *Membranes*, 8(3), 62.

Blainski, A., Lopes, G., & de Mello, J. (2013). Application and analysis of the folin ciocalteu method for the determination of the total phenolic content from Limonium brasiliense L. *Molecules*, 18(6), 6852-6865.

Blumberg, J. B., Basu, A., Krueger, C. G., Lila, M. A., Neto, C. C., Novotny, J. A., . . . & Toner, C. D. (2016). Impact of cranberries on gut microbiota and cardiometabolic health: Proceedings of the cranberry health research conference 2015. *Advances in Nutrition*, 7(4), 759S-770S.

Bondet, V., Brand-Williams, W., & Berset, C. L. W. T. (1997). Kinetics and mechanisms of antioxidant activity using the DPPH. free radical method. *LWT-Food Science and Technology*, 30(6), 609-615.

Brettmann, B. K., Tsang, S., Forward, K. M., Rutledge, G. C., Myerson, A. S., & Trout, B. L. (2012). Free surface electrospinning of fibers containing microparticles. *Langmuir*, 28(25), 9714-9721.

Brettmann, B. K., Cheng, K., Myerson, A. S., & Trout, B. L. (2013) Electrospun formulations containing crystalline active pharmaceutical ingredients. *Pharmaceutical research*, 30(1), 238-246.

Brettmann, B., Pincus, P., & Tirrell, M. (2017). Lateral structure formation in polyelectrolyte brushes induced by multivalent ions. *Macromolecules*, 50(3), 1225-1235.

Bustamante, M., Oomah, B. D., Rubilar, M., & Shene, C. (2017). Effective Lactobacillus plantarum and Bifidobacterium infantis encapsulation with chia seed (Salvia hispanica L.) and flaxseed (Linum usitatissimum L.) mucilage and soluble protein by spray drying. *Food chemistry*, 216, 97-105.

Charernsriwilaiwat, N., Rojanarata, T., Ngawhirunpat, T., Sukma, M., & Opanasopit, P. (2013). Electrospun chitosan-based nanofiber mats loaded with Garcinia mangostana extracts. *International journal of pharmaceutics*, 452(1-2), 333-343.

Chaves, M. A., Piati, J., Malacarne, L. T., Gall, R. E., Colla, E., Bittencourt, P. R., . . . & Matsushita, M. (2018). Extraction and application of chia mucilage (Salvia hispanica L.) and locust bean gum (Ceratonia siliqua L.) in goat milk frozen dessert. *Journal of food science and technology*, 55(10), 4148-4158.

Choi, U.S., Lee, S.W., Jeong, L., Bae, S.H., Min, B.C., Youk, J.H., & Park, W.H. (2004). Effect of organosoluble salts on the nanofibrous structure of electrospun poly(3-hydroxybutyrate-co-3-hydroxyvalerate). *International Journal of Biological Macromolecules*, 34, 249.

Deitzel, J. M., Kleinmeyer, J., Harris, D. E. A., & Tan, N. B. (2001). The effect of processing variables on the morphology of ESNFs and textiles. *Polymer*, 42(1), 261-272.

Dhandayuthapani, B., Yoshida, Y., Maekawa, T., & Kumar, D. S. (2011). Polymeric scaffolds in tissue engineering application: a review. *International journal of polymerscience*, 2011, pp. 1-19.

Du, L., Xu, H., Zhang, Y., & Zou, F. (2016). Electrospinning of polycaprolatone nanofibers with DMF additive: the effect of solution proprieties on jet perturbation and fiber morphologies. *Fibers and Polymers*, 17(5), 751-759.

Duan, B., Dong, C., Yuan, X., & Yao, K. (2004). Electrospinning of chitosan solutions in acetic acid with poly (ethylene oxide). *Journal of Biomaterials Science, Polymer Edition*, 15(6), 797-811.

Eichhorn, S. J., & Sampson, W. W. (2010). Relationships between specific surface area and pore size in electrospun polymer fibre networks. *Journal of the Royal Society Interface*, 7(45), 641-649.

Elendran, S., Wang, L. W., Prankerd, R., & Palanisamy, U. D. (2015). The physicochemical properties of geraniin, a potential antihyperglycemic agent. *Pharmaceutical biology*, 53(12), 1719-1726.

Ewaldz, E., & Brettmann, B. (2019). Molecular Interactions in Electrospinning: From Polymer Mixtures to Supramolecular Assemblies. *ACS Applied Polymer Materials*, 1(3), 298-308.

Ewaldz, E., Patel, R., Banerjee, M., & Brettmann, B. K. (2018). Material selection in electrospinning microparticles. *Polymer*, 153, 529-537.

Fallahi, D., Rafizadeh, M., Mohammadi, N., & Vahidi, B. (2008). Effect of applied voltage on jet electric current and flow rate in electrospinning of polyacrylonitrile solutions. *Polymer international*, 57(12), 1363-1368.

Fang, Z., & Bhandari, B. (2010). Encapsulation of polyphenols—a review. *Trends in Food Science & Technology*, 21(10), 510-523.

Feldman, M., Tanabe, S., Howell, A., & Grenier, D. (2012). Cranberry proanthocyanidins inhibit the adherence properties of Candida albicans and cytokine secretion by oral epithelial cells. *BMC complementary and alternative medicine*, 12(1), 6.

Feliciano, R. P., Krueger, C. G., & Reed, J. D. (2015). Methods to determine effects of cranberry proanthocyanidins on extraintestinal infections: Relevance for urinary tract health. *Molecular nutrition & food research*, 59(7), 1292-1306.

Feliciano, R. P., Shea, M. P., Shanmuganayagam, D., Krueger, C. G., Howell, A. B., & Reed, J. D. (2012). Comparison of isolated cranberry (Vaccinium macrocarpon Ait.) proanthocyanidins to catechin and procyanidins A2 and B2 for use as standards in the 4-(dimethylamino) cinnamaldehyde assay. *Journal of agricultural and food chemistry*, 60(18), 4578-4585.

(56) References Cited

OTHER PUBLICATIONS

Fernandez, A., Torres-Giner, S., & Lagaron, J. M. (2009). Novel route to stabilization of bioactive antioxidants by encapsulation in electrospun fibers of zein prolamine. *Food Hydrocolloids*, 23(5), 1427-19721.

Ferreira, J. L., Gomes, S., Henriques, C., Borges, J. P., & Silva, J. C. (2014). Electrospinning polycaprolactone dissolved in glacial acetic acid: Fiber production, nonwoven characterization, and in Vitro evaluation. *Journal of Applied Polymer Science*, 131(22).

Frenot, A., & Chronakis, I. S. (2003). Polymer nanofibers assembled by electrospinning. *Current opinion in colloid & interface science*, 8(1), 64-75.

Guo, H. F., & Xu, B. G. (2017). Numerical study of Taylor cone dynamics in electrospinning of nanofibers. In *Key Engineering Materials* (vol. 730, pp. 510-515). Trans Tech Publications.

Gupta, K., Chou, M. Y., Howell, A., Wobbe, C., Grady, R., & Stapleton, A. E. (2007). Cranberry products inhibit adherence of p-fimbriated *Escherichia coli* to primary cultured bladder and vaginal epithelial cells. *The Journal of urology*, 177(6), 2357-2360.

Gurlek, A. C., Sevinc, B., Bayrak, E., & Erisken, C. (2017). Synthesis and characterization of polycaprolactone for anterior cruciate ligament regeneration. *Materials Science and Engineering: C*, 71, 820-826.

Hadad, S., & Goli, S. A. H. (2018). Fabrication and characterization of ESNFs using flaxseed (Linum usitatissimum) mucilage. *International journal of biological macromolecules*, 114, 408-414.

Haeri, M., & Haeri, M. (2015). ImageJ plugin for analysis of porous scaffolds used in tissue engineering. *Journal of Open Research Software*, 3(1).

Haider, A., Haider, S., & Kang, I. K. (2018). A comprehensive review summarizing the effect of electrospinning parameters and potential applications of nanofibers in biomedical and biotechnology. *Arabian Journal of Chemistry*, 11(8), 1165-1188.

Haider, S., Al-Zeghayer, Y., Ali, F. A. A., Haider, A., Mahmood, A., Al-Masry, W. A., . . . & Aijaz, M. O. (2013). Highly aligned narrow diameter chitosan ESNFs. *Journal of Polymer Research*, 20(4), 105.

Hani, N. M., Torkamani, A. E., Azarian, M. H., Mahmood, K. W., & Ngalim, S. H. (2017). Characterisation of electrospun gelatine nanofibres encapsulated with Moringa oleifera bioactive extract. *Journal of the Science of Food and Agriculture*, 97(10), 3348-3358.

Hotaling, N. A., Bharti, K., Kriel, H., & Simon Jr, C. G. (2015). DiameterJ: A validated open source nanofiber diameter measurement tool. *Biomaterials*, 61, 327-338.

Howell, A. B. (2007). Bioactive compounds in cranberries and their role in prevention of urinary tract infections. *Molecular nutrition & food research*, 51(6), 732-737.

Howell, A. B., Reed, J. D., Krueger, C. G., Winterbottom, R., Cunningham, D. G., & Leahy, M. (2005). A-type cranberry proanthocyanidins and uropathogenic bacterial antiadhesion activity. *Phytochemistry*, 66(18), 2281-2291.

Huan, S., Liu, G., Han, G., Cheng, W., Fu, Z., Wu, Q., & Wang, Q. (2015). Effect of experimental parameters on morphological, mechanical and hydrophobic properties of electrospun polystyrene fibers. *Materials*, 8(5), 2718-2734.

Huang, C. H., Chi, C. Y., Chen, Y. S., Chen, K. Y., Chen, P. L., & Yao, C. H. (2012). Evaluation of proanthocyanidin-crosslinked electrospun gelatin nanofibers for drug delivering system. *Materials Science and Engineering: C*, 32(8), 2476-2483.

Ikada, Y. (2006). Challenges in tissue engineering. *Journal of the Royal Society Interface*, 3(10), 589-601.

Jahangir, M. A., Rumi, T. M., Wahab, M. A., Khan, M. I., Rahman, M. A., & Sayed, Z. B. (2017). Poly Lactic Acid (PLA) Fibres: Different Solvent Systems and Their Effect on Fibre Morphology and Diameter. *American Journal of Chemistry*, 7(6), 177-186.

Jahani, H., Kaviani, S., Hassanpour-Ezatti, M., Soleimani, M., Kaviani, Z., & Zonoubi, Z. (2012). The effect of aligned and random electrospun fibrous scaffolds on rat mesenchymal stem cell proliferation. *Cell Journal (Yakhteh)*, 14(1), 31.

Kai, D., Jiang, S., Low, Z. W., & Loh, X. J. (2015). Engineering highly stretchable ligninbased ESNFs for potential biomedical applications. *Journal of Materials Chemistry B*, 3(30), 6194-6204.

Kandhasamy, S., Perumal, S., Madhan, B., Umamaheswari, N., Banday, J. A., Perumal, P.T., & Santhanakrishnan, V. P. (2017). Synthesis and fabrication of collagen-coated ostholamide electrospun nanofiber scaffold for wound healing. *ACS applied materials & interfaces*, 9(10), 8556-8568.

Katsogiannis, K. A. G., Vladisavljević, G. T., & Georgiadou, S. (2015). Porous electrospun polycaprolactone (PCL) fibres by phase separation. *European Polymer Journal*, 69, 284-295.

Kaur, M., Kaur, R., & Punia, S. (2018). Characterization of mucilages extracted from different flaxseed (Linum usitatissiumum L.) cultivars: A heteropolysaccharide with desirable functional and rheological properties. *International journal of biological macromolecules*, 117, 919-927.

Kayaci, F., & Uyar, T. (2012). Encapsulation of vanillin/ cyclodextrin inclusion complex in electrospun polyvinyl alcohol (PVA) nanowebs: Prolonged shelf-life and high temperature stability of vanillin. *Food chemistry*, 133(3), 641-649.

Keat, C.L., Aziz, A., Eid, A.M., & Elmarzugi, N.A. (2015). Biosynthesis of nanoparticles and silver nanoparticles. *Bioresources and Bioprocessing*, 2, 47.

Khajavi, R., & Abbasipour, M. (2012). Electrospinning as a versatile method for fabricating coreshell, hollow and porous nanofibers. *Scientia Iranica*, 19(6), 2029-2034.

Khoo, H.E., Azlan, A., Tang, S.T., & Lim, S.M. (2017). Anthocyanidins and anthocyanins: colored pigments as food, pharmaceutical ingredients, and the potential health benefits. *Food and Nutrition Research*, 61(1), 1361779.

Kim, H. C., Kim, M. H., & Park, W. H. (2018). Polyelectrolyte complex nanofibers from poly (γ-glutamic acid) and fluorescent chitosan oligomer. *International journal of biological macromolecules*, 118, 238-243.

Krishnan, P. (2006). The scientific study of herbal wound healing therapies: Current state of play. *Current Anaesthesia & Critical Care*, 17(1-2), 21-27.

Krueger et al. Matrix-assisted laser desorption/ionization time-of-flight mass spectrometry of heteropolyflavan-3-ols and glucosylated heteropolyflavans in sorghum [Sorghum bicolor (L.) Moench], J. Agric. Food Chem. 2003, 51, 538-543.

Kumar, A., Paul, S., Kumari, P., Somasundaram, S. T., & Kathiresan, K. (2015). Antioxidant and free radical scavenging activities of Ipomoea pes-caprae (L.) R. Br. extracts. *Int J Curr Pharm Rev Res*, 5, 91-109.

Kurd, F., Fathi, M., & Shekarchizadeh, H. (2017). Basil seed mucilage as a new source for electrospinning: Production and physicochemical characterization. *International journal of biological macromolecules*, 95, 689-695.

Lee, K. Y., Jeong, L., Kang, Y. O., Lee, S. J., & Park, W. H. (2009). Electrospinning of polysaccharides for regenerative medicine. *Advanced drug delivery reviews*, 61(12), 1020-1032.

Li, D., & Xia, Y. (2004). Electrospinning of nanofibers: reinventing the wheel ?. *Advanced materials*, 16(14), 1151-1170.

Li, D., McCann, J. T., Xia, Y., & Marquez, M. (2006). Electrospinning: a simple and versatile technique for producing ceramic nanofibers and nanotubes. *Journal of the American Ceramic Society*, 89(6), 1861-1869.

Li, M., Mondrinos, M. J., Gandhi, M. R., Ko, F. K., Weiss, A. S., & Lelkes, P. I. (2005). Electrospun protein fibers as matrices for tissue engineering. *Biomaterials*, 26(30), 5999-6008.

Li, W. R., Xie, X. B., Shi, Q. S., Zeng, H. Y., You-Sheng, O. Y., & Chen, Y. B. (2010). Antibacterial activity and mechanism of silver nanoparticles on *Escherichia coli*. *Applied microbiology and biotechnology*, 85(4), 1115-1122.

Madrigal-Carballo, S., Haas, L., Vestling, M., Krueger, C. G., & Reed, J. D. (2016). Noncovalent pomegranate (Punica granatum) hydrolyzable tannin-protein complexes modulate antigen uptake, processing and presentation by a T-cell hybridoma line cocultured with murine peritoneal macrophages. *International journal of food sciences and nutrition*, 67(8), 960-968.

(56) References Cited

OTHER PUBLICATIONS

Malafaya, P. B., Silva, G. A., & Reis, R. L. (2007). Natural-origin polymers as carriers and scaffolds for biomolecules and cell delivery in tissue engineering applications. *Advanced drug delivery reviews*, 59(4-5), 207-233.
Malikmammadov, E., Tanir, T. E., Kiziltay, A., Hasirci, V., & Hasirci, N. (2018). PCL and PCL-based materials in biomedical applications. *Journal of Biomaterials science, Polymer edition*, 29(7-9), 863-893.
Maran, J. P., Manikandan, S., Nivetha, C. V., & Dinesh, R. (2017). Ultrasound assisted extraction of bioactive compounds from Nephelium lappaceum L. fruit peel using central composite face centered response surface design. *Arabian Journal of Chemistry*, 10, S1145-S1157.
Matabola, K. P., & Moutloali, R. M. (2013). The influence of electrospinning parameters on the morphology and diameter of poly (vinyledene fluoride) nanofibers-effect of sodium chloride. *Journal of Materials Science*, 48(16), 5475-5482.
Matthews, J. A., Wnek, G. E., Simpson, D. G., & Bowlin, G. L. (2002). Electrospinning of collagen nanofibers. *Biomacromolecules*, 3(2), 232-238.
Megelski, S., Stephens, J. S., Chase, D. B., & Rabolt, J. F. (2002). Micro- and nanostructured surface morphology on electrospun polymer fibers. *Macromolecules*, 35(22), 8456-8466.
Merrill, E. W. (1994). Poly (ethylene oxide) star molecules: synthesis, characterization, and applications in medicine and biology. *Journal of Biomaterials Science, Polymer Edition*, 5(1-2), 1-11.
Miser-Salihoglu, E., Akaydin, G., Caliskan-Can, E., & Yardim-Akaydin, S. (2013). Evaluation of antioxidant activity of various plant-based folk medicines. *Nutrition & Food Sciences*.
Mogoanu, G. D., & Grumezescu, A. M. (2014). Natural and synthetic polymers for wounds and burns dressing. *International journal of pharmaceutics*, 463(2), 127-136.
Moomand, K., & Lim, L. T. (2015). Properties of encapsulated fish oil in electrospun zein fibres under simulated in vitro conditions. *Food and bioprocess technology*, 8(2), 431-444.
Moradkhannejhad, L., Abdouss, M., Nikfarjam, N., Mazinani, S., & Sayar, P. (2017). Electrospun curcumin loaded poly (lactic acid) nanofiber mat on the flexible crosslinked PVA/PEG membrane film: Characterization and in vitro release kinetic study. *Fibers and Polymers*, 18(12), 2349-2360.
Mueller, M., Čavarkapa, A., Unger, F. M., Viernstein, H., & Praznik, W. (2017). Prebiotic potential of neutral oligo-and polysaccharides from seed mucilage of Hyptis suaveolens. *Food chemistry*, 221, 508-514.
Mulfinger, L., Solomon, S. D., Bahadory, M., Jeyarajasingam, A. V., Rutkowsky, S. A., & Boritz, C. (2007). Synthesis and study of silver nanoparticles. *Journal of chemical education*, 84(2), 322.
Munir, A., & Edwards-Lévy, F. (2011). Encapsulation of natural polyphenolic compounds; a review. *Pharmaceutics*, 3(4), 793-829.
Nagori, B. P., & Solanki, R. (2011). Role of medicinal plants in wound healing. *Research Journal of Medicinal Plant*, 5(4), 392-405.
Natarajan, V., Krithica, N., Madhan, B., & Sehgal, P.K. (2010). Formulation and evaluation of quercetin polycaprolactone microspheres for the treatment of rheumatoid arthritis. *Journal of Pharmaceutical Sciences*, 100(1), 195-205.
Nie, H., He, A., Wu, W., Zheng, J., Xu, S., Li, J., & Han, C. C. (2009). Effect of poly (ethylene oxide) with different molecular weights on the electrospinnability of sodium alginate. *Polymer*, 50(20), 4926-4934.
Noriega, S. E., Hasanova, G. I., Schneider, M. J., Larsen, G. F., & Subramanian, A. (2012). Effect of fiber diameter on the spreading, proliferation and differentiation of 81 chondrocytes on electrospun chitosan matrices. *Cells Tissues Organs*, 195(3), 207-221.
Noruzi, M. (2016). Electrospun nanofibres in agriculture and the food industry: a review. *Journal of the Science of Food and Agriculture*, 96(14), 4663-4678.
Okoro, I. O., Osagie, A., & Asibor, E. O. (2010). Antioxidant and antimicrobial activities of polyphenols from ethnomedicinal plants of Nigeria. *African Journal of Biotechnology*, 9(20).
Okuda, T., & Ito, H. (2011). Tannins of constant structure in medicinal and food plants—hydrolyzable tannins and polyphenols related to tannins. *Molecules*, 16(3), 2191-2217.
Okutan, N., Terzi, P., & Altay, F. (2014). Affecting parameters on electrospinning process and characterization of electrospun gelatin nanofibers. *Food Hydrocolloids*, 39, 19-26.
Oveissi, V., Ram, M., Bahramsoltani, R., Ebrahimi, F., Rahimi, R., Naseri, R., . . . & Farzaei, M. H. (2019). Medicinal plants and their isolated phytochemicals for the management of chemotherapy-induced neuropathy: Therapeutic targets and clinical perspective. *DARU Journal of Pharmaceutical Sciences*, 389-406.
Palanisamy, U. D., Ling, L. T., Manaharan, T., & Appleton, D. (2011). Rapid isolation of geraniin from Nephelium lappaceum rind waste and its anti-hyperglycemic activity. *Food Chemistry*, 127(1), 21-27.
Pan, H., Fan, D., Cao, W., Zhu, C., Duan, Z., Fu, R., . . . & Ma, X. (2017). Preparation and characterization of breathable hemostatic hydrogel dressings and determination of their effects on full-thickness defects. *Polymers*, 9(12), 727.
Pan, H., Li, L., Hu, L., & Cui, X. (2006). Continuous aligned polymer fibers produced by a modified electrospinning method. *Polymer*, 47(14), 4901-4904.
Park, J. C., Ito, T., Kim, K. O., Kim, K. W., Kim, B. S., Khil, M. S., . . . & Kim, I. S. (2010). Electrospun poly (vinyl alcohol) nanofibers: effects of degree of hydrolysis and enhanced water stability. *Polymer journal*, 42(3), 273.
Pathak, D., Pathak, K., & Singla, A. K. (1991). Flavonoids as medicinal agents-recent advances. *Fitoterapia*, 62(5), 371-389.
Pelipenko, J., Kristl, J., Janković, B., Baumgartner, S., & Kocbek, P. (2013). The impact of relative humidity during electrospinning on the morphology and mechanical properties of nanofibers. *International journal of pharmaceutics*, 456(1), 125-134.
Picciani, P. H., Medeiros, E. S., Pan, Z., Orts, W. J., Mattoso, L. H., & Soares, B. G. (2009). Development of conducting polyaniline/poly (lactic acid) nanofibers by electrospinning. *Journal of Applied Polymer Science*, 112(2), 744-753.
Pietta, P., Minoggio, M., & Bramati, L. (2003). Plant polyphenols: Structure, occurrence and bioactivity. In *Studies in Natural Products Chemistry* (vol. 28, pp. 257-312). Elsevier.
Pillay, V., Dott, C., Choonara, Y. E., Tyagi, C., Tomar, L., Kumar, P., . . . & Ndesendo, V. M. (2013). A review of the effect of processing variables on the fabrication of ESNFs for drug delivery applications. *Journal of Nanomaterials*, 2013, pp. 1-22.
Quideau and Feldman, Ellagitannin Chemistry, Chem. Rev. 1996, 96, 475-503.
Radzig, M. A., Nadtochenko, V. A., Koksharova, O. A., Kiwi, J., Lipasova, V. A., & Khmel, I. A. (2013). Antibacterial effects of silver nanoparticles on gram-negative bacteria: influence on the growth and biofilms formation, mechanisms of action. *Colloids and Surfaces B: Biointerfaces*, 102, 300-306.
Raghavamma, S.T.V., Mothukuri, A.S., Rama, R.N. (2013). Antimicrobial activity of mucilage isolated from Coccinia grandis (L) Fruits, J Voigt, International Journal of Advances in Pharmaceutical Research 4(11) 2497-2502.
Raven, P. H., Evert, R. F., & Eichhorn, S. E. (2005). *Biology of plants*. Macmillan.
Reed et al. MALDI-TOF mass spectrometry of oligomeric food polyphenols, Phytochem. 66(18): 2248-2263 (2005).
Reyes, C. D., Petrie, T. A., Burns, K. L., Schwartz, Z., & García, A. J. (2007). Biomolecular surface coating to enhance orthopaedic tissue healing and integration. *Biomaterials*, 28(21), 3228-3235.
Rieger, K. A., Birch, N. P., & Schiffman, J. D. (2016). Electrospinning chitosan/poly (ethylene oxide) solutions with essential oils: Correlating solution rheology to nanofiber formation. *Carbohydrate polymers*, 139, 131-138.
Sahay, R., Thavasi, V., & Ramakrishna, S. (2011). Design modifications in electrospinning setup for advanced applications. *Journal of Nanomaterials*, 2011, 17.
Santos, C., Silva, C. J., Büttel, Z., Guimarães, R., Pereira, S. B., Tamagnini, P., & Zille, A. (2014). Preparation and characterization

(56) References Cited

OTHER PUBLICATIONS of polysaccharides/PVA blend nanofibrous membranes by electrospinning method. *Carbohydrate polymers*, 99, 584-592.

Sarhan, W. A., & Azzazy, H. M. (2015). High concentration honey chitosan ESNFs: Biocompatibility and antibacterial effects. *Carbohydrate polymers*, 122, 135-143.

Sell, S. A., Wolfe, P. S., Garg, K., McCool, J. M., Rodriguez, I. A., & Bowlin, G. L. (2010). The use of natural polymers in tissue engineering: a focus on electrospun extracellular matrix analogues. *Polymers*, 2(4), 522-553.

Shao, C., Kim, H. Y., Gong, J., Ding, B., Lee, D. R., & Park, S. J. (2003). Fiber mats of poly (vinyl alcohol)/silica composite via electrospinning. *Materials Letters*, 57(9-10), 1579-1584.

Shenoy, S.L., Bates, W.D., Frisch, H.L., & Wnek, G.E. (2005). Role of chain entanglements on fiber formation during electrospinning of polymer solutions: good solvent, nonspecific polymer-polymer interaction limit. *Polymer*, 46, 3372.

Sill, T. J., & von Recum, H. A. (2008). Electrospinning: applications in drug delivery and tissue engineering. *Biomaterials*, 29(13), 1989-2006.

Singleton, V. L., Orthofer, R., & Lamuela-Raventós, R. M. (1999). Analysis of total phenols and other oxidation substrates and antioxidants by means of folin-ciocalteu reagent. In *Methods in enzymology* (vol. 299, pp. 152-178). Academic press.

Son, W. K., Youk, J. H., Lee, T. S., & Park, W. H. (2005). Effect of pH on electrospinning of poly (vinyl alcohol). *Materials letters*, 59(12), 1571-1575.

Sousa, A. M., Souza, H. K., Uknalis, J., Liu, S. C., Goncalves, M. P., & Liu, L. (2015). Electrospinning of agar/PVA aqueous solutions and its relation with rheological properties. *Carbohydrate polymers*, 115, 348-355.

Subbiah, T., Bhat, G. S., Tock, R. W., Parameswaran, S., & Ramkumar, S. S. (2005). Electrospinning of nanofibers. *Journal of applied polymer science*, 96(2), 557-569.

Sun, Z., Zussman, E., Yarin, A. L., Wendorff, J. H., & Greiner, A. (2003). Compound core-shell polymer nanofibers by co-electrospinning. *Advanced materials*, 15(22), 1929-1932.

Supaphol, P., & Chuangchote, S. (2008). On the electrospinning of poly (vinyl alcohol) nanofiber mats: a revisit. *Journal of Applied Polymer Science*, 108(2), 969-978.

Tang, C., Saquing, C. D., Harding, J. R., & Khan, S. A. (2009). In situ cross-linking of electrospun poly (vinyl alcohol) nanofibers. *Macromolecules*, 43(2), 630-637.

Tarus, B., Fadel, N., Al-Oufy, A., & El-Messiry, M. (2016). Effect of polymer concentration on the morphology and mechanical characteristics of electrospun cellulose acetate and poly (vinyl chloride) nanofiber mats. *Alexandria Engineering Journal*, 55(3), 2975-2984.

Thilagavathi, G., & Bala, S. K. (2007). Microencapsulation of herbal extracts for microbial resistance in healthcare textiles, Indian Journal of Fibre & Textile Research, vol. 32, 2007, p. 351-354.

Thitilertdecha, N., Teerawutgulrag, A., & Rakariyatham, N. (2008). Antioxidant and antibacterial activities of Nephelium lappaceum L. extracts. *LWT-Food Science and Technology*, 41(10), 2029-2035.

Tsai, S. P., Hsieh, C. Y., Hsieh, C. Y., Chang, Y. N., Wang, D. M., & Hsieh, H. J. (2007). Gamma-poly (glutamic acid)/chitosan composite scaffolds for tissue engineering applications. In *Materials science forum* (vol. 539, pp. 567-572). Trans Tech Publications.

Ulrey, R. K., Barksdale, S. M., Zhou, W., & van Hoek, M. L. (2014). Cranberry proanthocyanidins have anti-biofilm properties against Pseudomonas aeruginosa. *BMC complementary and alternative medicine*, 14(1), 499.

Urena-Saborio, H., Alfaro-Viquez, E., Esquivel-Alvarado, D., Madrigal-Carballo, S., & Gunasekaran, S. (2018). Electrospun plant mucilage nanofibers as biocompatible scaffolds for cell proliferation. *International journal of biological macromolecules*, 115, 1218-1224.

Van der Schueren, L., De Schoenmaker, B., Kalaoglu, Ö. I., & De Clerck, K. (2011). An alternative solvent system for the steady state electrospinning of polycaprolactone. *European Polymer Journal*, 47(6), 1256-1263.

Vanaja, M., Gnanajobitha, G., Paulkumar, K., Rajeshkumar, S., Malarkodi, C., & Annadura, G. (2013). Phytosynthesis of silver nanoparticles by *Cissus quadrangularis*: Influence of physicochemical factors. *Journal of Nanostructure in Chemistry*, 3, 17.

Varoni, E. M., Iriti, M., & Rimondini, L. (2012). Plant products for innovative biomaterials in dentistry. *Coatings9*, 2(3), 179-194.

Vineis, C., & Varesano, A. (2018). Natural polymer-based electrospun fibers for antibacterial uses. In *Electrofluidodynamic Technologies (EFDTs) for Biomaterials and Medical Devices* (pp. 275-294). Woodhead Publishing.

Wang, H., Hao, L., Niu, B., Jiang, S., Cheng, J., & Jiang, S. (2016). Kinetics and antioxidant capacity of proanthocyanidins encapsulated in zein electrospun fibers by cyclic voltammetry. *Journal of agricultural and food chemistry*, 64(15), 3083-3090.

Wang, G., Yang, S., Wei, Z., Dong, X., Wang, H., & Qi, M. (2013). Facile preparation of poly (ε-caprolactone)/Fe 3 O 4@ graphene oxide superparamagnetic nanocomposites. *Polymer bulletin*, 70(8), 2359-2371.

Wang, H., Wang, J., Qiu, C., Ye, Y., Guo, X., Chen, G., . . . & Liu, R. H. (2017). Comparison of phytochemical profiles and health benefits in fiber and oil flaxseeds (Linum usitatissimum L.). *Food chemistry*, 214, 227-233.

Wang, L. F., & Rhim, J. W. (2016). Grapefruit seed extract incorporated antimicrobial LDPE and PLA films: Effect of type of polymer matrix. *LWT*, 74, 338-345.

Wang, S., Cao, X., Shen, M., Guo, R., Bányai, I., & Shi, X. (2012). Fabrication and morphology control of electrospun poly (γ-glutamic acid) nanofibers for biomedical applications. *Colloids and Surfaces B: Biointerfaces*, 89, 254-264.

Wang, S., Marcone, M. F., Barbut, S., & Lim, L. T. (2012). Fortification of dietary biopolymers-based packaging material with bioactive plant extracts. *Food research international*, 49(1), 80-91.

Wang, S., Marcone, M. F., Barbut, S., & Lim, L. T. (2013). Electrospun soy protein isolatebased fiber fortified with anthocyanin-rich red raspberry (Rubus strigosus) extracts. *Food research international*, 52(2), 467-472.

Wang, X., Bazuin, C. G., & Pellerin, C. (2015). Effect of small molecule hydrogen-bond crosslinker and solvent power on the electrospinnability of poly (4-vinyl pyridine). *Polymer*, 57, 62-69.

Wen, P., Zhu, D. H., Wu, H., Zong, M. H., Jing, Y. R., & Han, S. Y. (2016). Encapsulation of cinnamon essential oil in electrospun nanofibrous film for active food packaging. *Food Control*, 59, 366-376.

Woodruff, M. A., & Hutmacher, D. W. (2010). The return of a forgotten polymer Polycaprolactone in the 21st century. *Progress in polymer science*, 35(10), 1217-1256.

Yang, G., Lin, H., Rothrauff, B. B., Yu, S., & Tuan, R. S. (2016). Multilayered polycaprolactone/gelatin fiber-hydrogel composite for tendon tissue engineering. *Acta biomaterialia*, 35, 68-76.

Yuan, W., & Zhang, K. Q. (2012). Structural evolution of electrospun composite fibers from the blend of polyvinyl alcohol and polymer nanoparticles. *Langmuir*, 28(43), 15418-15424.

Zargham, S., Bazgir, S., Tavakoli, A., Rashidi, A. S., & Damerchely, R. (2012). The effect of flow rate on morphology and deposition area of electrospun nylon 6 nanofiber. *Journal of Engineered Fibers and Fabrics*, 7(4), 42-49, 1558925012007004 14.

Zhang, B., Kang, F., Tarascon, J. M., & Kim, J. K. (2016). Recent advances in electrospun carbon nanofibers and their application in electrochemical energy storage. *Progress in Materials Science*, 76, 319-380.

Zhou, C., Chu, R., Wu, R., & Wu, Q. (2011). Electrospun polyethylene oxide/cellulose nanocrystal composite nanofibrous mats with homogeneous and heterogeneous microstructures. *Biomacromolecules*, 12(7), 2617-2625.

Zhou, T., Wang, N., Xue, Y., Ding, T., Liu, X., Mo, X., & Sun, J. (2016). Electrospun tilapia collagen nanofibers accelerating wound healing via inducing keratinocytes proliferation and differentiation. *Colloids and Surfaces B: Biointerfaces*, 143, 415-422.

Zhu, J., & Marchant, R. E. (2011). Design properties of hydrogel tissue-engineering scaffolds. *Expert review of medical devices*, 8(5), 607-626.

(56) References Cited

OTHER PUBLICATIONS

Zong, X.H., Kim, K.S., Fang, D.F., Ran, S.F., Hsiao, B.S., & Chu, B. (2002). Structure and process relationship of electrospun bioabsorbable nanofiber membranes. Polymer, 43, 20 4403.

Aelenei et al., Tannic Acid Incorporation in Chitosan-Based Microparticles and in Vitro Controlled Release, J Mater Sci: Mater Med (2009) 20:1095-1102.

Afaq et al., Anthocyanin- and hydrolysable tannin-rich pomegranate fruit extract modulates MAPK and NF-kappaB pathways and inhibits skin tumorigenesis in CD-1 mice, Int. J. Cancer (2005) 113 (3): 423-433.

Alvarez et al., Influence of the electrical interface properties on the rheological behavior of sonicated soy lecithin dispersions, J. Colloid Interface Sci. (2007) 309(2): 279-82.

Alving et al., Liposomes as vehicles for vaccines, Prog. Clin. Biol. Res. (1980) 47: 339-55.

Alving, Liposomes as earners of Antigens and Adjuvants, J. Immunol. Methods (1991) 140(1): 1-13.

Arai et al., Bull. Tokai Reg. Fish Lab. (1968) 43: 89. (Book—Copy Not Provided).

Bala et al., 2013 (Rajni Bala, Pravin Pawar, Sushil Khanna, and Sandeep Arora. Orally dissolving strips; A new approach to oral drug delivery system. Int J Pharm investig. Apr.-Jun 2013; 3(2): 67-76.

Balde, A, T De Bruyne, L Pieters, H Kolodziej, D Vanden Berghe, M Claeys, A Vlietnck. "Tetrameric Proanthocyanidins Containing a Double Interflavanoid (A-Type) Linkage from Pavetta Owariensis." Phytochemistry, vol. 40, No. 3, 1995, pp. 933-948.

Beecher. (2003) Overview of dietary flavonoids: nomenclature, occurrence and intake, J. Nutrition; 133(10):3248S-3254S.

Benech et al. Inhibition of *Listeria innocua* in Cheddar cheese by addition of nisin Z in liposomes or by in situ production in mixed culture. Appl. Environ. Microbiol. (2002) 68:3683-90.

Berthold et al., Preparation and characterization of chitosan microspheres as drug carrier for prednisolone sodium phosphate as model for anti-inflammatory, J. Control Release (1996) vol. 39: 17-25.

Blumberg et al., Cranberries and their bioactive constituents in human health, 2013, American Society for Nutrition, Adv. Nutr. 4: 618-632.

Bu et al., Co-delivery of IL-2 or liposomes augment the responses of mice to a DNA vaccine for pseudorabies virus IE180 Comp. Immunol. Microbiol. Infect. Dis. (2003) 26(3): 175-87.

Burleigh et al., Consumption of sweetened, dried cranberries may reduce urinary tract infection incidence in susceptible women—a modified observational study. Nutrition Journal (2013), 12:139.

Calvo et al., Novel hydrophilic chitosan-polyethylene oxide nanoparticles as protein earners, J. Appl. Polym. Sci. (1997) vol. 63, 125-132.

Corradin et al., Novel adjuvants for vaccines, Curr. Med. Chem.—Anti-Inflammatory & Anti-Allergy Agents (2005) 4:1-7.

Czochanska et al., Compositional changes in lower molecular weight flavans during grape maturation (1979) : Phytochemistry 18:1819-1822 (Abstract Provided Only).

Gan et al., Modulation of surface charge, particle size and morphological properties of chitosan-TPP nanoparticles intended for gene delivery, Colloids Surf. B. 2005;44(2-3) :65-73.

Garlea et al., Chitosan-Polyphenols Nanostructured Matrices Drug Release Kinetics Studies, Analele Stiintifice ale Universitatii "Al. I. Cuza" din Iași (Serie Noua), Tomul IV, Biofizica, Fizica Medicala, Fizica Mediului, (2008), pp. 25-30, ISSN 1841-5318.

Gregoriadis et al., Liposome-mediated DNA vaccination, FEBS Lett. (1997) 402 : 107.

Gregoriadis G. Drug entrapment in liposomes. FEBS Lett. (1973) 36:292-6.

Gric et al., Mucoadhesive Chitosan-Coated Liposomes: Characteristics and Stability, Journal of Microencapsulation, (2001) vol. 18 No. 1, p. 3-12.

Guo et al., Chitosan-coated liposomes : Characterization and interaction with leuprolide, Int. J. Pharm. (2003) 260: 167-173.

Gupta et al., Adjuvants for human vaccines-current status, problems and future prospects, Vaccine (1995) 13: 1263.

Guzey et al., Formation, stability and properties of multilayer emulsions for application in the food industry. Adv. Colloid Interface Sci. (2006) 130:227-48.

Guzey et al., Impact of electrostatic interactions on formation and stability of emulsions containing oil droplets coated by beta-lactoglobulin-pectin complexes. J. Agric. Food Chem. (2007) 55(2):475-85.

Hedqvist et al., Characterisation of Tannins and in Vitro Protein Digestibility of Several Lotus Corniculatus Varieties, Animal Feed Science and Technology (2000) 87: 41-56.

Henriksen et al. Interactions between liposomes and chitosan II: effect of selected parameters on aggregation and leakage, Int. J. Pharm. (1997) 146:193-204.

Hong and McClements. Modulation of pH sensitivity of surface charge and aggregation stability of protein-coated lipid droplets by chitosan addition. Food Biophys. (2007) 2(1):46-55.

Howell et al., A-type cranberry proanthocyanidins and uropathogenic bacterial anti-adhesion activity, Phytochem. (2005) 66(18): 2281-2291.

Howell et al., Dosage effect on uropathogenic *Escherichia coli* anti-adhesion activity in urine following consumption of cranberry powder standardized for proanthocyanidin content: a multicentric randomized double blind study, BMC Infection Diseases (2010), 10:94.

Howell, Amy; Bioactive compounds in cranberries and their role in prevention of urinary tract infections, Molecular nutrition food Res (2007), 51: 732-737.

Illum et al., Chitosan as a novel nasal delivery system for vaccines, Adv. Drug Deliv. Rev. (2001) 51:81-96.

Illum., Chitosan and its use as a Pharmaceutical Excipient, Pharm. Res. (1998) 15 (vol. 9):1326-31.

Iwanaga et al., Application of Surface-Coated Liposomes for Oral Delivery of Peptide: Effects of Coating the Liposome's Surface on the GI Transit of Insulin, J. Pharm. Sci. (1999) 88:248-52.

Jameela et al., Progesterone-loaded chitosan microspheres: a long acting biodegradable controlled delivery system, J. Control. Release (1998) 52:17-24.

Janes et al., Polysaccharide colloidal particles as delivery systems for Macromolecules, Adv. Drug. Deliv. Rev. (2001) 47:83-97.

Jepson et al., Cranberries for preventing urinary tract infections (Review), 2013, The Cochrane Collaboration, reprint of the Cochrane Library 2012, Issue 10, pp. 1-80.

Jones et al., Quenched Bodipy dye-Labeled casein substrates for the assay of protease activity by direct fluorescence measurement, Anal. Biochem. (1997) 251:144.

Kato et al., Influence of Liposomes on Tryptic Digestion of Insulin, Biol. Pharm. Bull. (1993) 16: 457.

Khatri et al., Surface modified liposomes for nasal delivery of DNA vaccine, Vaccine (2008) 26: 2225-33.

Kim, S, Me Nimni, Z Yang, B Han. Chitosan/Gelatin-Based Films Crosslinked by Proanthocyanidin, Journal of Biomedial Research Part B: Applied Biomaterials, vol. 75B, 2005, pp. 442-450.

Krueger et al., Quantifying and characterizing proanthocyanidins in cranberries in relation to urinary tract health, Anal Bianal Chem (2013) 405:4385-4395.

Krueger, C.G. et al. Matrix-assisted laser desorption/Ionization time-of-flight mass spectrometry of anthocyanin-polyflavan-3-ol polymers in cranberry fruit [Vaccinium macrocarpon, Ait.] and spray dried cranberry juice, ACS Symposium, Uncovering the Mysteries of Red Wine Pigments. (2004) vol. 886: pp. 232-246.

Krueger, C.G. et al. Matrix-assisted laser desorption/ionization time-of-flight mass spectrometry of polygalloyl polyflavan-3-ols in grape seed extract., J Agric. Food Chem. (2000) 47: 3693-3710 and 48:1663-1667.

Kulkarni et al., In Vitro Studies on the Binding, Antioxidant, and Cytotoxic Actions of Punicalagin, Journal of Agricultural and Food Chemistry, (2007) vol. 55, pp. 1491-1500.

Kumar, Rajesh et al., Potential use of chitosan nanoparticles of oral delivery of DNA vaccine in Asian sea bass (Lates calcarifer) to protect from Vibrio (Listonella) anguillarum; Fish and Shellfish Immunology (2008), 25: 47-56.

Kumar et al. Chitosan chemistry and pharmaceutical perspectives, Chemical Reviews (2004) 104:6017-6084.

(56) References Cited

OTHER PUBLICATIONS

Lowry et al., Protein measurement with the folin phenol reagent, J. Biol. Chem. (1951) 193: 265-75.
Madrigal-Carballo et al., An approach to rheological and electrokinetic behaviour of lipidic vesicles covered with chitosan biopolymer. Colloids Surf., (2008) 323:149-154.
Madrigal-Carballo et al., Chitosomes loaded with cranberry proanthocyanidins attenuate the bacterial lipopolysaccharide-induced expression of iNOS and COX-2 in raw 264.7 macrophages, J. Liposome Res. (2009) 19(3): 189-196.
Manconi et al., Colloids and Surfaces A: Physicochemical and Engineering Aspects, Coll, and Surfaces A: Physicochem. Eng. Aspects. (2005) 270-271 102. (Abstract Provided Only).
Manconi et al., Development and characterization of liposomes containing glycols as carriers for diclofenac, Coll, and Surfaces A: Physicochem. Eng. Aspects. (2009) vol. 342 53-58.
McClements. Theoretical analysis of factors affecting the formation and stability of multilayered colloidal dispersions. Langmuir (2005) 21(21):9777-85.
McNeela et al., Intranasal immunization with genetically detoxified diphtheria toxin induces T cell responses in humans: enhancement of Th2 responses and toxin-neutralizing antibodies by formulation with chitosan, Vaccine. (2004) 22:909-14.
Mills et al., Protective Levels of Diphtheria-Neutralizing Antibody Induced in Healthy Volunteers by Unilateral Priming-Boosting Intranasal Immunization Associated with Restricted Ipsilateral Mucosal Secretory Immunoglobulin A, Infect. Immun. (2003) 71:726-32.
Mishra et al., Evaluation of uptake and generation of immune response by murine dendritic cells pulsed with hepatitis B surface antigen-loaded elastic liposomes, Vaccine (2007) 25:6939-6944).
Mokarram et al., Preparation and evaluation of chitosan nanoparticles containing Diphteria toxoid as new carriers for nasal vaccine delivery in mice, Archives of Razi Institute (2006) vol. 61, No. 1:13-25.
Muller et al., Nanosuspensions as particulate drug formulations in therapy: Rationale for development and what we can expect for the future, Adv. Drug Deliv. Rev. (2001) 47:3-19.
Nakanishi et al., Positively charged liposome functions as an efficient immunoadjuvant in inducing cell-mediated immune response to soluble proteins, Control. Release. (1999) 61:233-40.
Neto, et al., MALDI-TOF MS characterization of proanthocyanidins from cranberry fruit (Vacciniummacrocarpon) that inhibit tumor cell growth and matrix metalloproteinase expression in vitro, J. Sci. Food Agric., (2006) vol. 86, pp. 18-25.
Nishimura et al., Immunological activity of chitin and its derivatives, Vaccine. (1984) 2: 93-9.
Nishimura et al., Stimulation of cytokine production in mice using deacetylated chitin, Vaccine. (1986) 4:151-6.
Onishi, Y. Machida, Biodegradation and distribution of water-soluble chitosan in mice, Biomaterials. (1991) 20:175-82.
Pallandre et al., Improvement of stability of oil-in-water emulsions containing caseinate-coated droplets by addition of sodium alginate., J. Food Sci. (Nov./Dec. 2007) 72(9): E518-E524.
Peek et al., Nanotechnology in vaccine delivery, Adv. Drug Deliv. Rev. (2008) 60:915-928.
Popa, M-I, N Aelenei, VI Popa, D Andrei. Study of the interactions between polyphenolic compounds and chitosan. Reactive & Functional Polymers, vol. 45, 2000, pp. 35-43.
Porporatto et al., Local and systemic activity of the polysaccharide chitosan at lymphoid tissues after oral administration, Journal of Leukocyte Biology (2005), vol. 78:62-69.
Read et al., Effective nasal influenza vaccine delivery using chitosan, Vaccine. (2005) 23: 4367.
Rinaudo. Chitin and chitosan: Properties and applications, Progress in Polymer Science (2006) 31:603-632.
Roussy et al., Treatment of Ink-Containing Wastewater by Coagulation/Flocculation Using Biopolymers, Water SA vol. 31 No. 3 (http://www.wrc.org.za) Jul. 2005, pp. 369-376. ISSN 0378-4738.
Saupe et al., Immunostimulatory colloidal delivery systems for cancer vaccines, Expert Opin. Drug Deliv. (2006) 3:345-54.
Seeram et al., Pomegranate Phytochemicals, Pomegranates Medicinal and Aromatic Plants—Industrial Profiles (2006), pp. 1-29.
Seferian et al. Immune stimulating activity of two new chitosan containing adjuvant formulations, Vaccine (2000) 19:661-8.
Shanahan, F. (1994): The Intestinal Immune System. In Johnson, L.R., ed. Physiology of the Gastrointestinal Tract. New York: Raven Press, pp. 643-684. (Book—Copy Not Provided).
Singla et al., Chitosan: some pharmaceutical and biological aspects an update, J. Pharm. Pharmacol. (2001) 53: 1047.
Stagg et al., The dendritic cell: its role in intestinal inflammation and relationship with gut bacteria, Gut Journal (2003) 52:1522-1529.
Takeuchi et al., Enteral Absorption of Insulin in Rats from Mucoadhesive Chitosan-Coated Liposomes, Pharm. Res. (1996) 13:896-901.
Taylor et al., Liposomal nanocapsules in food science and agriculture. Crit. Rev. Food Sci. Nutr. (2005) 45:1-19.
Tezuka et al., Regulation of IgA production by naturally occurring TNF/iNOS-producing dendritic cells, Nature (2007) 448:929-933.
Van Der Lubben et al., Chitosan for mucosal vaccination, Adv. Drug Deliv. Rev. (2001) 52: 139-144.
Van Der Lubben et al., Chitosan microparticles for oral vaccination: preparation, characterization and preliminary in vivo uptake studies in murine Peyer's patches, Biomaterials (2001) 22:687.
Wahlberg, David; Are cranberries healthy? Probably, but science uncertain; Wisconsin State Journal (2015).
Wharton and Dieguez-Uribeonodo. The biology of Colletotrichum acutatum. Anales del Jardin Botanico de Madrid, 61(1):3-22 (2004).
Were et al., Size, stability, and entrapment efficiency of phospholipid nanocapsules containing polypeptide antimicrobials. J. Agric. Food Chem. (2003) 51:8073-9.
Yoshikawa et al., Augmentation of antigen-specific immune responses using DNA-fusogenic liposome vaccine, Biochem. Biophys. Res. Commun. (2004) 325:500.
Yuan, Y, BM Chesnutt, WO Haggard, JD Bumgardner. "Deacetylation of Chitosan: Material Characterization and in vitro Evaluation via Albumin Adsorption and Pre-Osteoblastic Cell Cultures." Materials, vol. 4, 2011, pp. 1399-1416.
Zaharoff et al., Chitosan solution enhances both humoral and cell-mediated immune responses to subcutaneous vaccination, Vaccine (2007) 25:2085-94.
Zhang, L, SL Kosaraju. "Biopolymeric delivery system for controlled release of polyphenolic antioxidants." European Polymer Journal, vol. 43, 2007, pp. 2956-2966.
Zhu et al., Rapid Identification of Gallotannins from Chinese Galls by Matrix-Assisted Laser Desorption/Ionization Time-of-Flight Quadrupole Ion Trap Mass Spectrometry, Rapid Commun. Mass Spec from. (2009); 23:1678-1682.
"Beads Formation in Electrospinning," ElectrospinTech, Aug. 19, 2014, pp. 1-2.
Furukawa, Ryutaro, et al. "Persimmon-derived tannin has antiviral effects and reduces the severity of infection and transmission of SARS-CoV-2 in a Syrian hamster model," Scientific Reports, 11, 2021, pp. 1-28.
Polycaprolactone. Wikipedia, 2022.
Tannin. Encyclopedia Britannica, 2022.
Tannic Acid. PubChem, 2022.

\* cited by examiner

COMPOSITE CHITOSAN-TANNIN-ACTIVE AGENT COMPOSITIONS AND METHODS OF MAKING AND USING SAME

BACKGROUND

Natural polymers have been used in many pharmaceutical applications. Chitosan, in particular, has been used for the preparation of nanoparticles, hydrogels, films, fibers, and tablets. In addition, chitosan has been used in formulations for oral, nasal, parenteral, transdermal, and ophthalmic drug delivery. However, chitosan-based materials have suffered from limited stability, biodegradability, and tensile strength. Chitosan-based materials suitable for pharmaceutical applications that overcome at least some of these deficiencies are needed.

SUMMARY OF THE INVENTION

The invention provides tannin-chitosan composite thin-films and other composite forms incorporating active pharmaceutical ingredients, including psilocybin (a psychedelic), biosimilars (melatonin and serotonin), and other active agents.

Exemplary films are fabricated with a tannin (grape seed extract):chitosan (fungal source) at a ratio of (10:90; w/w). Similar methods can be used for formulating thin-films with tannins and chitosan from alternative sources and at different w/w ratios. The tannin and chitosan powders can be mixed in water to first form a hydrogel. The active agent(s) can be solubilized in either water, ethanol, or other solvents at various doses (<1 mg-20 mg). The liquid solutions can be cast in silicone molds and dried, for example, at <40° C. over 72 hours in an oven. When removed from the molds, films of the invention demonstrate flexibility. The films of the invention can be dissolved in a small volume of water, simulating the dissolution that would occur in the oral cavity. The active agents can be released in dissolution tests in less than 5 minutes with up to 100% recovery as determined by quantitative high performance liquid chromatography with photodiode array detection.

The invention provides a better delivery platform than encapsulation or tableting because tannin-chitosan thin-films can dissolve quickly in the oral cavity, providing rapid release and early onset of the incorporated psilocybin (psychedelics) and biosimilars (melatonin, serotonin). Rapid release and onset of the active agent is a desirable attribute for certain indications such as, e.g., anxiety, panic attack. Tablets and capsules must first undergo dissolution in the GI tract, delaying onset of activity.

In addition, the invention provides tamper-resistant or abuse-deterrent formulations, which is particularly important for the envisioned payloads (e.g., psychedelic drugs). This is a high priority for the FDA when formulating Schedule I substances, including psilocybin, opioids, and other controlled substances. The active agents in the compositions of the invention, for example, are not easily purified and concentrated from the compositions without laboratory equipment.

The objects and advantages of the invention will appear more fully from the following detailed description of the preferred embodiment of the invention made in conjunction with the accompanying drawings.

DETAILED DESCRIPTION OF THE INVENTION

Figure 1:
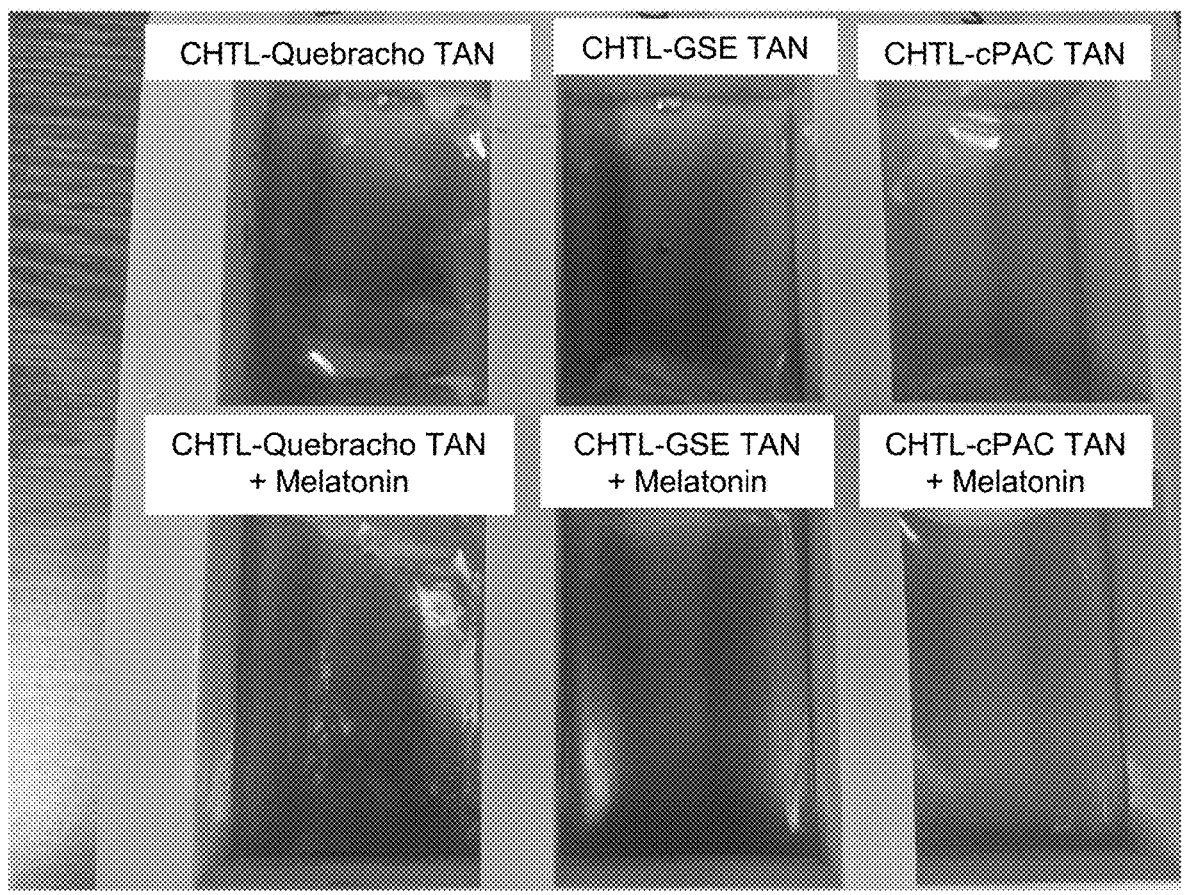
FIG. 1. Chitosan lactate-tannin (CHTL-TAN) films with or without melatonin. Quebracho TAN: quebracho tannin. GSE TAN: grape seed extract tannin. cPAC TAN: cranberry proanthocyanidin tannin.

The invention provides composite compositions. "Composite" is used herein to refer to a material comprising two or more constituent materials with significantly different physical or chemical properties.

The compositions of the invention comprise chitosan, tannin, and an active agent. In preferred versions, each of the chitosan, the tannin, and the active agent is evenly distributed throughout the composition with respect to each other.

Chitin is a biopolymer composed of substituted or unsubstituted glucosamine (such as N-acetyl glucosamine) polymer subunits. Chitin is the second most abundant biopolymer on earth, after only cellulose. It is commonly found in the exoskeleton or cuticles of many invertebrates, such as the shells of marine arthropods, and in the cell wall of most fungi and some algae. Chitin is generally insoluble in water but can be deacetylated by treatment with a caustic, such as sodium hydroxide, to form the soluble cationic polysaccharide, chitosan. The chemical name of an exemplary form of chitosan is poly(β-(1→4)-2-amino-2-deoxy-D-glucopyranose). In some versions, chitosan has two types of reactive groups that can be grafted: the amine groups on deacetylated units, and the hydroxyl groups on the C3 and C6 carbons on either acetylated or deacetylated units (Scheme 1).

Scheme 1. Exemplary Chitosan Structure.

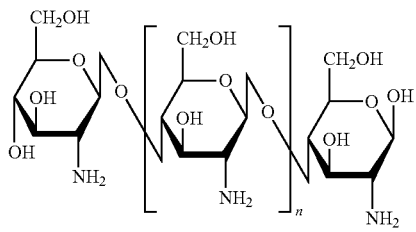

In some versions, the amine groups are substituted with various moieties, such as lactate. Versions of chitosan in which the amine groups are substituted with lactate are referred to as "chitosan lactate."

Chitosan is commonly used in water processing and in agriculture. Chitosan can also form a polycationic, biodegradable, and biocompatible matrix with blood clotting and antimicrobial properties. Kumar et al. (*Chemical Reviews* (2004) 104:6017-6084) and Rinaudo (*Progress in Polymer Science* (2006) 31:603-632) have reviewed the properties and applications of chitosan. Due to its unique polycationic nature, chitosan and its derivatives have been used for various applications in many different fields, including biomedicine, food, agriculture, biotechnology and pharmaceutics. Chitosan has been developed for a variety of biomedical applications including wound dressings and drug delivery systems.

Chitosan is commercially available from many chemical suppliers, such as Sigma Aldrich Co., St. Louis, MO. Chitosan is offered in various grades, average molecular weights, and degrees of deacetylation.

In some versions, the chitosan has a number average molecular weight of at least about 50 kDa, at least about 75 kDa, at least about 100 kDa, at least about 125 kDa, at least about 150 kDa, at least about 175 kDa, at least about 200 kDa, or at least about 250 kDa. In some versions, the chitosan has a number average molecular weight up to about 250 kDa, up to about 275 kDa, up to about 300 kDa, up to about 325 kDa, up to about 350 kDa, up to about 375 kDa, up to about 400 kDa, up to about 425 kDa, up to about 450 kDa, up to about 475 kDa, or up to about 500 kDa. In some versions, the chitosan has number average molecular weight from about 100 kDa to about 500 kDa, such as from about 200 kDa to about 350 kDa, or about 250 kDa to about 300 kDa. In some versions, the chitosan has number average molecular weight from about 100 kDa to about 400 kDa, from about 120 kDa to about 400 kDa, from about 150 kDa to about 400 kDa, from about 170 kDa to about 400 kDa, from 100 kDa to about 300 kDa, from about 120 kDa to about 300 kDa, from about 150 kDa to about 300 kDa, or from about 170 kDa to about 300 kDa. The value of n in Scheme 1 can be any number or range that results in approximately the values for the molecular weights of chitosan described herein. As would be readily recognized by one of skill in the art, chitosan as illustrated in Scheme 1 may also be partially acetylated, partially substituted with lactate, and/or partially substituted with other moieties.

Other embodiments may include low molecular weight chitosan. Low molecular weight chitosan refers to chitosan molecules with less than 100 polymer subunits (less than about 18 kDa or less than about 20 kDa). Molecular weights of chitosan can be determined, for example, by gel permeation chromatography.

The chitosan can have a degree of deacetylation that is typically at least about 70%, at least about 75%, at least about 80%, at least about 85%, at least about 90%, at least about 95%, at least about 99%, or the chitosan can be substantially fully deacetylated.

In some versions, the chitosan completely lacks lactate moieties or contains less than about 1 lactate moieties per polymer subunit, less than about $5 \times 10^{-1}$ lactate moieties per polymer subunit, less than about $1 \times 10^{-1}$ lactate moieties per polymer subunit, less than about $5 \times 10^{-2}$ lactate moieties per polymer subunit, less than about $1 \times 10^{-2}$ lactate moieties per polymer subunit, less than about $5 \times 10^{-3}$ lactate moieties per polymer subunit, less than about $1 \times 10^{-3}$ lactate moieties per polymer subunit, less than about $5 \times 10^{-4}$ lactate moieties per polymer subunit, less than about $1 \times 10^{-4}$ lactate moieties per polymer subunit, less than about $5 \times 10^{-5}$ lactate moieties per polymer subunit, less than about $1 \times 10^{-5}$ lactate moieties per polymer subunit, less than about $5 \times 10^{-6}$ lactate moieties per polymer subunit, less than about $1 \times 10^{-6}$ lactate moieties per polymer subunit, less than about $5 \times 10^{-7}$ lactate moieties per polymer subunit, less than about $1 \times 10^{-7}$ lactate moieties per polymer subunit, less than about $5 \times 10^{-8}$ lactate moieties per polymer subunit, less than about $1 \times 10^{-8}$ lactate moieties per polymer subunit, less than about $5 \times 10^{-9}$ lactate moieties per polymer subunit, less than about $1 \times 10^{-9}$ lactate moieties per polymer subunit, less than about $5 \times 10^{-10}$ lactate moieties per polymer subunit, less than about $1 \times 10^{-10}$ lactate moieties per polymer subunit, less than about $5 \times 10^{-15}$ lactate moieties per polymer subunit, less than about $1 \times 10^{-15}$ lactate moieties per polymer subunit, less than about $5 \times 10^{-20}$ lactate moieties per polymer subunit, or less than about $1 \times 10^{-20}$ lactate moieties per polymer subunit, wherein "polymer subunit" unit refers to a unsubstituted or substituted glucosamine (2-amino-2-deoxy-D-glucopyranose) moiety. As shown in the following examples, compositions of the invention made with lactate-containing chitosan ("chitosan lactate") leads to compositions that are sticky. Therefore, preferred compositions of the invention either lack chitosan with lactate moieties or contain chitosan with low amounts of lactate moieties per polymer subunit as described above.

Tannins include oligomeric polyphenols that occur naturally in a variety of plants, and modified forms thereof. Isolated tannins typically form a heterogeneous mixture of tannin compounds. Tannin compounds can be subdivided into two groups: condensed tannins, also known as proanthocyanidins ("PA" or "PAC"), and hydrolyzable tannins (HT). Tannin oligomers typically occur as dimers, trimers, tetramers, pentamers, hexamers, heptamers, octamers, nonamers, or decamers. Oligomers with greater than ten monomeric units can also be isolated, such as oligomers that include up to 50 units. For a review of tannin nomenclature, see Beecher (*J. Nutrition* 2003, 3248S-3254S), which is incorporated herein by reference. In some embodiments, certain monomerics or tannins with a low degree of polymerization (DP) can be excluded from a particular composition. For example, a composition may exclude catechin, tannic acid, or other monomers, dimeric tannins, trimers, or tetramers, PA tannins, or alternatively, HT tannins, a certain molecular weight range of tannins, or a type, class, or specific tannin cited in Beecher.

Proanthocyanidins are polymers of flavan-3-ols and flavans linked through an interflavan bond between carbon 4 of the C ring and carbon 8 of the A ring, as shown in Scheme 2. Scheme 2 illustrates a cranberry polyflavan-3-ol showing structural variation in the nature of interflavan linkage and substitution to an anthocyanin terminal unit through a $CH_3$—CH bridge.

Scheme 3 illustrates two other types of condensed tannins (PAs): procyanidins and prodelphinidins (for the trimer x=1; for the tetramer, x=2; for the pentamer, x=3; for the hexamer, x=4; for the heptamer, x=5; for the octamer, x=6; for the nonamer, x=7; and for the decamer, x=8). Procyanidins (R=H) contain catechin and/or epicatechin (CE) subunits; prodelphinidins (R=OH) contain gallocatechin and/or epigallocatchin (GE) subunits.

Scheme 3. Representative structures of proanthocyanidin (PA).

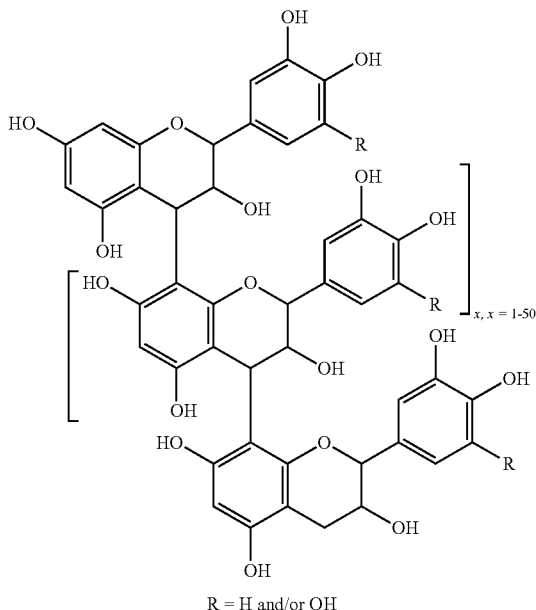

R = H and/or OH

Scheme 2. Representative structures of a proanthocyanidin (PA).

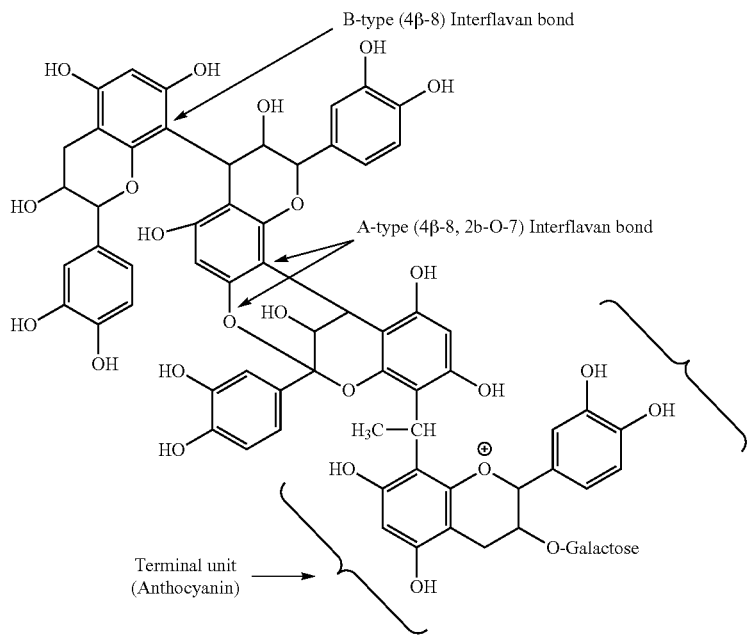

In various proanthocyanidins, the R groups of Scheme 3 can each independently be H or OH. In some embodiments, one or more hydroxyl groups may be glycosylated. In some embodiments, x is 1 to about 50, 1 to about 25, 1 to about 20, 1 to about 12, 1 to about 10, or a range of between any to integers from 1 to 50. The condensed tannins (PAs) can have various interflavanoid linkages (such as A-type 4→8 or 4→6 interflavan bonds, or B-type 4→8, 2→O-7 interflavan bonds, each α or β), cis- or trans-stereochemistry, and one or more hydroxyl groups can optionally be absent on the A-ring, B-ring, C-ring, or a combination thereof.

Other PA tannins include glycosylated heteropolyflavans, such as those illustrated in Scheme 4. Representative compounds shown in Scheme 4 include proluteolinidin ($R^1$=OH); proapigininidin ($R^1$=H); eriodictyol ($R^2$=H); and eriodictyol 5-O-β glucoside ($R^2$=glucose). Krueger et al. has described a variety of known heteropolyflavans-3-ols and glycosylated heteropolyflavans (see *J. Agric. Food Chem.* 2003, 51, 538-543, which is incorporated herein by reference).

Scheme 4. Representative structures of proanthocyanidins (PAs).

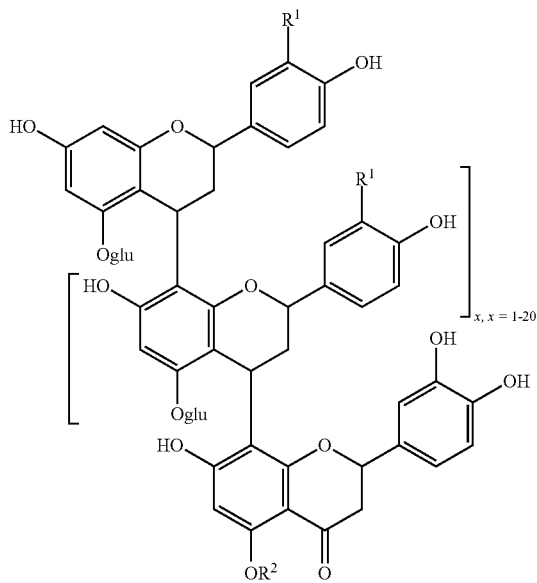

where $R^1$ is H or OH; $R^2$ is H or glucose; and glu is glucose (e.g., a β-glucoside).

In some embodiments, x of Scheme 4 is 1 to about 50, 1 to about 25, 1 to about 20, 1 to about 12, 1 to about 10, or a range of between any to integers from 1 to 50. Several examples of condensed tannins are described in U.S. Pat. No. 7,122,574 (Romanczyk et al.), which is incorporated herein by reference.

A review by Reed et al. (*Phytochem.* 66(18): 2248-2263 (2005)) describes the structural heterogeneity of tannin polyphenols from cranberries, grape seed extracts, sorghum, and pomegranates as characterized by MALDI-TOF MS. Examples of plants that produce proanthocyanidins include cranberries, blueberries, grapes, sorghum, and pine.

Hydrolyzable tannins include gallic acid and ellagic acid esters of polyol core moieties, such as sugars. Scheme 5 illustrates a pomegranate ellagitannin showing structural variation in nature of esterification of the glucose core molecule.

Scheme 5. Representative structure of a hydrolyzable tannin.

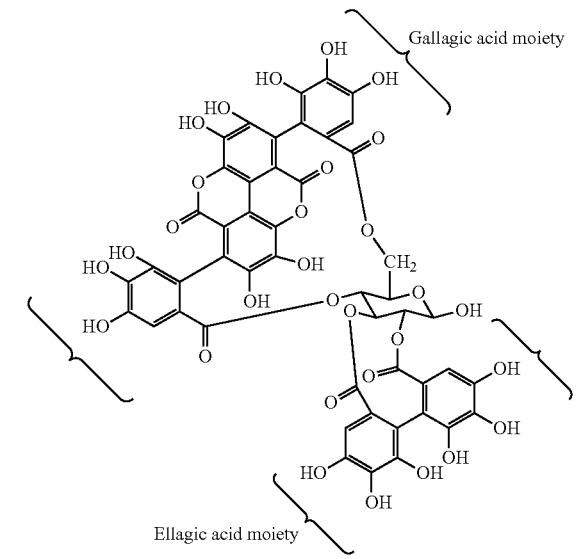

Hydrolyzable tannins, such as the compound shown in Scheme 5, can be isolated in oligomeric forms that include 2 to about 12 hydrolyzable tannin moieties, for example, linked by oxidative C—O coupling between galloyl and hexahydroxydiphenoyl moieties of the monomeric precursors. Common coupling also occurs between two ellagic acid moieties, or by addition of gallic acid moieties to the saccharide core of an oligomer. See Quideau and Feldman, *Chem. Rev.* 1996, 96, 475-503, which is incorporated herein in its entirety.

Accordingly, in some embodiments of compositions described herein, the hydrolyzable tannins employed will be oligomeric hydrolyzable tannins. Thus, in some embodiments, oligomeric hydrolyzable tannins include at least two saccharide core moieties. In some embodiments, a hydrolyzable tannin will include one or more (e.g., 1, 2, 3, 4, 5, or more) ellagic acid moieties, and in some embodiments, a hydrolyzable tannin will include one or more (e.g., 1, 2, 3, 4, 5, or more) gallagic acid moieties.

Examples of plants that produce hydrolyzable tannins include pomegranates, strawberries, raspberries, blackberries, and sumac. Significant quantities of hydrolyzable tannins can be isolated from, for example, pomegranate husks. Specific hydrolyzable tannins include punicalin and punicalagin (the alpha or beta isomer of 2,3-(S)-hexahydroxydiphenoyl-4,6-(S,S)-gallagyl-D-glucose, with a molecular weight of 1084) and stereochemical isomers thereof, as well as the hydrolyzable tannins described by Quideau and Feldman (*Chem. Rev.* 1996, 96, 475-503).

In some versions of the invention, the tannin in the composition comprises a condensed tannin, and the condensed tannin comprises a weight average molecular weight ($M_w$) of from about 100 Da to about 100,000 Da, such as from about 500 Da to about 100,000 Da or from about 1,000 Da to about 10,000 Da.

In some versions of the invention, the tannin in the composition comprises a hydrolyzable tannin, and the hydrolyzable tannin comprises a weight average molecular weight ($M_w$) of from about 100 Da to about 100,000 Da, such as from about 300 Da to about 30,000 Da or from about 1,000 Da to about 10,000 Da.

In some versions, the compositions of the invention comprise the chitosan and the tannin in a ratio by mass (mass chitosan:mass tannin) of about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, or 25:75 or within a range between any two of the foregoing ratios. Exemplary ranges include from about 99:1 (mass chitosan:mass tannin) to about 60:40 (mass chitosan:mass tannin), from about 99:1 to about 80:20, or from about 95:5 (mass chitosan:mass tannin) to about 85:15 (mass chitosan:mass tannin).

Some tannins can contain sulfonate groups. In some versions of the invention, the tannin in the composition completely lacks sulfonate moieties or contains less than about 1 sulfonate moieties per polymer subunit, less than about $5\times10^{-1}$ sulfonate moieties per polymer subunit, less than about $1\times10^{-1}$ sulfonate moieties per polymer subunit, less than about $5\times10^{-2}$ sulfonate moieties per polymer subunit, less than about $1\times10^{-2}$ sulfonate moieties per polymer subunit, less than about $5\times10^{-3}$ sulfonate moieties per polymer subunit, less than about $1\times10^{-3}$ sulfonate moieties per polymer subunit, less than about $5\times10^{-4}$ sulfonate moieties per polymer subunit, less than about $1\times10^{-4}$ sulfonate moieties per polymer subunit, less than about $5\times10^{-5}$ sulfonate moieties per polymer subunit, less than about $1\times10^{-5}$ sulfonate moieties per polymer subunit, less than about $5\times10^{-6}$ sulfonate moieties per polymer subunit, less than about $1\times10^{-6}$ sulfonate moieties per polymer subunit, less than about $5\times10^{-7}$ sulfonate moieties per polymer subunit, less than about $1\times10^{-7}$ sulfonate moieties per polymer subunit, less than about $5\times10^{-8}$ sulfonate moieties per polymer subunit, less than about $1\times10^{-8}$ sulfonate moieties per polymer subunit, less than about $5\times10^{-9}$ sulfonate moieties per polymer subunit, less than about $1\times10^{-9}$ sulfonate moieties per polymer subunit, less than about $5\times10^{-10}$ sulfonate moieties per polymer subunit, less than about $1\times10^{-10}$ sulfonate moieties per polymer subunit, less than about $5\times10^{-15}$ sulfonate moieties per polymer subunit, less than about $1\times10^{-15}$ sulfonate moieties per polymer subunit, less than about $5\times10^{-20}$ sulfonate moieties per polymer subunit, or less than about $1\times10^{-20}$ sulfonate moieties per polymer subunit. As shown in the following examples, compositions of the invention made with sulfonate-containing tannin leads to compositions that are brittle and unevenly distribute the active agent therein. Therefore, preferred compositions of the invention either lack sulfonated tannin or contain tannin with low amounts of sulfonate moieties per polymer subunit as described above.

In some versions, the active agent comprises a hallucinogen. Hallucinogens include various indole alkaloids, indoline alkaloids, indazole alkaloids, benzofuran alkaloids, and phenethylamines.

In some versions, the active agent comprises an indole alkaloid, an indoline alkaloid, an indazole alkaloid, a benzofuran alkaloid, or a phenethylamine. Indole alkaloids are alkaloids (both natural and synthetic) containing a structural moiety of indole. Indoline alkaloids are alkaloids (both natural and synthetic) containing a structural moiety of indoline. Indazole alkaloids are alkaloids (both natural and synthetic) containing a structural moiety of indazole. Benzofuran alkaloids are alkaloids (both natural and synthetic) containing a structural moiety of benzofuran. Phenethylamines are a chemical class of organic compounds that have a phenethylamine base structure and include unsubstituted phenethylamine and substituted phenethylamines.

Exemplary indole alkaloids include tryptamine alkaloids, and lysergamides. Indoline, indazole, or benzofuran analogs have an indoline, indazole, or benzofuran in place of the indole group. In some versions, the indole alkaloid is hallucinogenic.

Exemplary tryptamine alkaloids include tryptamine (3-(2-aminoethyl)indole or 2-(1H-indol-3-yl)ethanamine) and substituted tryptamines, which include substituted alpha-alkyltryptamines.

Exemplary substituted tryptamines include bufotenine (5-hydroxy-N,N-dimethyltryptamine), $N_\omega$-methylserotonin (norbufotenin) (5-hydroxy-N-methyltryptamine), serotonin (5-hydroxytryptamine), DMT (N,N-dimethyltryptamine), melatonin (5-methoxy-N-acetyltryptamine), N-acetylserotonin (5-hydroxy-N-acetyltryptamine), 5-bromo-DMT (5-bromo-N,N-dimethyltryptamine), 5-MeO-DMT (5-methoxy-N,N-dimethyltryptamine), 5-MeO-NMT (5-methoxy-N-methyltryptamine), NMT (N-methyltryptamine), norbaeocystin (4-phosphoryloxy-tryptamine), baeocystin (4-phosphoryloxy-N-methyl-tryptamine), psilocybin (4-phosphoryloxy-N,N-dimethyltryptamine), psilocin (4-hydroxy-N,N-dimethyltryptamine), tryptophan (α-carboxyltryptamine), DET (N,N-diethyltryptamine), DPT (N,N-dipropyltryptamine), DiPT (N,N-diisopropyltryptamine), DALT (N,N-diallyltryptamine), 5-MeO-DALT (5-methoxy-N,N-diallyltryptamine), 5-MeO-MALT (5-methoxy-N-Methyl-N-allyltryptamine), 5-MeO-DIPT (5-methoxy-N,N-diisopropyltryptamine), 5-MeO-MiPT (5-methoxy-N,N-methylisopropyltryptamine), 5-MT-NBOMe (5-methoxy-N-(ortho-methoxybenzyl)tryptamine), 5-BT (5-benzyloxytryptamine), 5-CT (5-carboxamidotryptamine), 5-ethoxy-DMT (5-ethoxy-N,N-dimethyltryptamine), 5-ethyl-DMT (5-ethyl-N,N-dimethyltryptamine), 5-fluoro-DMT (5-fluoro-N,N-dimethyltryptamine), 5-methyl-DMT (5,N,N-trimethyltryptamine), 5-(nonyloxy)tryptamine (5-nonyloxytryptamine), 4-HO-DET (4-hydroxy-N,N-diethyltryptamine), 4-AcO-DMT (4-acetoxy-N,N-dimethyltryptamine), 4-HO-MET (4-hydroxy-N-methyl-N-ethyltryptamine), 4-HO-EPT (4-hydroxy-N-ethyl-N-propyltryptamine), 4-HO-MPT (4-hydroxy-N-methyl-N-propyltryptamine), 4-HO-MiPT (4-hydroxy-N-isopropyl-N-methyltryptamine), 4-HO-McPT (4-hydroxy-N-cyclopropyl-N-methyltryptamine), 4-HO-McPeT (4-hydroxy-N-cyclopentyl-N-methyltryptamine), 4-HO-DPT (4-hydroxy-N,N-dipropyltryptamine), 4-HO-DIPT (4-hydroxy-N,N-diisopropyltryptamine), 4-HO-DSBT (4-hydroxy-N,N-disecbutyltryptamine), and zolmitriptan (5-(4-(S)-1,3-oxazolidin-2-one)-N,N-dimethyltryptamine).

Exemplary substituted α-alkyltryptamines include αMT (1-(1H-Indol-3-yl)propan-2-amine), 4-HO-αMT (3-(2-aminopropyl)-1H-indol-4-ol), 4-methyl-αMT (1-methyl-2-(4-methyl-1H-indol-3-yl)-ethylamine), 5-fluoro-αMT (1-(5-fluoro-1H-indol-3-yl)propan-2-amine), 5-chloro-αMT (1-(5-Chloro-1H-indol-3-yl)propan-2-amine), 5-HO-αMT ((3-(2-aminopropyl)-1H-indol-5-ol), 5-MeO-αMT (1-(5-methoxy-1H-indol-3-yl)propan-2-amine), 5-Ethoxy-αMT (1-(5-ethoxy-1H-indol-3-yl)propan-2-amine), 6-fluoro-αMT (1-(6-fluoro-1H-indol-3-yl)propan-2-amine), N-Methyl-5-MeO-αMT ([1-(5-methoxy-1H-indol-3-yl)propan-2-yl](methyl)amine), N,N-dimethyl-αMT (α,N,N-TMT), ((2-(1H-Indol-3-yl)-1-methyl-ethyl)dimethylamine), N,N-dimethyl-5-MeO-αMT ((2-(5-methoxy-1H-Indol-3-yl)-1-methyl-ethyl)dimethylamine), αMDiPT ((2-(1H-Indol-3-yl)-1-methyl-ethyl)diisopropylamine), BW-723C86 (1-[5-(2-Thienylmethoxy)-1H-indol-3-yl]-2-propanamine), AL-37350A (4,5-dihydropyrano-αMT) ((S)-(+)-1-(2-Aminopropyl)-8,9-dihydropyrano[3,2-e]indole), αET (1-(1H-indol-3-yl)butan-2-amine), 4-methyl-αET (1-(4-Methyl-1H-indol-3-yl)butan-2-amine), 4-HO-αET (1-(4-hydroxy-1H-indol-3-yl)butan-2-amine), 5-fluoro-αET (1-(5-fluoro-1H-indol-3-yl)butan-2-amine), 5-methyl-αET (1-(5-methyl-1H-indol-3-yl)butan-2-amine), 5-MeO-αET (1-(5-methoxy-1H- indol-3-yl)butan-2-amine), 7-methyl-αET (1-(7-methyl-1H-indol-3-yl)butan-2-amine), MPMI (3-[(1-methylpyrrolidin-2-yl)methyl]-1H-indole), lucigenol ((R)-3-(N-methylpyrrolidin-2-ylmethyl)-4-hydoxyindole), 5-MeO-MPMI (5-methoxy-3-{[(2R)-1-methylpyrrolidin-2-yl]methyl}-1H-indole), 5-F-MPMI (5-fluoro-3-[(1-methylpyrrolidin-2-yl)methyl]-1H-indole), 5-Br-MPMI (5-bromo-3-[(1-methylpyrrolidin-2-yl)methyl]-1H-indole), and eletriptan (3-{[(2R)-1-methylpyrrolidin-2-yl]methyl}-5-[2-(benzenesulfonyl)ethyl]-1H-indole).

Exemplary lysergamides include LSA/LAA (ergine, d-lysergic acid amide), DAM-57 (N,N-dimethyllysergamide), ergometrine (ergonovine), ergotamine, methergine, methysergide, amesergide, LY-215840, cabergoline, LAE-32 (D-lysergic acid ethylamide), LSB (lysergic acid 2-butyl amide), LSP (lysergic acid 3-pentyl amide), DAL (N,N-diallyllysergamide), MIPLA (methylisopropyllysergamide), ECPLA (N-ethyl-N-cyclopropyllysergamide), ETFELA (N-ethyl-N-(2,2,2-trifluoroethyl)lysergamide), LSD (lysergic acid diethylamide), ETH-LAD (6-ethyl-6-nor-lysergic acid diethylamide), AL-LAD (6-allyl-6-nor-LSD), IP-LAD (6-isopropyl-6-nor-lysergic acid diethylamide), BU-LAD (6-butyl-6-nor-lysergic acid diethylamide), ALD-52 (1-acetyl-LSD), 1P-LSD (1-propionyl-lysergic acid diethylamide), 1B-LSD (N1-butyryl-lysergic acid diethylamide), 1cP-LSD (N1-(cyclopropylmethanoyl)-lysergic acid diethylamide), 1P-ETH-LAD (1-propionyl-6-ethyl-6-nor-lysergic acid diethyamide), MLD-41 (N1-Methyl-lysergic acid diethylamide), LSM-775 (N-Morpholinyllysergamide), LPD-824 (N-Pyrrolidyllysergamide), LSD-Pip, LSD-Azapane, and LA-SS-Az (lysergic acid 2,4-dimethylazetidide)).

Other indole alkaloids include ibogaine, mitragynine, and yohimbine.

Exemplary substituted phenethylamines include meta-tyramine (3-hydroxyphenethylamine), para-tyramine (4-hydroxyphenethylamine), dopamine (3,4-dihydroxyphenethylamine), epinephrine (adrenaline) (β,3,4-trihydroxy-N-methylphenethylamine), norepinephrine (noradrenaline) (β,3,4-trihydroxyphenethylamine), meta-octopamine (β3-dihydroxyphenethylamine), para-octopamine (β,4-dihydroxyphenethylamine), phenylephrine (β3-dihydroxy-N-methylphenethylamine), 6-hydroxydopamine (2,4,5-trihydroxyphenethylamine), salbutamol (β,4-dihydroxy-3-hydroxymethyl-N-tert-butylphenethylamine), β-methylphenethylamine, amphetamine (α-methylphenethylamine), N-methylphenethylamine, N,N-dimethylphenethylamine, methamphetamine (N-methylamphetamine; N,α-dimethylphenethylamine), phentermine (α-methylamphetamine; α,α-dimethylphenethylamine), ortetamine (2-methylamphetamine; 2, α-dimethylphenethylamine), methylphenidate (N,α-butylene-β-methoxycarbonylphenethylamine), ephedrine/pseudoephedrine (N-methyl-β-hydroxyamphetamine), cathine (d-β-hydroxyamphetamine), cathinone (β-ketoamphetamine), methcathinone (N-methylcathinone), mephedrone (4-methylmethcathinone), ethcathinone (N-ethylcathinone), bupropion (3-chloro-N-tert-butyl-β-ketoamphetamine), norfenfluramine (3-trifluoromethyl-amphetamine), fenfluramine (3-trifluoromethyl-N-ethylamphetamine), 5-APB (5-(2-aminopropyl)benzofuran), 6-APB (6-(2-aminopropyl)benzofuran), MDA (3,4-methylenedioxy-amphetamine), MDEA (3,4-methylenedioxy-N-ethylamphetamine), MDMA (3,4-methylenedioxy-N-methylamphetamine), MDMC (3,4-methylenedioxymethcathinone), MMDA (5-methoxy-3,4-methylenedioxy-amphetamine), MMDMA (5-methoxy-3,4-methylenedioxy-N-methylamphetamine), mescaline (3,4,5-trimethoxyphenethylamine), proscaline (2-(3,5-dimethoxy-4-propoxyphenyl)ethanamine), metaescaline (2-(3-ethoxy-4,5-dimethoxyphenyl)ethanamine), allylescaline (4-Allyloxy-3,5-dimethyloxyphenylethylamine), methallylescaline (4-methallyloxy-3,5-dimethoxyphenethylamine), asymbescaline (3,4-diethoxy-5-methoxyphenethylamine), DOM (2,5-dimethoxy-4-methylamphetamine), DOB (2,5-dimethoxy-4-bromoamphetamine), DOI (2,5-dimethoxy-4-iodoamphetamine), DON (2,5-dimethoxy-4-nitroamphetamine), DOC (2,5-dimethoxy-4-chloroamphetamine), 2C-B (2,5-dimethoxy-4-bromophenethylamine), βk-2C-B (2,5-dimethoxy-4-bromo-β-ketophenethylamine), 2C-C (2,5-dimethoxy-4-chlorophenethylamine), 2C-I (2,5-dimethoxy-4-iodophenethylamine), 2C-D (2,5-dimethoxy-4-methylphenethylamine), 2C-E (2,5-dimethoxy-4-ethylphenethylamine), 2C-P (2,5-dimethoxy-4-propylphenethylamine), 2C-F (2,5-dimethoxy-4-fluorophenethylamine), 2C-N (2,5-dimethoxy-4-nitrophenethylamine), 2C-T-2 (2,5-dimethoxy-4-ethylthio-phenethylamine), 2C-T-4 (2,5-dimethoxy-4-isopropylthio-phenethylamine), 2C-T-7 (2,5-dimethoxy-4-propylthio-phenethylamine), 2C-T-8 (2,5-dimethoxy-4-cyclopropylmethylthio-phenethylamine), 2C-T-19 (2,5-dimethoxy-4-tert-butylthio-phenethylamine), 2C-T-21 (2,5-dimethoxy-4-(2-fluoroethylthio)-phenethylamine), 25B-NBOMe (2-(4-bromo-2,5-dimethoxyphenyl)-N-[(2-methoxyphenyl)methyl]ethanamine), 25C-NBOMe (2-(4-chloro-2,5-dimethoxyphenyl)-N-[(2-methoxyphenyl)methyl]ethanamine), 25I-NBOMe (2-(4-iodo-2,5-dimethoxyphenyl)-N-[(2-methoxyphenyl)methyl]ethanamine), 25D-NBOMe (2-(4-methyl-2,5-dimethoxyphenyl)-N-[(2-methoxyphenyl)methyl]ethanamine), 25E-NBOMe (2-(4-ethyl-2,5-dimethoxyphenyl)-N-[(2-methoxyphenyl)methyl]ethanamine), 25P-NBOMe (2-(4-propyl-2,5-dimethoxyphenyl)-N-[(2-methoxyphenyl)methyl]ethanamine), 25F-NBOMe (2-(4-fluoro-2,5-dimethoxyphenyl)-N-[(2-methoxyphenyl)methyl]ethanamine), mescaline-NBOMe (N-(2-methoxybenzyl)-2-(3,4,5-trimethoxyphenyl)ethanamine), 25I-NBOH (N-(2-hydroxybenzyl)-2,5-dimethoxy-4-iodo-phenethylamine), 25C-NBOH (N-(2-hydroxybenzyl)-2,5-dimethoxy-4-chloro-phenethylamine), 25B-NBOH (N-(2-hydroxybenzyl)-2,5-dimethoxy-4-bromo-phenethylamine), 25I-NBF (N-(2-fluorobenzyl)-2,5-dimethoxy-4-iodo-phenethylamine), amfepramone (diethylpropion) (N-diethyl-(3-ketoamphetamine), and 1,3-benzodioxole alkaloids.

In some versions, the active agent is present in the composition in an amount of 0.001-500 mg, or any subrange therebetween. Amounts above and below this range are acceptable in other versions. Exemplary amounts include 0.001 mg, 0.005 mg, 0.01 mg, 0.05 mg, 0.1 mg, 0.5 mg, 1 mg, 5 mg, 10 mg, 50 mg, 100 mg, 150 mg, 200 mg, 250 mg, 300 mg, 350 mg, 400 mg, 450 mg, or 500 mg, or any range between any two of the foregoing values.

In some versions, the composition has a volume in a range of 1-300 mL, or any subrange therein. Volumes above and below this range are acceptable in other versions. Exemplary volumes include 1 mL, 5 mL, 10 mL, 50 mL, 100 mL, 150 mL, 200 mL, 250 mL, or 300 mL, or any range between any two of the foregoing values.

The active agent can be synthesized or obtained from natural sources. The active agents obtained from natural sources can be in the form of a crude or refined extract from a botanical source (e.g., magic mushrooms), typically in combination with a mixture of other isolated compounds.

In addition to the chitosan, tannin, and active agent, the compositions of the invention can include any of a number of other components. Such components can include sweeteners (e.g., sucralose, sucrose), flavoring agents (e.g., essential oil), carboxymethylcellulose, sodium lauryl sulfate, citric acid, ascorbic acid, glycerol, and excipients.

The compositions of the invention can take any of a number of forms. Exemplary forms include films (e.g., thin films or oral thin films), foams, wafers (e.g., oral wafers; dissolvable products that are not thin films), gels (e.g., hydrogels), and nanoparticles. See, e.g., Bala et al. 2013 (Rajni Bala, Pravin Pawar, Sushil Khanna, and Sandeep Arora. Orally dissolving strips: A new approach to oral drug delivery system. Int J Pharm Investig. 2013 April-June; 3(2): 67-76), which is incorporated by reference in its entirety, for information on oral thin films and oral wafers.

The compositions of the invention preferably have a characteristic of dissolving in an aqueous solution in a short amount of time. In various versions of the invention, the composition dissolves in an aqueous solution within 1 minute, with 1.5 minutes, within 2 minutes, within 2.5 minutes, within 3 minutes, within 3.5 minutes, within 4 minutes, within 4.5 minutes, within 5 minutes, within 5.5 minutes, within 6 minutes, within 6.5 minutes, or within 7 minutes. "Dissolves" as used in this context refers to when the composition begins to break down in the aqueous solution, regardless of the amount of time it takes to completely bread down and disappear. "Aqueous solution" refers to a solution containing at least 75% w/w water, such as at least 80% w/w water, at least 85% w/w water, at least 90% w/w water, at least 95% w/w water, at least 96% w/w water, at least 97% w/w water, at least 98% w/w water, or at least 99% w/w water. An exemplary aqueous solution is saliva. Other exemplary aqueous solutions are those in the following examples designed to mimic saliva.

Preferred versions of the invention are directed to compositions that comprise a characteristic selected from the group consisting of being non-sticky, being non-brittle, having the chitosan, the tannin, and the active agent being evenly distributed throughout the composition, dissolving in an aqueous solution within a short amount of time, and any combination thereof. "Non-sticky" refers to the characteristic of being able to be removed from a surface, such as a silicon surface without tearing, breaking or separating. "Non-brittle" refers to the characteristic of having at least some degree of flexibility without cracking. The characteristic of having the chitosan, the tannin, and the active agent being evenly distributed throughout the composition refers to a homogeneous dispersal or distribution of each throughout the composition. The characteristic of dissolving in an aqueous solution within a short amount of time refers to having any of the parameters described in the immediately foregoing paragraph. In some versions, such compositions consists essentially of chitosan lacking lactate moieties, condensed tannin lacking sulfonate moieties, an active agent consisting essentially of any one or more of an indole alkaloid and a phenethylamine, and, optionally, one or more additional ingredients that do not materially affect one or more of the characteristics outlined above. In some versions, such compositions are in the form of a film or a foam.

Methods of making the compositions of the invention can comprise mixing the chitosan, the tannin, and the active agent in a solvent to form a mixture and drying the mixture to form the composite composition. The solvent preferably comprises at least 70% w/w, at least 75% w/w, at least 80% w/w, at least 85% w/w, at least 90% w/w, at least 95% w/w, at least 96% w/w, at least 97% w/w, at least 98% w/w, or at least 99% w/w of a polar protic solvent. Exemplary polar protic solvents include water, alcohols such as methanol, ethanol, and isopropyl alcohol, acetic acid, formic acid, nitromethane, and combinations thereof. To generate films of the invention, the drying can be performed at room temperature or in an oven. The drying may be performed with or without a vacuum to aid in drying efficiency. To generate foams of the invention, the drying can be performed by freeze-drying.

In some versions, the films can be produced by continuous extrusion onto a moving surface and/or in large pans that are subjected to forced-air drying or vacuum-assisted drying. The drying can be done on a moving bed following continuous extrusion.

The mixture preferably has a pH from about 4 to about 7.5, such as about 5.0 to about 6.5.

The chitosan, tannin, and active agent employed in the methods can include any type of chitosan, tannin, or active agent described herein in any amount and/or relative weight ratio.

The mixture can include other elements or components, such as any other type of element or component described herein.

The invention also provides methods of administering an active agent to a subject. The methods can comprise a composition as described herein to the subject. In some versions, the administering comprises orally administering the composition to the subject. In some versions, the oral administration comprises oral mucosal administration. Oral mucosal administration is administration in which an active agent is applied to the oral mucosa, diffuses through the oral mucosa, and enters directly into the bloodstream. Oral mucosal administration comprises buccal administration. In some versions, the composition is in the form of a film, wherein the film is placed in the subject's mouth and permitted to dissolve in the subject's mouth without the need to swallow the composition intact. In some versions, the administering comprises parenterally administering the composition. In some versions, the composition is in the form of a hydrogel and the composition is administered by injection.

As used herein, "polymer subunit" refers to a repeating subunit or type of subunit that makes up a given polymer.

U.S. Pat. No. 10,104,888 is incorporated herein by reference in its entirety.

The compositions of the invention can consist essentially or consist of any one or more elements described herein as being comprised by the compositions of the invention.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1

Chitosan-Tannin Composite Films

Background

Fast dissolving films are gaining interest as an alternative of fast dissolving tablets. The films are designed to dissolve upon contact with a wet surface, such as the tongue, within a few seconds, meaning the consumer can take the product without need for additional liquid. This convenience provides both a marketing advantage and increased patient compliance. As the drug is directly absorbed into systemic circulation, degradation in the gastrointestinal tract and first-pass effects can be avoided. The present examples provide chitosan-tannin composite films containing active agents. The films are suitable for use for buccal administration of the active agents.

CHT-TAN Composite Films—Thickness

The purpose of study was to determine the effect of total volume and effect of chitosan-tannin concentration on film thickness. Results indicate that smaller volumes cast into molds result in thinner films and that lower concentrations of chitosan and tannins in similar volumes result in thinner films.

Chitosan (CHT) stock solutions of 5 and 10 mg/mL low molecular weight were prepared by dissolving CHT (>98.0% deacetylated, Product No. C-M-95-401132, Lot No. 351821, ChitoLytic, Ontario, Canada) in acetic acid (0.5% v/v). Stock solutions of tannins (TAN) (quebracho extract, TAN'ACTIVE QS-SOL, Silvateam, Wilton, CT) of 5 and 10 mg/mL were prepared in ethanol. CHT-TAN composite solutions were prepared as follows: the TAN stock solution was added to the CHT stock solution under continuous stirring for 10 min at a weight ratio of 90:10 (CHT:TAN). The mixture was left under constant mechanical stirring for 20 min at room temperature.

Volumes of 10, 20, and 30 mL of the CHT-TAN composite solutions were added to a silicon mold (7.9×5.6×2.5 cm). The samples were placed in an oven at 36° C. for 48 hours. After drying, samples were kept in a desiccator for long term storage. See Table 1.

TABLE 1

| | Chitosan (CHT) | | | Tannin (TAN) | | |
|---|---|---|---|---|---|---|
| | Conc. (mg/mL) | Vol. (mL) | Total (mg) | Conc. (mg/mL) | Vol. (mL) | Total (mg) |
| Chitosan 5 mg/mL CHT:TAN 90:10 Volume 10 mL 0.03 mm | 5.0 | 9.0 | 45.0 | 5.0 | 1.0 | 5.0 |
| Chitosan 5 mg/mL CHT:TAN 90:10 Volume 20 mL 0.03 mm | 5.0 | 18.0 | 90.0 | 5.0 | 2.0 | 10.0 |
| Chitosan 5 mg/mL CHT:TAN 90:10 Volume 30 mL 0.05 mm | 5.0 | 27.0 | 135.0 | 5.0 | 3.0 | 15.0 |
| Chitosan 10 mg/mL CHT:TAN 90:10 Volume 10 mL 0.03 mm | 10.0 | 9.0 | 90.0 | 10.0 | 1.0 | 10.0 |
| Chitosan 10 mg/mL CHT:TAN 90:10 Volume 20 mL 0.05 mm | 10.0 | 18.0 | 180.0 | 10.0 | 2.0 | 20.0 |
| Chitosan 10 mg/mL CHT:TAN 90:10 Volume 30 mL 0.08 mm | 10.0 | 27.0 | 270.0 | 10.0 | 3.0 | 30.0 |

CHT-TAN Composite Films—Acid Effect

CHT stock solutions of 10 mg/mL low molecular weight CHT (>98.0% deacetylated, Product No. C-M-95-401132, Lot No. 351821, ChitoLytic, Ontario, Canada) were prepared by dissolving CHT in acetic acid (0.5% v/v). A stock solution of TAN (10.0 mg/mL) (quebracho extract, TAN'ACTIVE QS-SOL, Silvateam, Wilton, CT) was prepared in ethanol. CHT-TAN composite solutions were prepared as follows: First, the pH of the CHT solutions were adjusted to 4.0, 4.5, 5.0, 5.5, or 6.0 using 1M NaOH or 1M HCl. Then, the TAN stock solution was added to the CHT stock solutions at the different pH levels under continuous stirring for 10 min at a weight ratio of 90:10 (CHT:TAN). The mixture was left under constant mechanical stirring for 20 min at room temperature.

The CHT-TAN composite solutions were added to a silicon mold (7.9×5.6×2.5 cm) and placed in an oven at 36° C. for 48 hours. After dried, samples were kept in a desiccator for long term storage. See Table 2.

TABLE 2

| | Chitosan (CHT) | | | Tannin (TAN) | | |
|---|---|---|---|---|---|---|
| | Conc. (mg/mL) | Vol. (mL) | Total (mg) | Conc. (mg/mL) | Vol. (mL) | Total (mg) |
| CHT:TAN (90:10) pH 4.0 | 10.0 | 27.0 | 270.0 | 10.0 | 3.0 | 30.0 |
| CHT:TAN (90:10) pH 4.5 | 10.0 | 27.0 | 270.0 | 10.0 | 3.0 | 30.0 |
| CHT:TAN (90:10) pH 5.0 | 10.0 | 27.0 | 270.0 | 10.0 | 3.0 | 30.0 |
| CHT:TAN (90:10) pH 5.5 | 10.0 | 27.0 | 270.0 | 10.0 | 3.0 | 30.0 |
| CHT:TAN (90:10) pH 6.0 | 10.0 | 27.0 | 270.0 | 10.0 | 3.0 | 30.0 |

The films were evaluated subjectively for flexibility and fragility. Films in the lower pH range (4, 4.5) were fragile and less desirable than at the higher pH ranges.

Sucralose Loading of CHT-TAN Composite Films

CHT stock solutions of 10 mg/mL low molecular weight was prepared by dissolving CHT (>98.0% deacetylated, Product No. C-M-95-401132, Lot No. 351821, ChitoLytic, Ontario, Canada) in acetic acid (0.5% v/v). A stock solution of TAN (40.0 mg/mL) (quebracho extract, TAN'ACTIVE QS-SOL, Silvateam, Wilton, CT) was prepared in ethanol, and stock solution of sucralose (1.0 and 20.0 mg/mL) were prepared in water. CHT-TAN composite solutions were prepared as follows: the TAN stock solution was added to the CHT stock solution under continuous stirring for 10 min at a weight ratio of 90:10 (CHT:TAN), then the sucralose solution was added to the mixture while stirring continuously to constitute 0.03% w/w, 0.10% w/w, 0.20% w/w, 0.83% w/w, 1.66% w/w, 2.50% w/w, 3.33% w/w, and 5.00% w/w of the combined total of the chitosan, tannin, and sucralose. Then, the CHT-TAN composite solutions were added to a silicon mold (7.9×5.6×2.5 cm). The mold was placed in an oven at 36° C. for 48 hours. After dried, samples were kept in a desiccator for long term storage. See Table 3.

TABLE 3

|  | Chitosan (CHT) | | | Tannin (TAN) | | | Sucralose | | |
| --- | --- | --- | --- | --- | --- | --- | --- | --- | --- |
|  | Conc. (mg/mL) | Vol. (mL) | Total (mg) | Conc. (mg/mL) | Vol. (mL) | Total (mg) | Conc. (mg/mL) | Vol. (mL) | Total (mg) |
| CHT:TAN (90:10) 0.0% Sucralose | 10.0 | 27.0 | 270.0 | 10.0 | 3.0 | 30.0 | 1.0 | 0 | 0 |
| CHT:TAN (90:10) 0.03% Sucralose | 10.0 | 27.0 | 270.0 | 10.0 | 3.0 | 30.0 | 1.0 | 0.1 | 0.1 |
| CHT:TAN (90:10) 0.1% Sucralose | 10.0 | 27.0 | 270.0 | 10.0 | 3.0 | 30.0 | 1.0 | 0.3 | 0.3 |
| CHT:TAN (90:10) 0.2% Sucralose | 10.0 | 27.0 | 270.0 | 10.0 | 3.0 | 30.0 | 1.0 | 0.6 | 0.6 |
| CHT:TAN (90:10) 0.83% Sucralose | 10.0 | 27.0 | 270.0 | 10.0 | 3.0 | 30.0 | 20.0 | 0.125 | 2.5 |
| CHT:TAN (90:10) 1.66% Sucralose | 10.0 | 27.0 | 270.0 | 10.0 | 3.0 | 30.0 | 20.0 | 0.250 | 5.0 |
| CHT:TAN (90:10) 2.50% Sucralose | 10.0 | 27.0 | 270.0 | 10.0 | 3.0 | 30.0 | 20.0 | 0.375 | 7.5 |
| CHT:TAN (90:10) 3.33% Sucralose | 10.0 | 27.0 | 270.0 | 10.0 | 3.0 | 30.0 | 20.0 | 0.500 | 10.0 |
| CHT:TAN (90:10) 5.00% Sucralose | 10.0 | 27.0 | 270.0 | 10.0 | 3.0 | 30.0 | 20.0 | 0.750 | 15.0 |

Example 2

Melatonin-Loaded Chitosan-Tannin Composite Films

Melatonin Loading of CHTL-TAN Composite Films

A stock solution of chitosan lactate (CHTL) (>95.0% deacetylated, Product No. AL-10131, Lot No. 22022) at 10 mg/mL was prepared in water. Stock solutions of different preparations of tannin (TAN) at 10 mg/mL were prepared in ethanol. The TAN preparations were quebracho extract (TAN'ACTIVE QS-SOL, Silvateam, Wilton, CT), grape seed extract (GSE) (TAN'ACTIVE GUT, Batch: 010417, Silvateam, Wilton, CT), and cranberry proanthocyanidin extract (cPAC) prepared using common methods known in the art. A stock solution of melatonin at 50.0 mg/mL was prepared in ethanol. CHTL-TAN composite solutions were prepared as follows: TAN stock solution was added to the CHTL stock solution under continuous stirring for 10 min at a weight ratio of 90:10 (CHTL:TAN). Then, the melatonin solution was added to the mixture while stirring continuously (yielding 7.00% w/v of the solution). Volumes of 30 mL of the CHTL-TAN composite solutions were added to a silicon mold (7.9×5.6×2.5 cm). The samples were placed in an oven at 36° C. for 3 days. See Table 4.

TABLE 4

|  | Chitosan Lactate (CHTL) | | | Tannin (TAN) | | | Melatonin | | |
| --- | --- | --- | --- | --- | --- | --- | --- | --- | --- |
|  | Conc. (mg/mL) | Vol. (mL) | Total (mg) | Conc. (mg/mL) | Vol. (mL) | Total (mg) | Conc. (mg/mL) | Vol. (mL) | Total (mg) |
| CHTL:TAN (90:10) 0 mg of Melatonin Quebracho | 10.0 | 27.0 | 270.0 | 10.0 | 3.0 | 30.0 | 50.0 | 0 | 0 |
| CHTL:TAN (90:10) 22.6 mg of Melatonin Quebracho | 10.0 | 27.0 | 270.0 | 10.0 | 3.0 | 30.0 | 50.0 | 0.452 | 22.6 |
| CHTL:TAN (90:10) 0 mg of Melatonin Grape Seed Extract | 10.0 | 27.0 | 270.0 | 10.0 | 3.0 | 30.0 | 50.0 | 0 | 0 |
| CHTL:TAN (90:10) 22.6 mg of Melatonin Grape Seed Extract | 10.0 | 27.0 | 270.0 | 10.0 | 3.0 | 30.0 | 50.0 | 0.452 | 22.6 |
| CHTL:TAN (90:10) 0 mg of Melatonin Cranberry PAC | 10.0 | 27.0 | 270.0 | 10.0 | 3.0 | 30.0 | 50.0 | 0 | 0 |
| CHTL:TAN (90:10) 22.6 mg of Melatonin Cranberry PAC | 10.0 | 27.0 | 270.0 | 10.0 | 3.0 | 30.0 | 50.0 | 0.452 | 22.6 |

Figure 2:
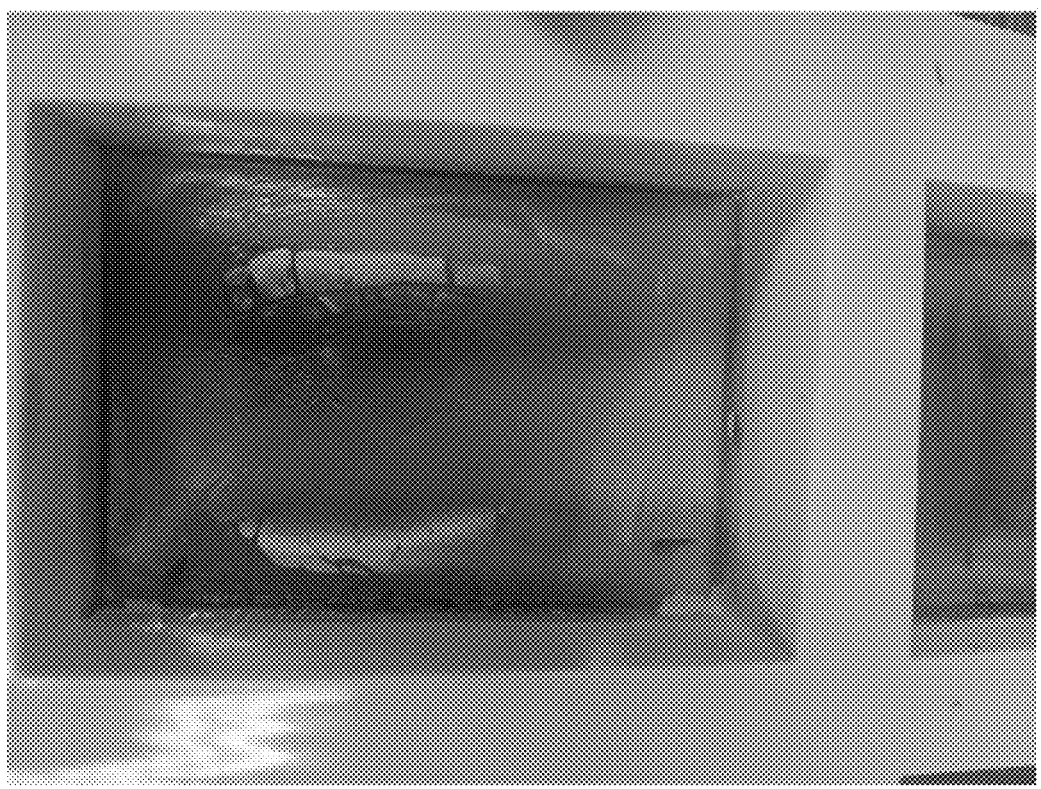
FIG. 2. Chitosan lactate-quebracho tannin (CHTL-TAN) film with melatonin.

The chitosan lactate and quebracho tannin+/−melatonin resulted in undesirable film characteristics (FIG. 1, left column, and FIG. 2). The films stuck to the mold, the melatonin was not homogeneously dispersed through film, and the films fractured. These observations were unexpected, as the source of tannins and chitosan was not expected to have an impact the ability to form stable films. Quebracho tannins are sulfonated during the extraction and production process. We predict the sulfur substitution with the chitosan lactate results in brittle film characteristics. Chitosan lactate is a water soluble chitosan ingredient, the pH of the chitosan lactate in solution and the interaction with the sulfonated tannins could also be responsible for the brittle films.

Figure 3:
FIG. 3. Chitosan lactate-grape seed extract (GSE) tannin (CHTL-TAN) film with melatonin.
Figure 4:
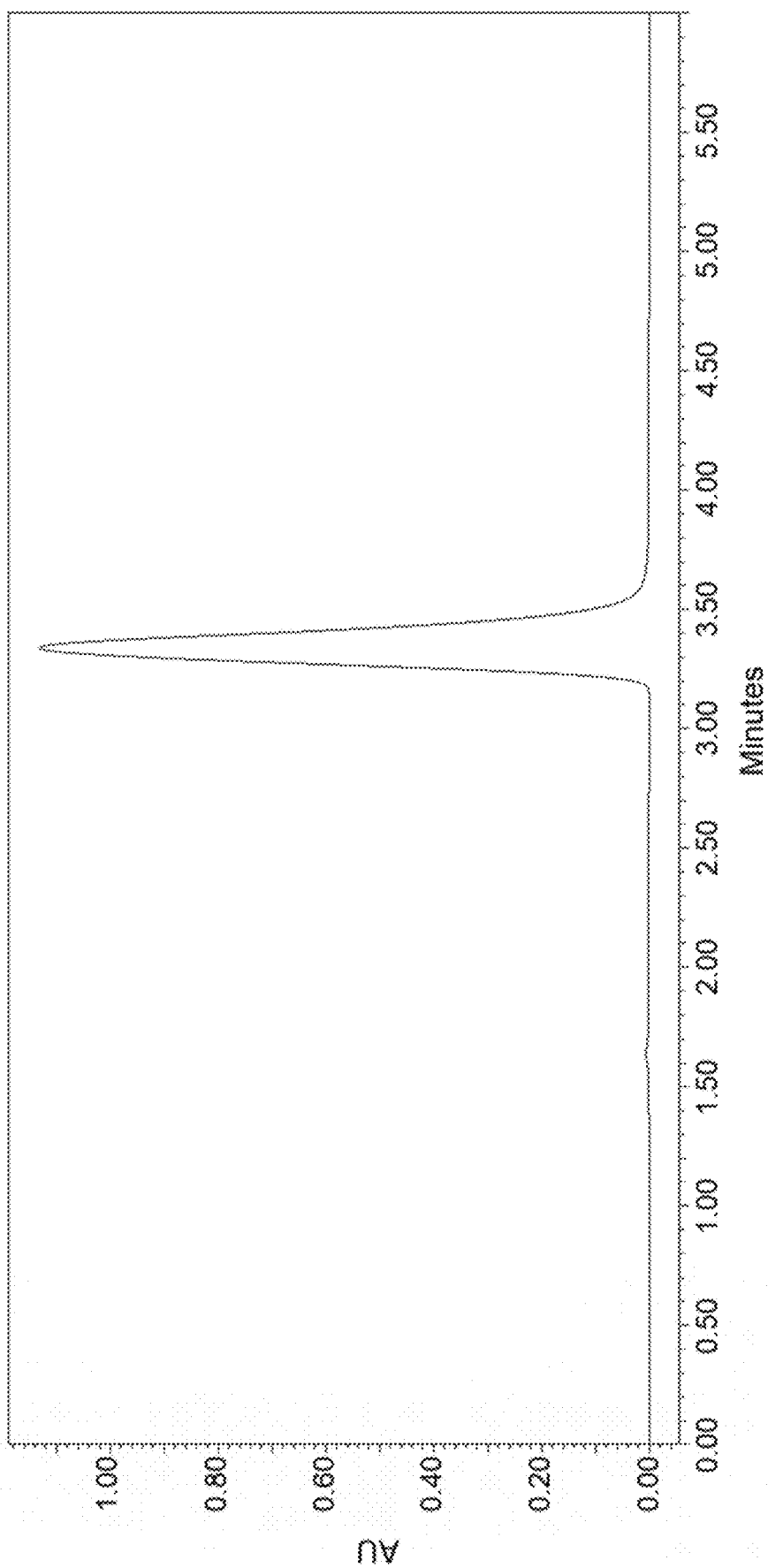
FIG. 4. HPLC chromatogram of melatonin at 100 µg/mL, recorded at 280 nm.
Figure 5:
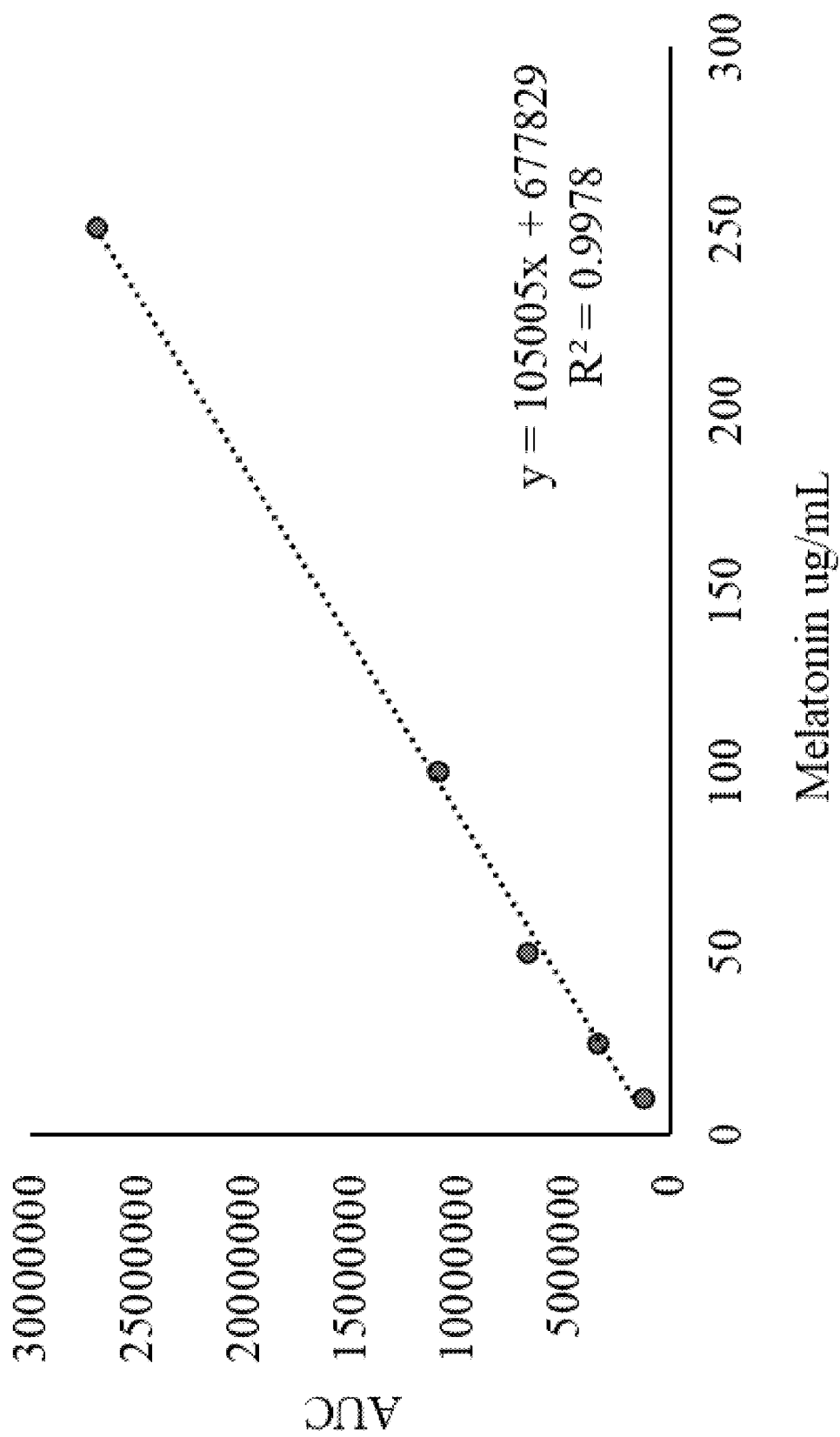
FIG. 5. Calibration curve of melatonin.
Figure 6:
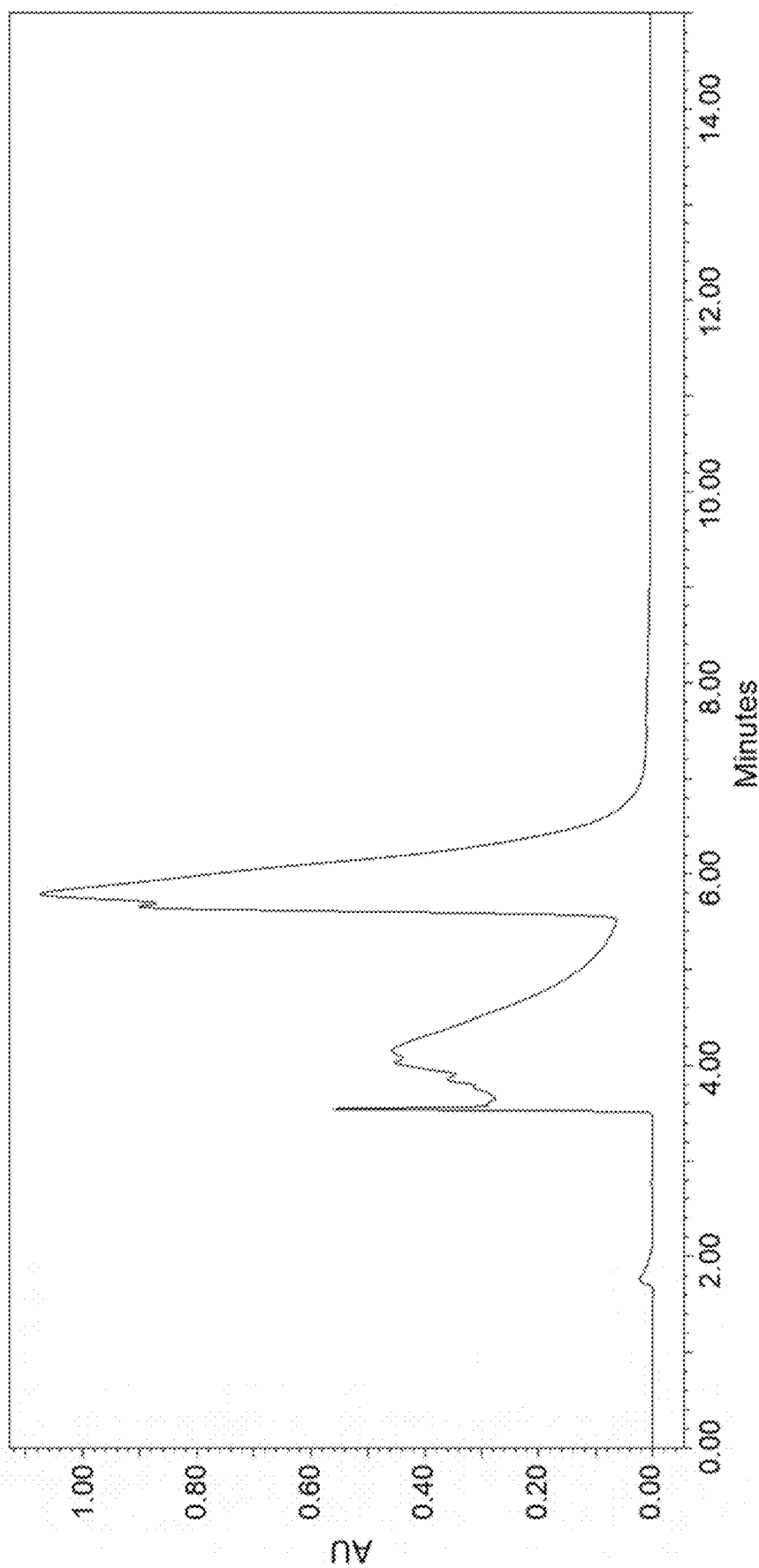
FIG. 6. HPLC chromatogram of CHTL-TAN composite film loaded with melatonin after dissolution in phosphate buffer, recorded at 280 nm.
Figure 7:
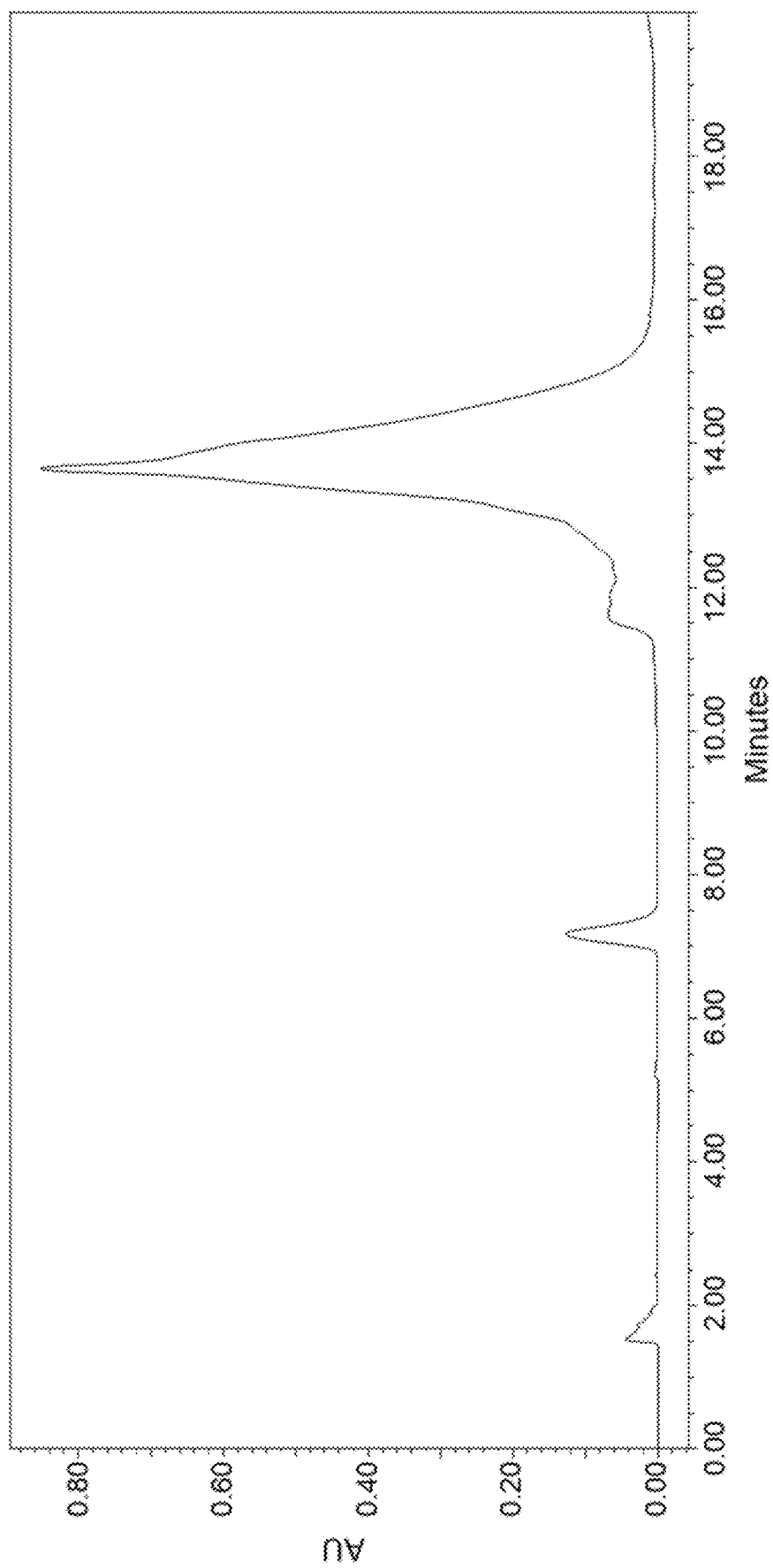
FIG. 7. HPLC chromatogram of CHTL-TAN composite film after dissolution in phosphate buffer, recorded at 280 nm.
Figure 8:
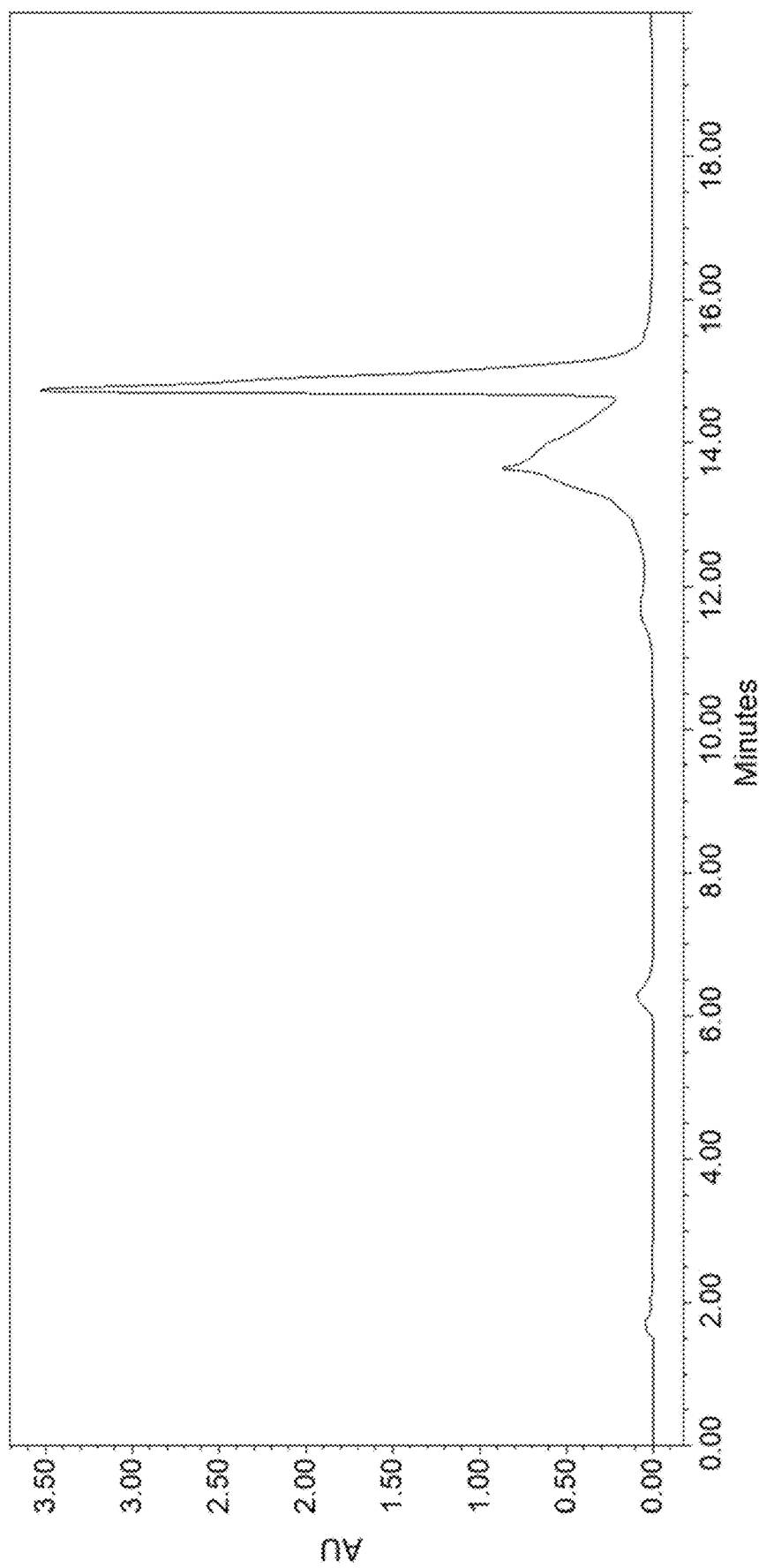
FIG. 8. HPLC chromatogram of CHTL-TAN composite film loaded with melatonin after dissolution in phosphate buffer, recorded at 280 nm.
Figure 9:
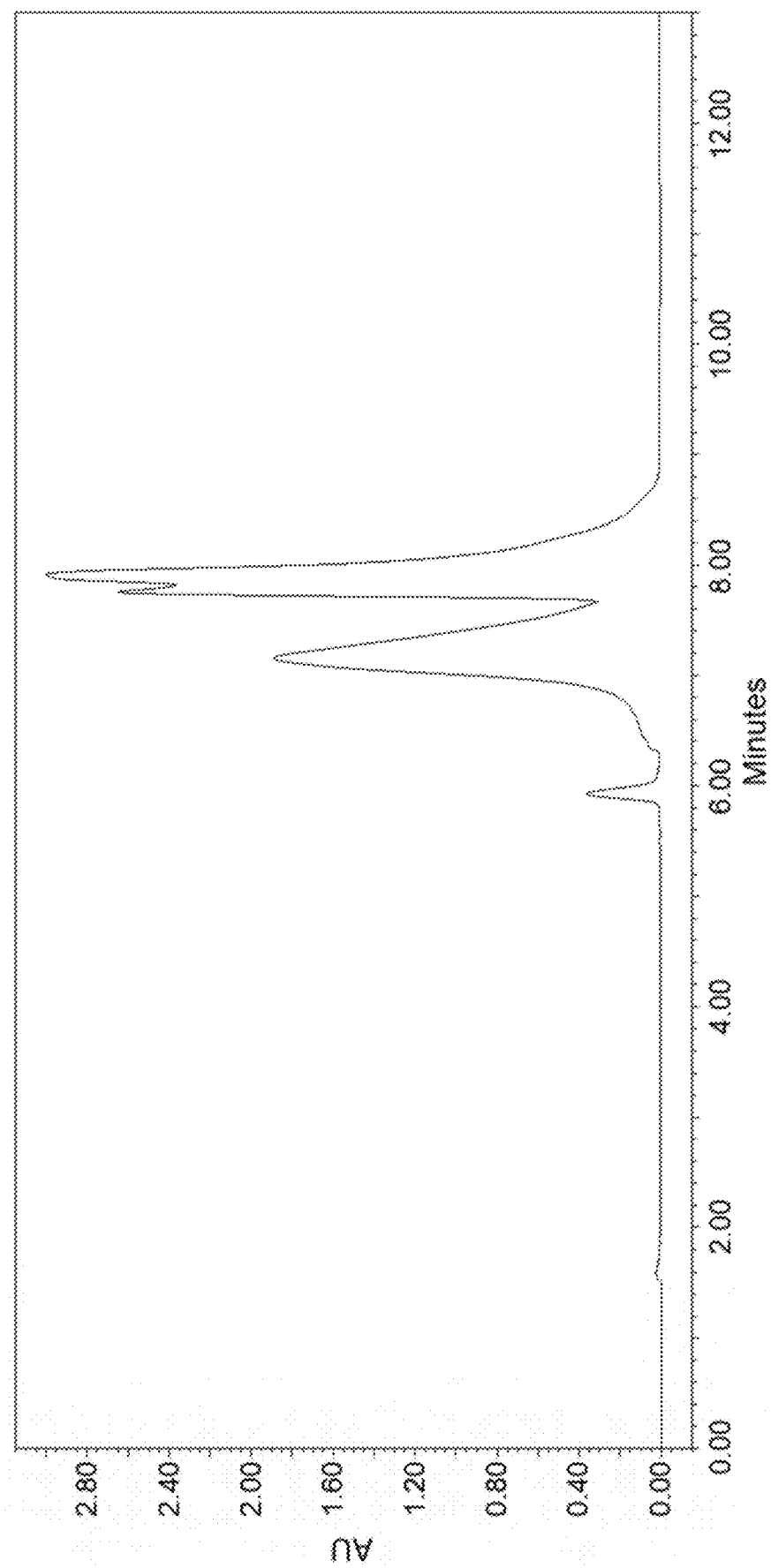
FIG. 9. HPLC chromatogram of CHTL-TAN composite film loaded with melatonin after dissolution, recorded at 280 nm.
Figure 10A:
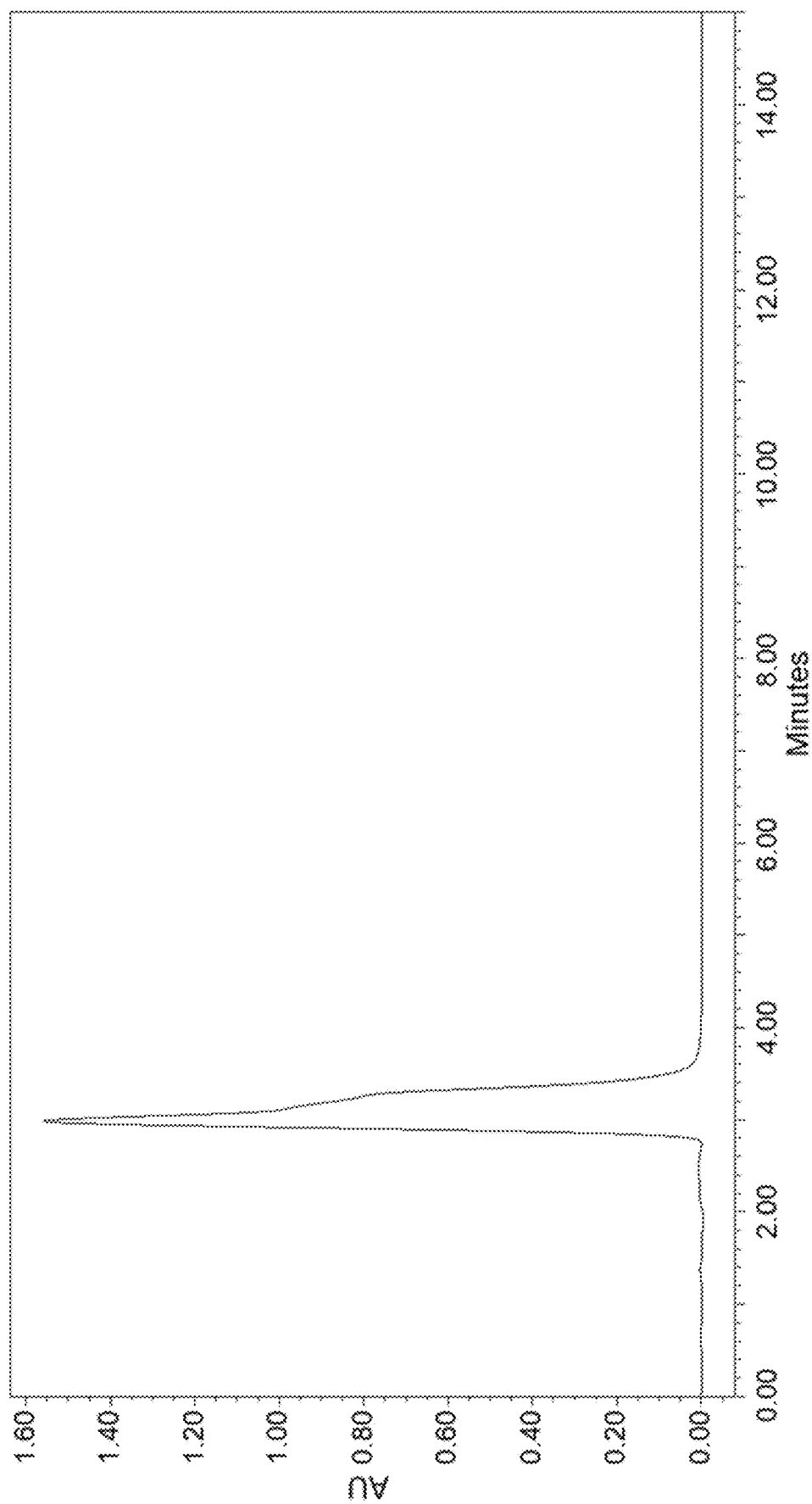
FIG. 10A. HPLC chromatogram of melatonin at 150 µm/mL, recorded at 280 nm.
Figure 10B:
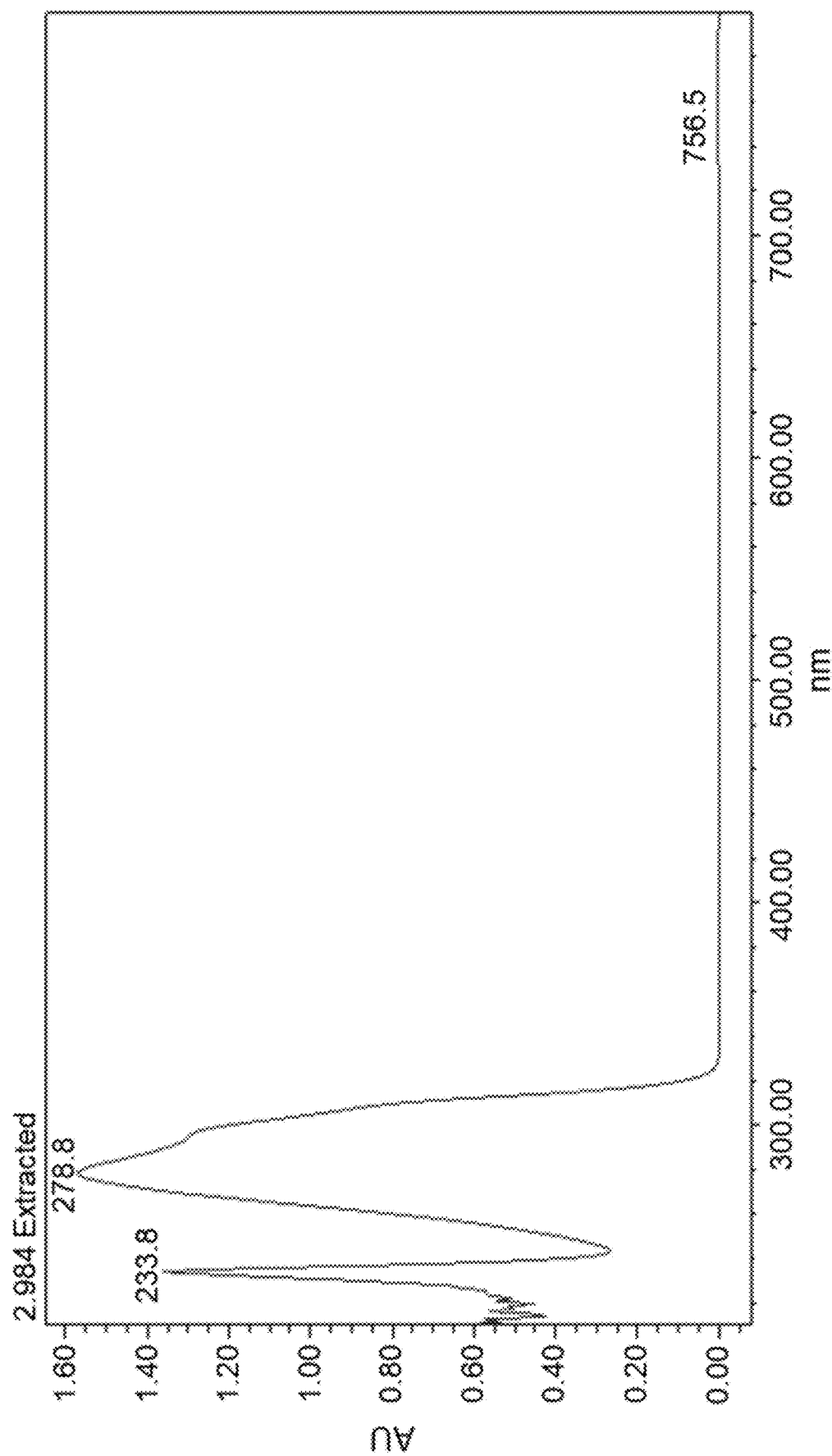
FIG. 10B. UV spectra of melatonin at 150 µm/mL from FIG. 10A.
Figure 11A:
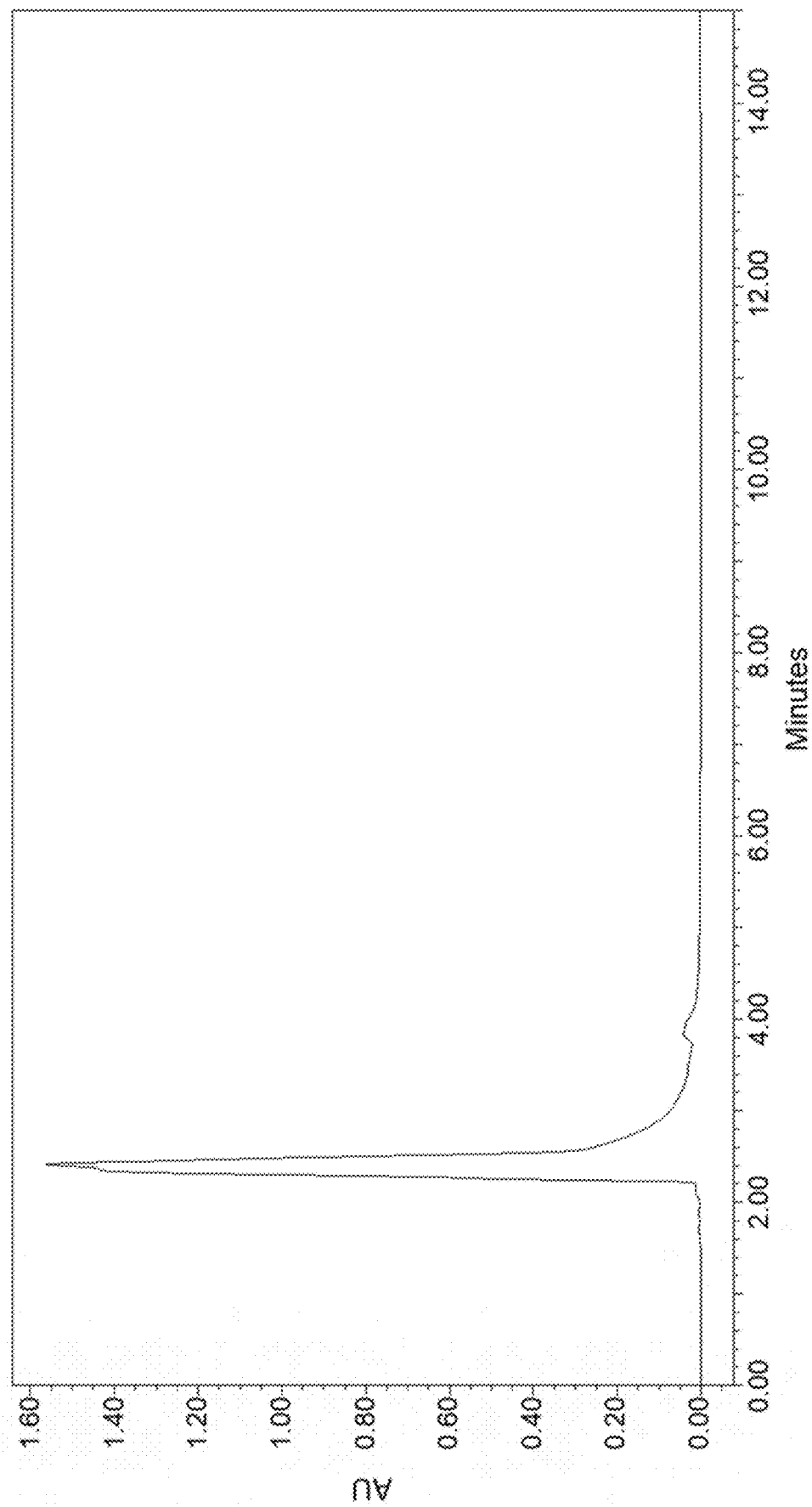
FIG. 11A. HPLC chromatogram of TAN (quebracho) at 200 µg/mL, recorded at 280.
Figure 11B:
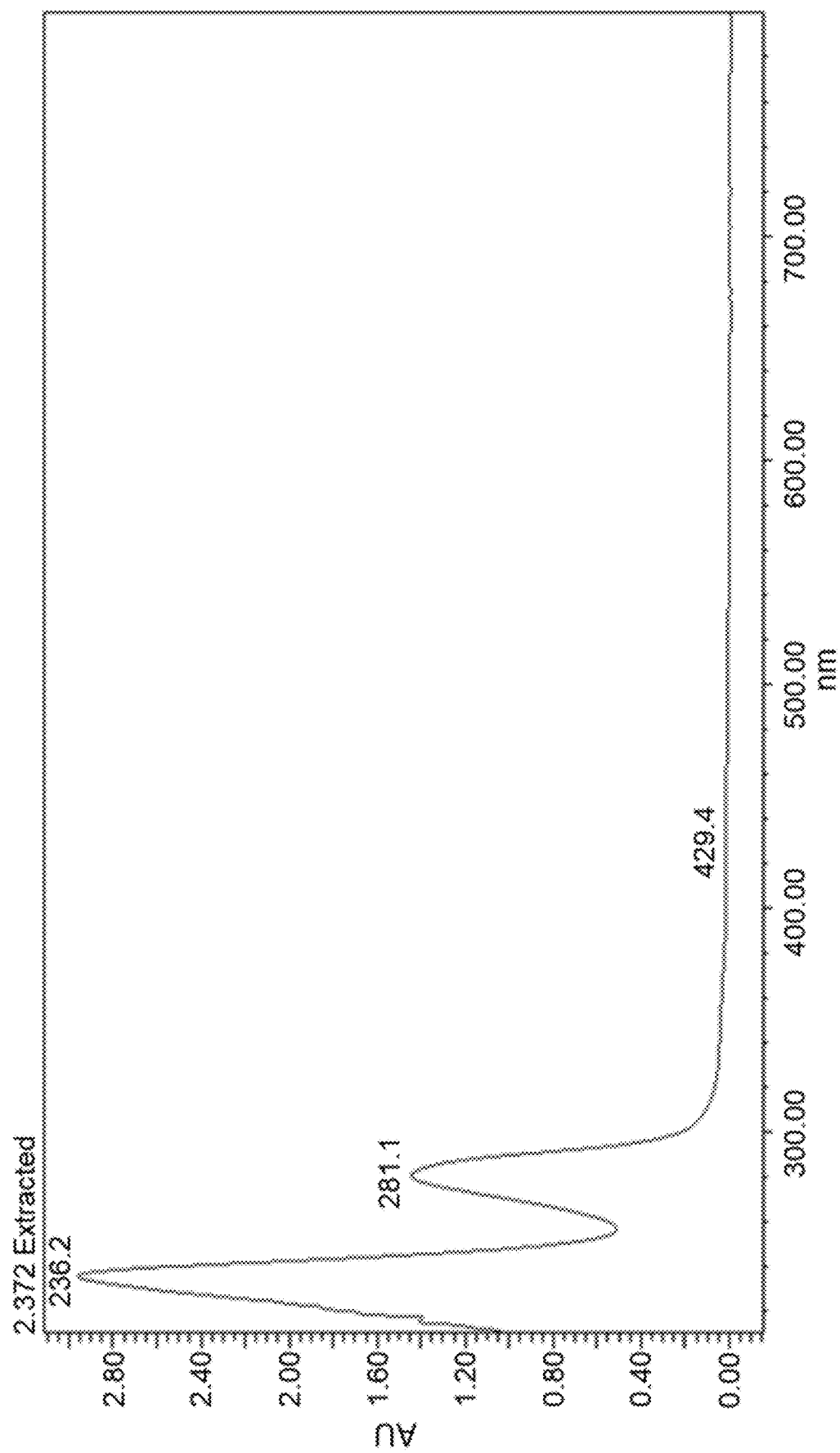
FIG. 11B. UV spectra of the TAN (quebracho) at 200 µm/mL of FIG. 11A.
Figure 12:
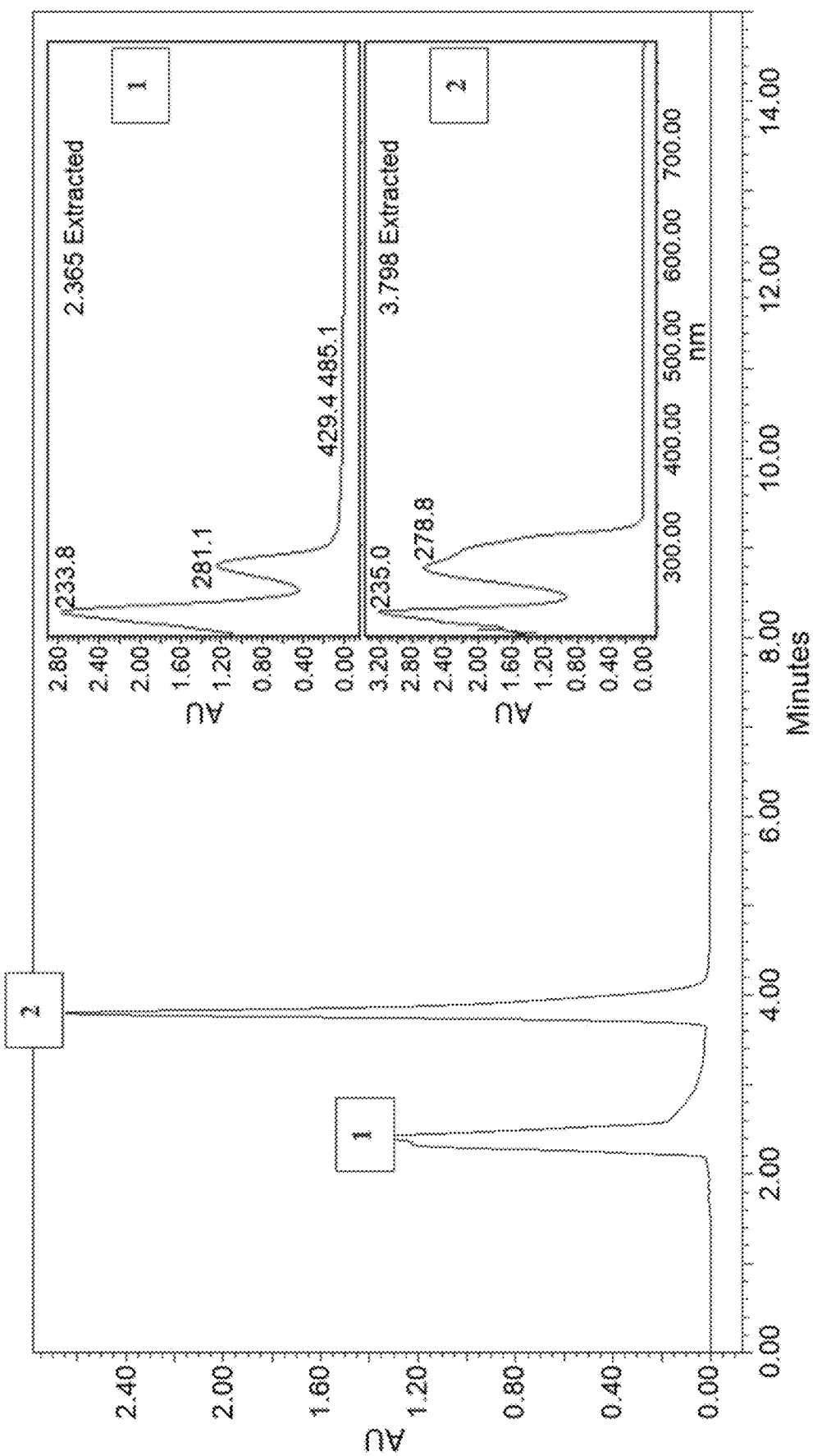
FIG. 12. HPLC chromatogram of TAN (quebracho) at 200 µg/mL and melatonin at 150 µm/mL, recorded at 280 nm. Inserts are the UV spectra.
Figure 13:
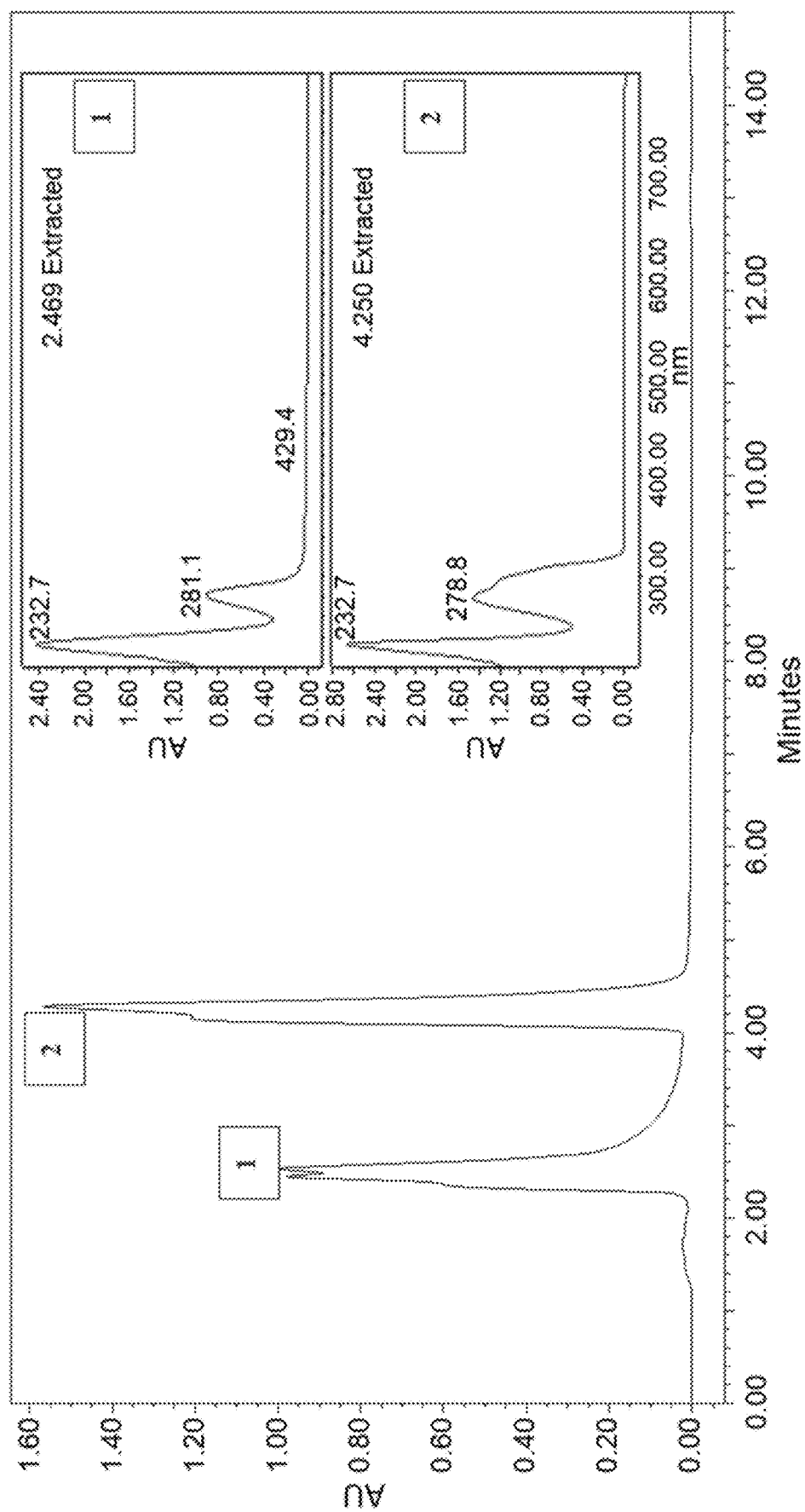
FIG. 13. HPLC chromatogram of CHTL-TAN (Quebracho) at 200 µg/mL and melatonin at 150 µm/mL, recorded at 280 nm. Inserts are the UV spectra.
Figure 14A:
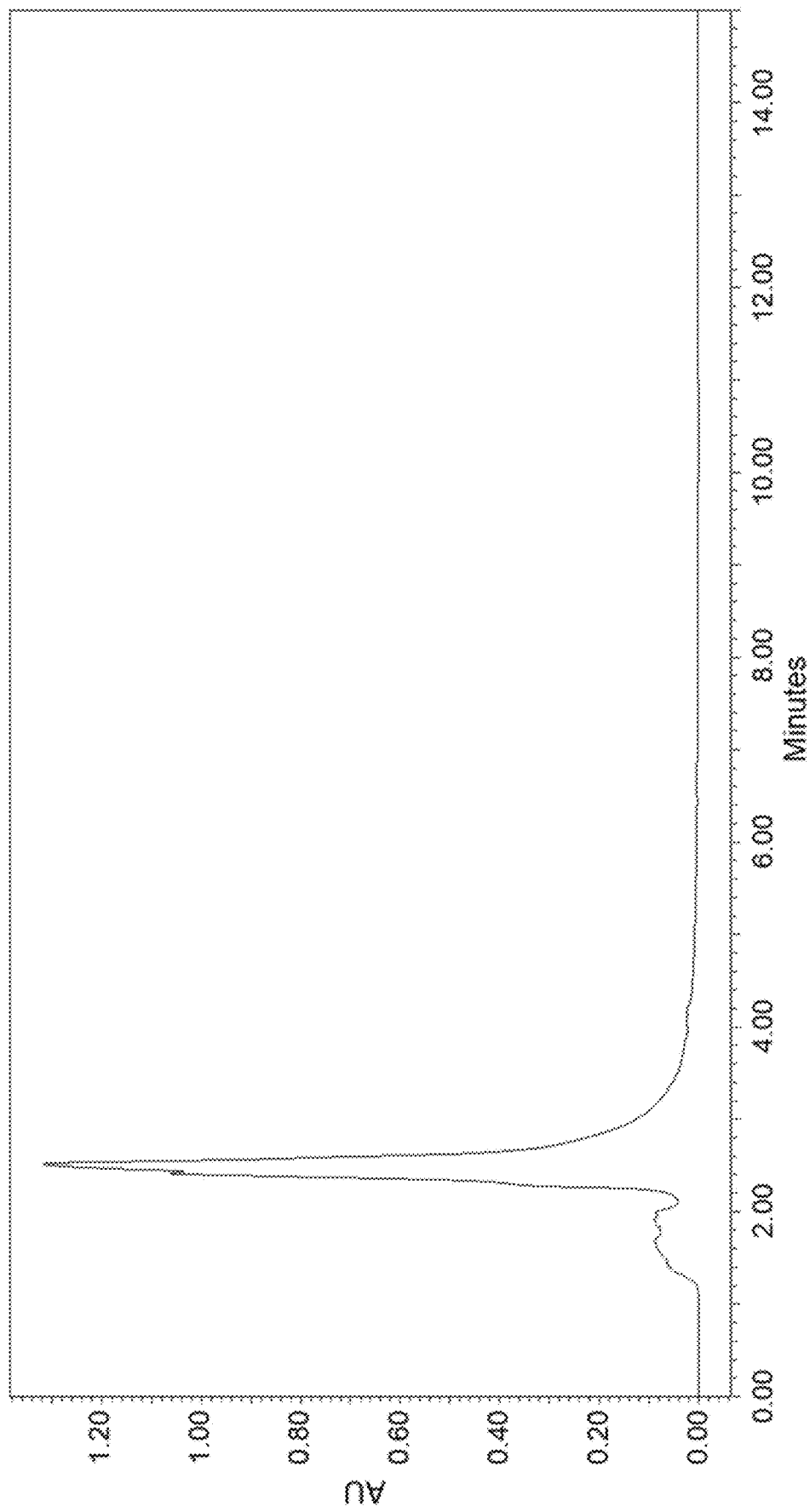
FIG. 14A. HPLC chromatogram of CHTL-TAN (quebracho) composite films after dissolution in water, recorded at 280 nm.
Figure 14B:
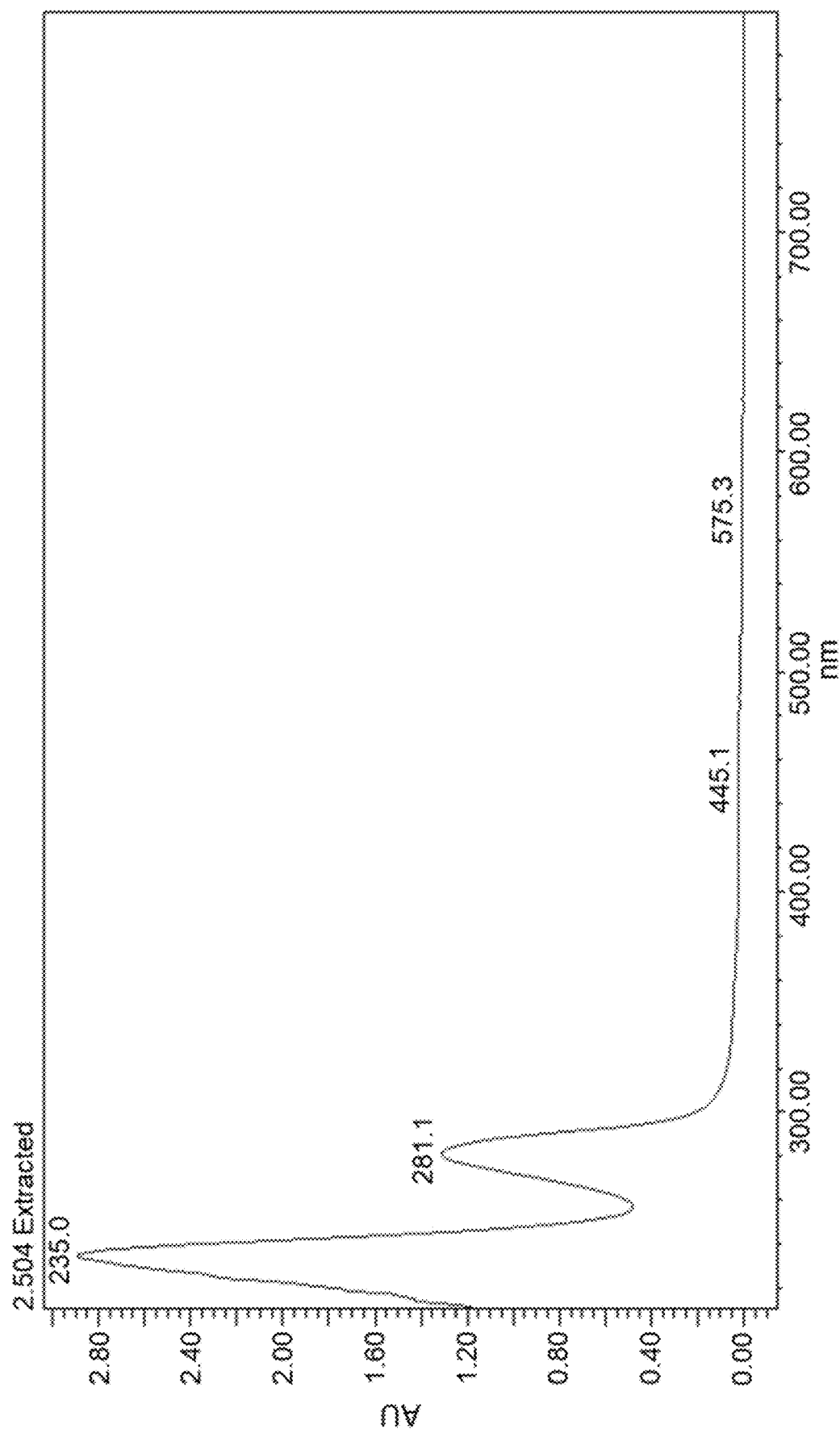
FIG. 14B. UV spectra of peak from FIG. 14A.
Figure 15A:
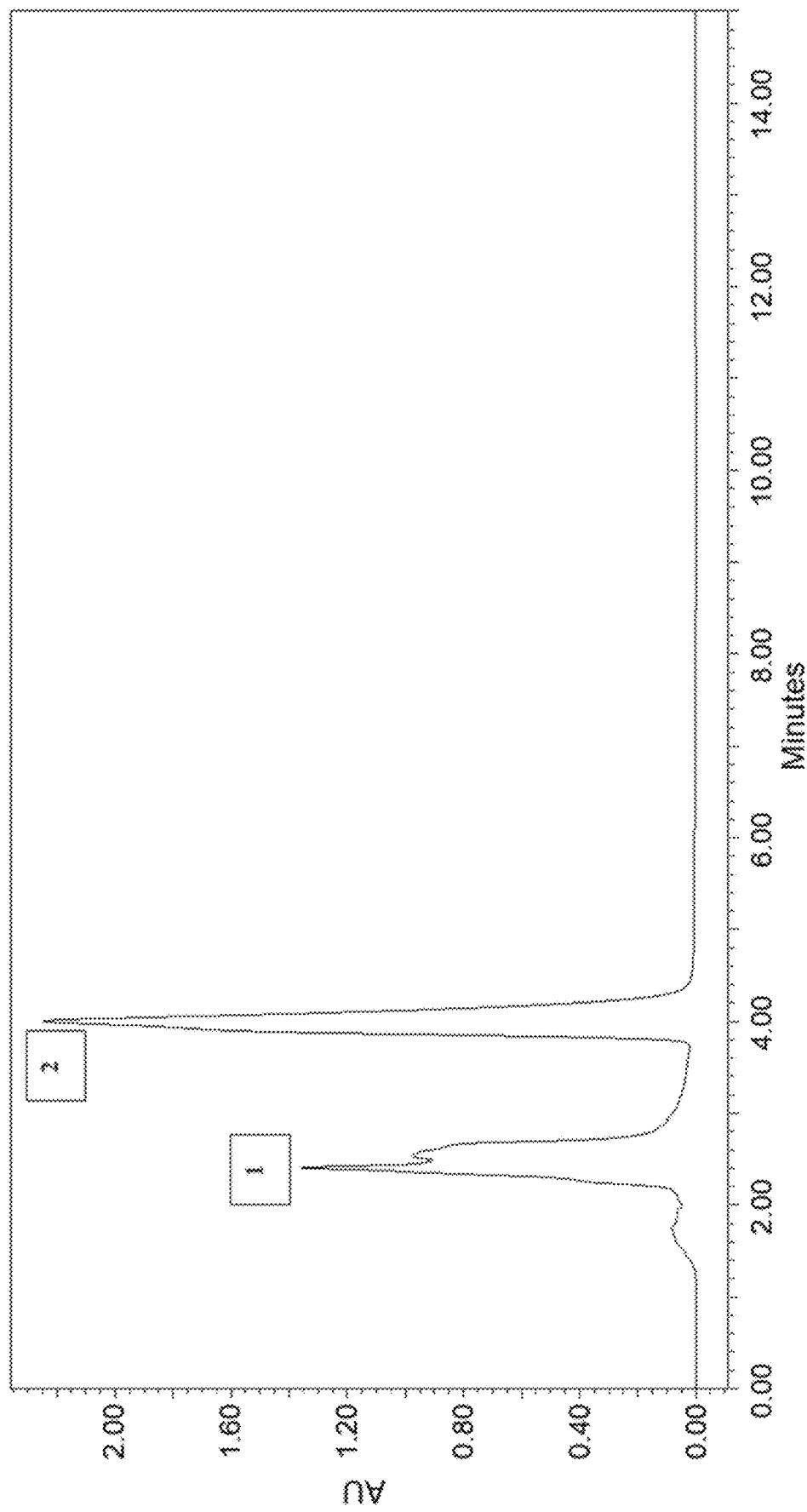
FIG. 15A. HPLC chromatogram of CHTL-TAN (quebracho) composite films loaded with melatonin after dissolution in water, recorded at 280 nm.
Figure 15B:
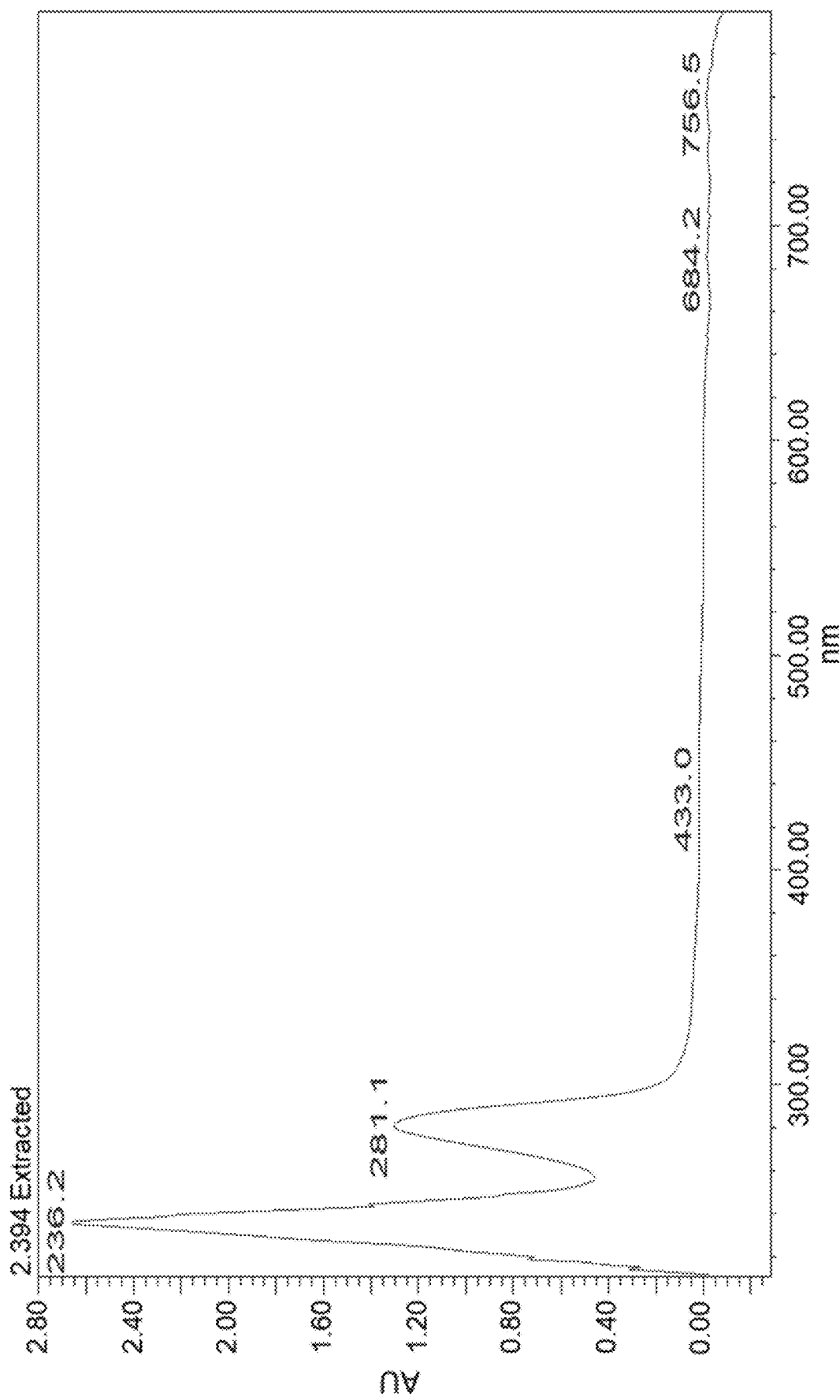
FIG. 15B. UV spectra of Peak 1 from FIG. 15A.
Figure 15C:
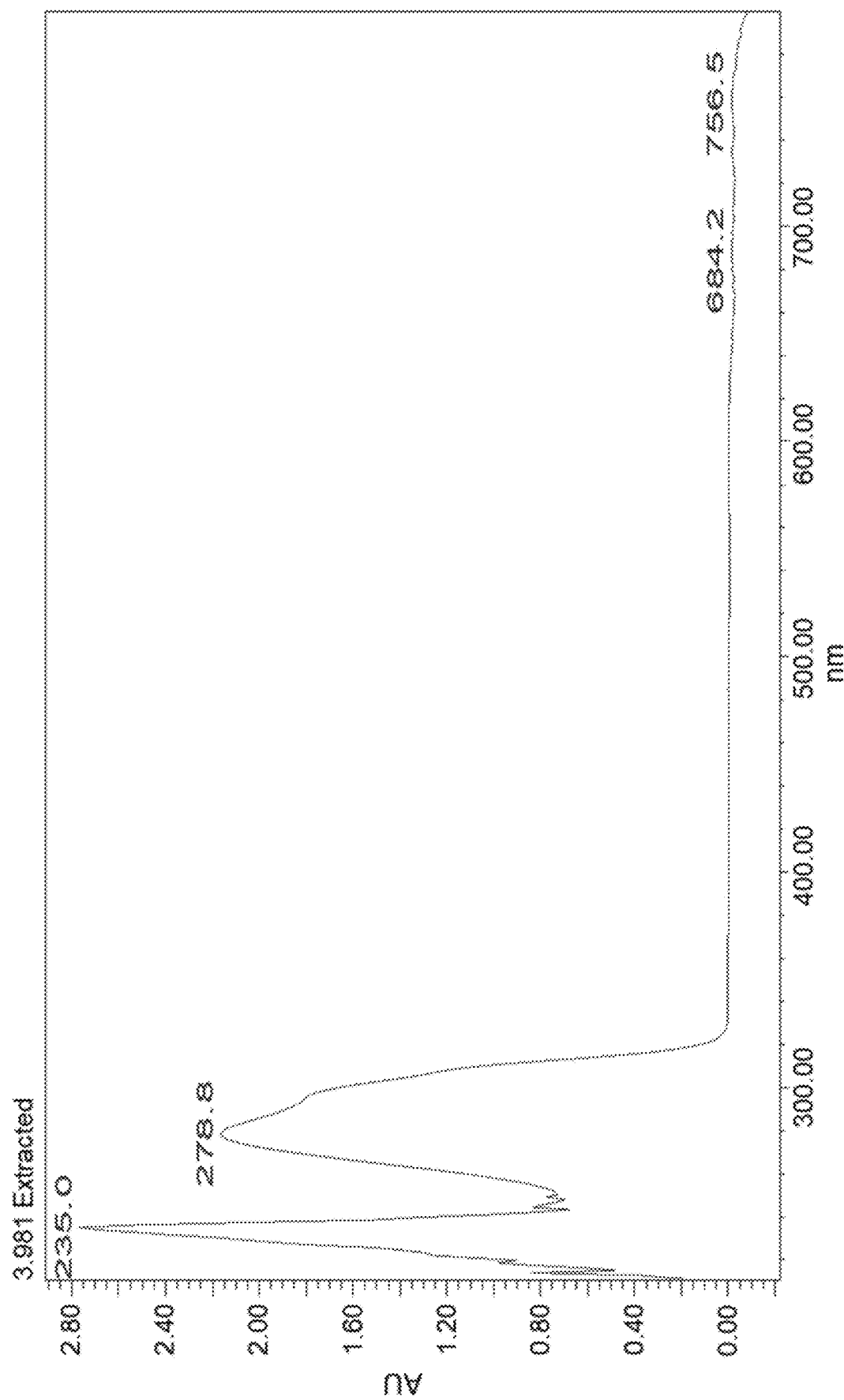
FIG. 15C. UV spectra of Peak 2 from FIG. 15A.
Figure 16:
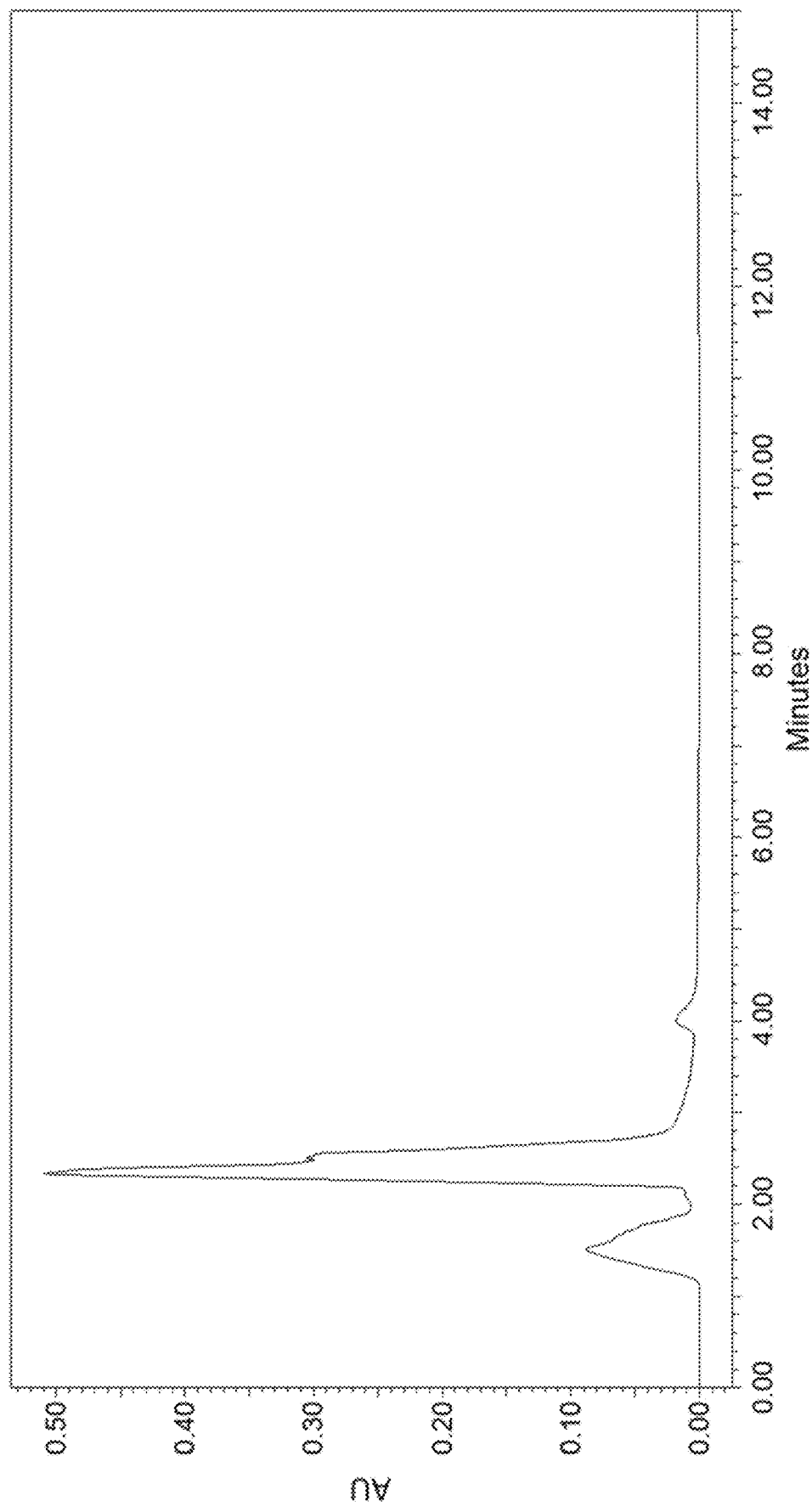
FIG. 16. HPLC chromatogram of CHTL-TAN (GSE) composite film after dissolution in water, recorded at 280 nm.
Figure 17:
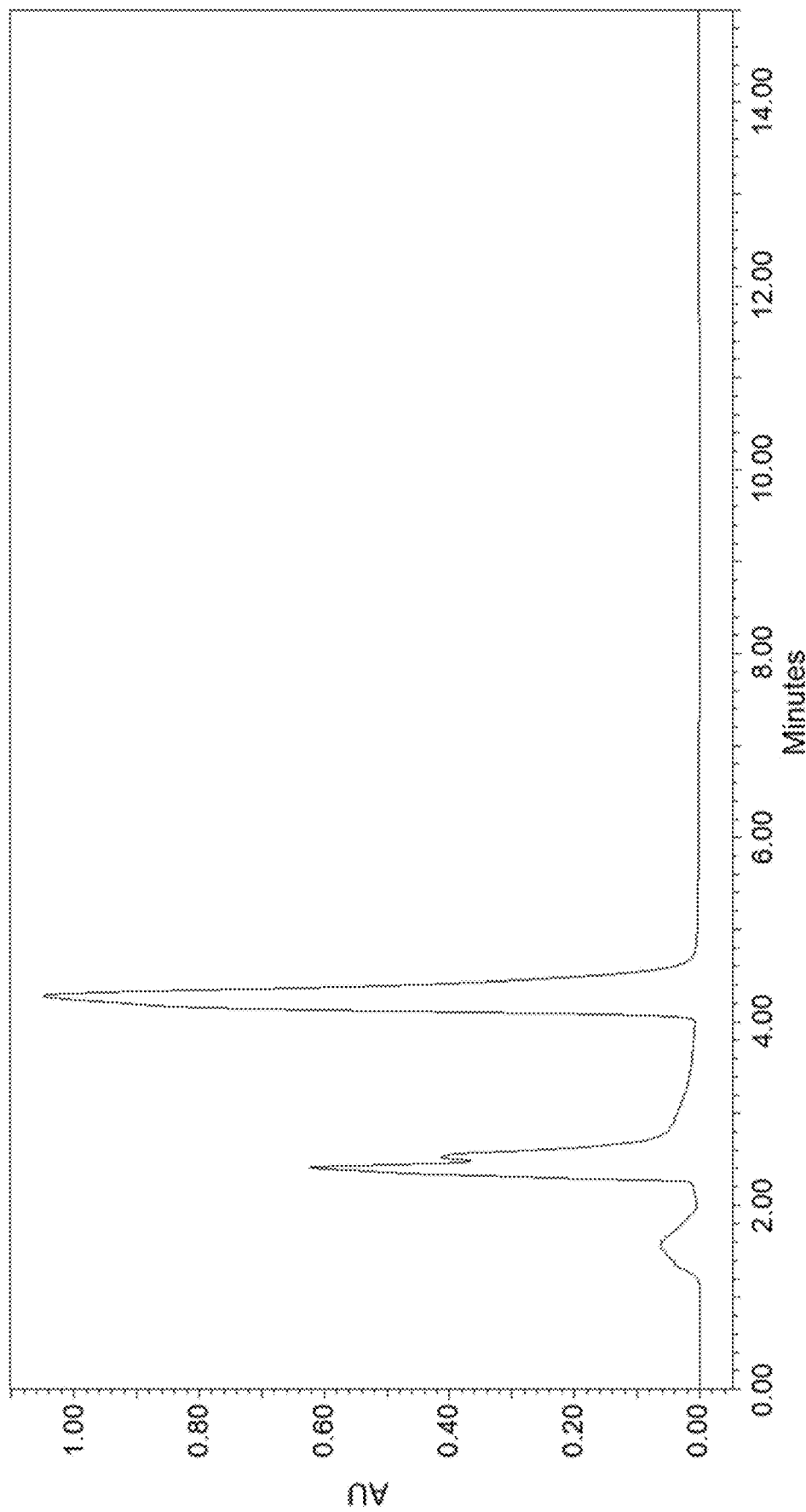
FIG. 17. HPLC chromatogram of CHTL-TAN (GSE) composite film after dissolution loaded with melatonin after dissolution in water, recorded at 280 nm.

The chitosan lactate and grapeseed extract+/−melatonin and the chitosan lactate and cranberry proanthocyanidins+/−melatonin resulted in more desirable film characteristics in that the films were not brittle. (FIG. 1, center and right columns, and FIG. 3). However even these formulations stuck to the silicone molds. It is predicted that the chitosan lactate (pH) drove the interactions with the mold. For this reason, we moved away from both chitosan lactate and sulfonated tannins as present in the quebracho tannin as less desirable ingredients.

Strip Dissolution in Water and Quantification of Melatonin Release

Melatonin-loaded CHTL-TAN films as prepared above were removed from the silicon mold to yield strips of film. Each strip was placed individually in a beaker containing 10 mL of dd water and submitted to a slight stirring (100 rpm). Dissolution time was defined as the time at which the strip started to disappear. Results are shown in Table 5.

TABLE 5

| CHTL-TAN Film | Dissolution Time (min) |
|---|---|
| CHTL-TAN (quebracho) | 4 |
| CHTL-TAN (quebracho) with melatonin | 5 |
| CHTL-TAN (GSE) | 3 |
| CHTL-TAN (GSE) with melatonin | 3 |

The released melatonin after dissolution was quantified. After dissolution of the film, an aliquot of the sample (200 ul) was taken, and the concentration of the released melatonin was determined by HPLC-DAD. The HPLC solvents employed were 0.1% (v/v) trifluoroacetic acid/water (solvent A) and 0.1% (v/v) acetonitrile (solvent B). Results are shown in FIGS. 10-17. Comparisons are shown in FIGS. 4-9.

Melatonin Loading of the CHTL-TAN Composite Films—Effect of pH

A stock solution of chitosan lactate (CHTL) (>95.0% deacetylated, Product No. AL-10131, Lot No. 22022) at 10 mg/mL was prepared in water. Stock solutions of tannin (TAN) (grape seed extract (GSE), TAN'ACTIVE GUT, Batch: 010417, Silvateam, Wilton, CT) at 10 mg/mL was prepared in ethanol. A stock solution of melatonin at 50.0 mg/mL was prepared in ethanol. CHTL-TAN composite solutions were prepared as follows: First, the pH of the CHT solution was adjusted to 4.0, 5.0, or 5.5 100 mg/mL sodium acetate. Then, TAN stock solution was added to the CHTL stock solution under continuous stirring for 10 min at a weight ratio of 90:10 (CHTL:TAN). Then, the melatonin solution was added to the mixture while stirring continuously. Volumes of 30 mL of the CHTL-TAN composite solutions were added to a silicon mold (7.9×5.6×2.5 cm). The samples were placed in an oven at 36° C. for 3 days. See Table 6.

TABLE 6

| | Chitosan Lactate (CHTL) | | | Tannin (TAN) | | | Melatonin | | |
|---|---|---|---|---|---|---|---|---|---|
| | Conc. (mg/mL) | Vol. (mL) | Total (mg) | Conc. (mg/mL) | Vol. (mL) | Total (mg) | Conc. (mg/mL) | Vol. (mL) | Total (mg) |
| CHTL:TAN (90:10) 0 mg of Melatonin pH 4.0 | 10.0 | 27.0 | 270.0 | 10.0 | 3.0 | 30.0 | 50.0 | 0 | 0 |
| CHTL:TAN (90:10) 22.6 mg of Melatonin pH 4.0 | 10.0 | 27.0 | 270.0 | 10.0 | 3.0 | 30.0 | 50.0 | 0.452 | 22.6 |
| CHTL:TAN (90:10) 0 mg of Melatonin pH 5.0 | 10.0 | 27.0 | 270.0 | 10.0 | 3.0 | 30.0 | 50.0 | 0 | 0 |
| CHTL:TAN (90:10) 22.6 mg of Melatonin pH 5.0 | 10.0 | 27.0 | 270.0 | 10.0 | 3.0 | 30.0 | 50.0 | 0.452 | 22.6 |
| CHTL:TAN (90:10) 0 mg of Melatonin pH 5.5 | 10.0 | 27.0 | 270.0 | 10.0 | 3.0 | 30.0 | 50.0 | 0 | 0 |
| CHTL:TAN (90:10) 22.6 mg of Melatonin pH 5.5 | 10.0 | 27.0 | 270.0 | 10.0 | 3.0 | 30.0 | 50.0 | 0.452 | 22.6 |

All films were fragile, and they are stuck to the silicone mold. It was impossible to extract the films without breaking them. This was likely the result of the chitosan lactate. This experiment was focused on GSE. We eliminated quebracho tannins because they were not a good tannin source. The use of GSA with chitosan lactate was better but still resulted in fragile films, again, likely due to the chitosan lactate.

Example 3

Psilocybin-Loaded Chitosan-Tannin Composite Films

The objective of this example was to show that psilocybin can be incorporated into chitosan-tannin composite hydrogel solutions, cast into molds, form stable flexible thin films after drying, and release psilocybin upon dissolution in water.

Chitosan-Tannin (CHT-TAN) Psilocybin Films

A stock solution of chitosan (CHT) (>98.0% deacetylated, Product No. C-M-95-401132, Lot No. 351821, ChitoLytic, Ontario, Canada) at 10 mg/mL was prepared in acetic acid (0.5% v/v). A stock solution of tannin (TAN) (grape seed extract (GSE), TAN'ACTIVE GUT, Batch: 010417, Silvateam, Wilton, CT) at 10 mg/mL was prepared in ethanol. CHT-TAN composite solutions were prepared as follows: TAN stock solution was added to the CHT stock solution under continuous stirring for 10 min at a weight ratio of 10-90 TAN to CHT. Then, psilocybin solutions (see below) were added to the mixture while stirring continuously. Volumes of 30 mL of the CHT-TAN solutions with or without psilocybin was added to a silicon mold (7.9×5.6×2.5 cm). The samples were placed in an oven at 36° C. for 72 hours. See Table 7.

Column: Acclaim120 C8, 5 μm, 250×4.6 mm+appropriate pre-column
Column Temperature: Controlled at 25° C.
Injection Volume: 10 μL
Flow Rate: 1.0 mL/min
Run Time: 16 min
Mobile Phase: 95% Solvent A (1% (v/v) acetic acid)+5% Solvent B (Ethanol)
Technique: Isocratic Elution
Detector Wavelength: 269 nm
Calculations: The HPLC raw data was reported in mg/mL psilocybin in the diluted assay solution. This value was converted to % (w/w) psilocybin in the original formulation using the following calculation where Vol. is the volume of the volumetric flask in which the assay sample was diluted, Mass is the sample mass that is added to the volumetric flask, and Raw Conc. is the HPLC result.

Equation: Final Conc. % (w/w)=Raw Conc. (mg/mL)*Vol. (mL)/Mass (mg)*100%.

Example calculation: Psilocybin 100% (w/w)=0.05 mg/mL*100 mL/5 mg*100%.

Acceptance criteria: The correlation coefficient of the standard curve must be ≥0.995.

A psilocybin reference standard was analyzed by HPLC-DAD method. Results showed that psilocybin elutes at 6.0 minutes.

A CHT-TAN placebo solution (without psilocybin) was analyzed by HPLC-DAD method. Results showed placebo peaks at 1.8, 6.5 and 24.7 minutes.

A CHT-TAN placebo solution spiked with psilocybin (0.01 mg/mL) was analyzed by HPLC-DAD method.

TABLE 7

|  | Chitosan Lactate (CHTL) | | | Tannin (TAN) | | | Psilocybin |
| --- | --- | --- | --- | --- | --- | --- | --- |
|  | Conc. (mg/mL) | Vol. (mL) | Total (mg) | Conc. (mg/mL) | Vol. (mL) | Total (mg) | Total (mg) |
| Film 1 CHTL-TAN-Psilocybin 0 mg Psilocybin | 10.0 | 27.0 | 270.0 | 10.0 | 3.0 | 30.0 | 0 |
| Film 2 CHTL-TAN-Psilocybin 7.6 mg Psilocybin | 10.0 | 27.0 | 270.0 | 10.0 | 3.0 | 30.0 | 7.6 |
| Film 3 CHTL-TAN-Psilocybin 9 mg Psilocybin | 10.0 | 27.0 | 270.0 | 10.0 | 3.0 | 30.0 | 9 |
| Film 4 CHTL-TAN-Psilocybin 20 mg Psilocybin | 10.0 | 27.0 | 270.0 | 10.0 | 3.0 | 30.0 | 20 |
| Film 5 CHTL-TAN-Psilocybin 20 mg Psilocybin | 10.0 | 27.0 | 270.0 | 10.0 | 3.0 | 30.0 | 20 |

Figure 18:
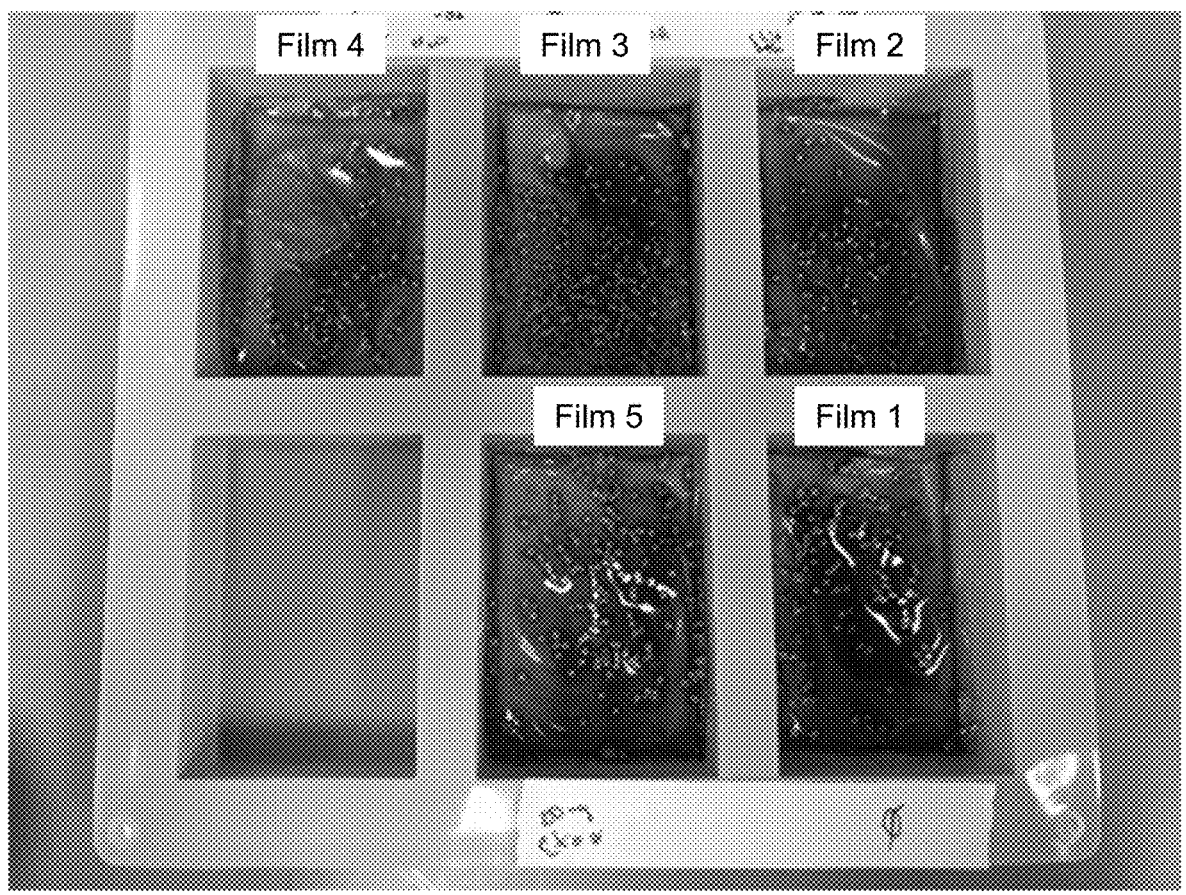
FIG. 18: Chitosan-tannin (CHT-TAN) films with or without psilocybin.

Psilocybin for Film 2 was dissolved in 200 μL of ethanol. Psilocybin for Film 3 was dissolved in 400 μL of CHT-TAN solution. Psilocybin for Film 4 was dissolved in 200 of high purity water. Psilocybin for Film 5 was dissolved in 200 μL of ethanol. Films 1-5 are shown in FIG. 18.

Chitosan-Tannin (CHT-TAN) Psilocybin Film Dissolution

The films were each placed in a beaker containing 50 mL of dd-water or 50 mL of 5% ethanol and 1% acetic acid in water and submitted to a slight stirring (100 rpm). After dissolution, the concentration of psilocybin in solution was determined by HPLC-DAD.

HPLC method: Samples are analyzed on an analytical HPLC with the following conditions.

Results showed the psilocybin peak (5.9 minutes) separates and is identifiable from placebo peaks at 1.8, 6.5 and 24.7 minutes.

Figure 19A:
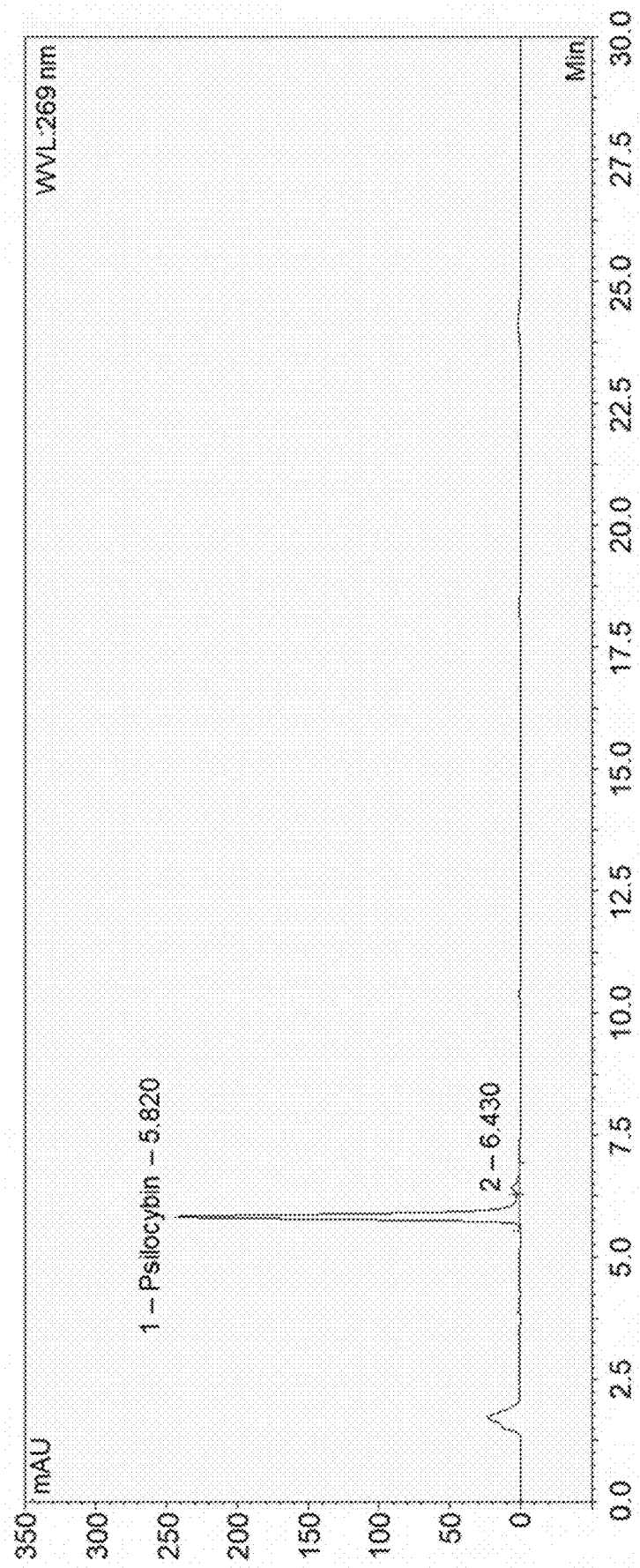
FIG. 19A: Chitosan-tannin (CHT-TAN) film with 7.6 mg psilocybin (Film 2) diluted in water.
Figure 19B:
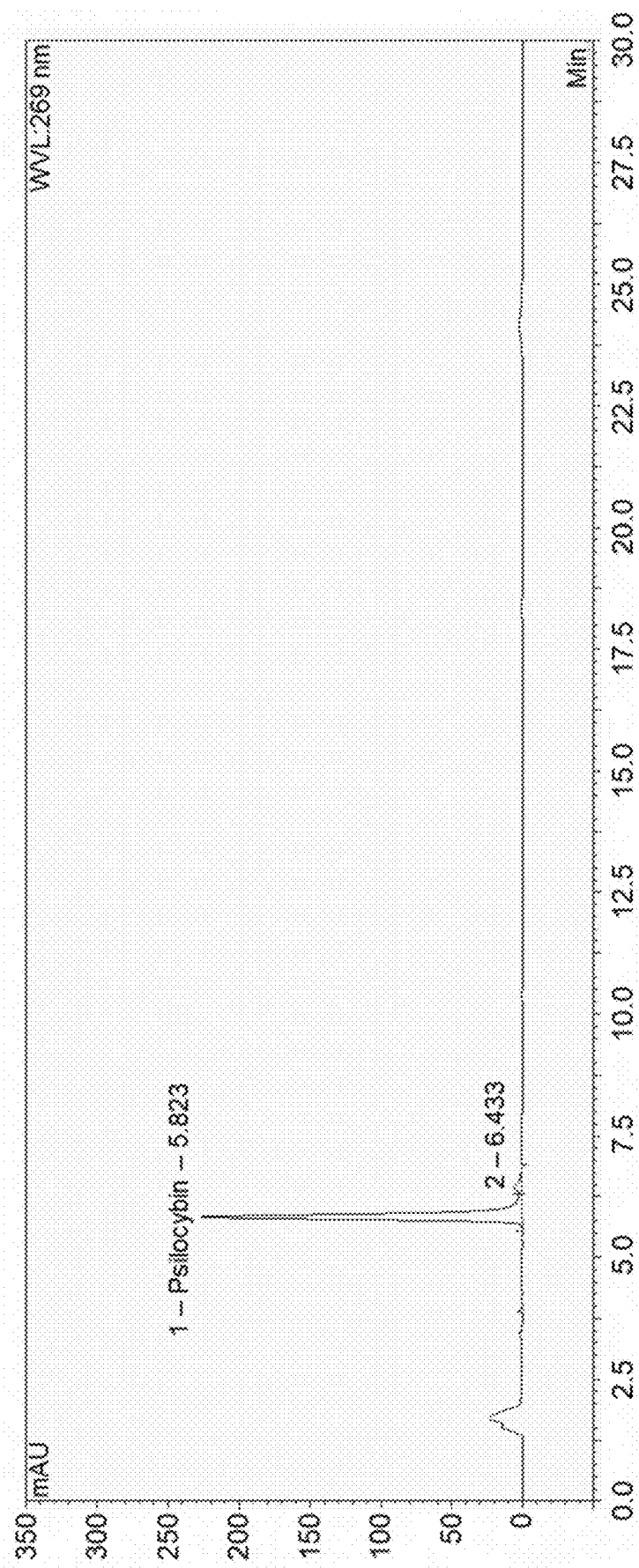
FIG. 19B: Chitosan-tannin (CHT-TAN) film with 7.6 mg psilocybin (Film 2) diluted in mobile phase.
Figure 20A:
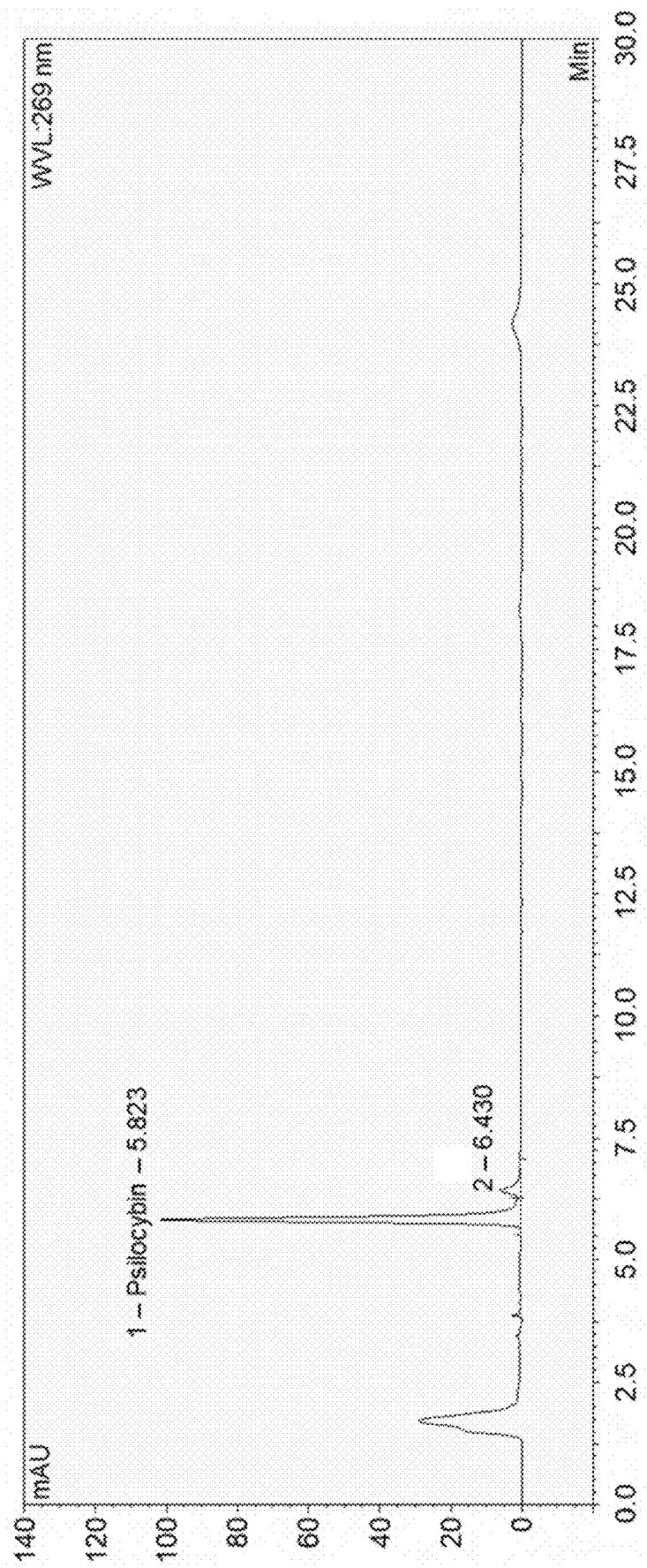
FIG. 20A: Chitosan-tannin (CHT-TAN) film with 9 mg psilocybin (Film 3) diluted in water.
Figure 20B:
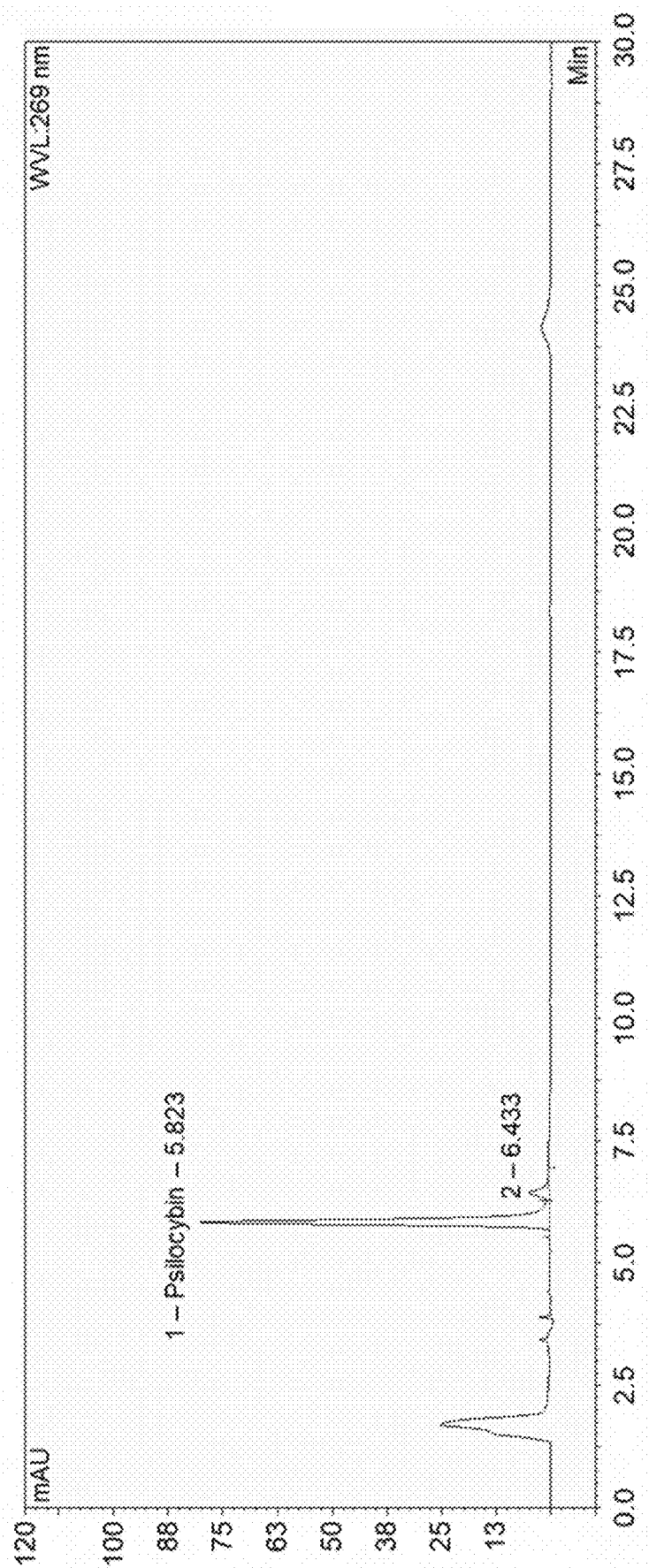
FIG. 20B: Chitosan-tannin (CHT-TAN) film with 9 mg psilocybin (Film 3) diluted in mobile phase.
Figure 21A:
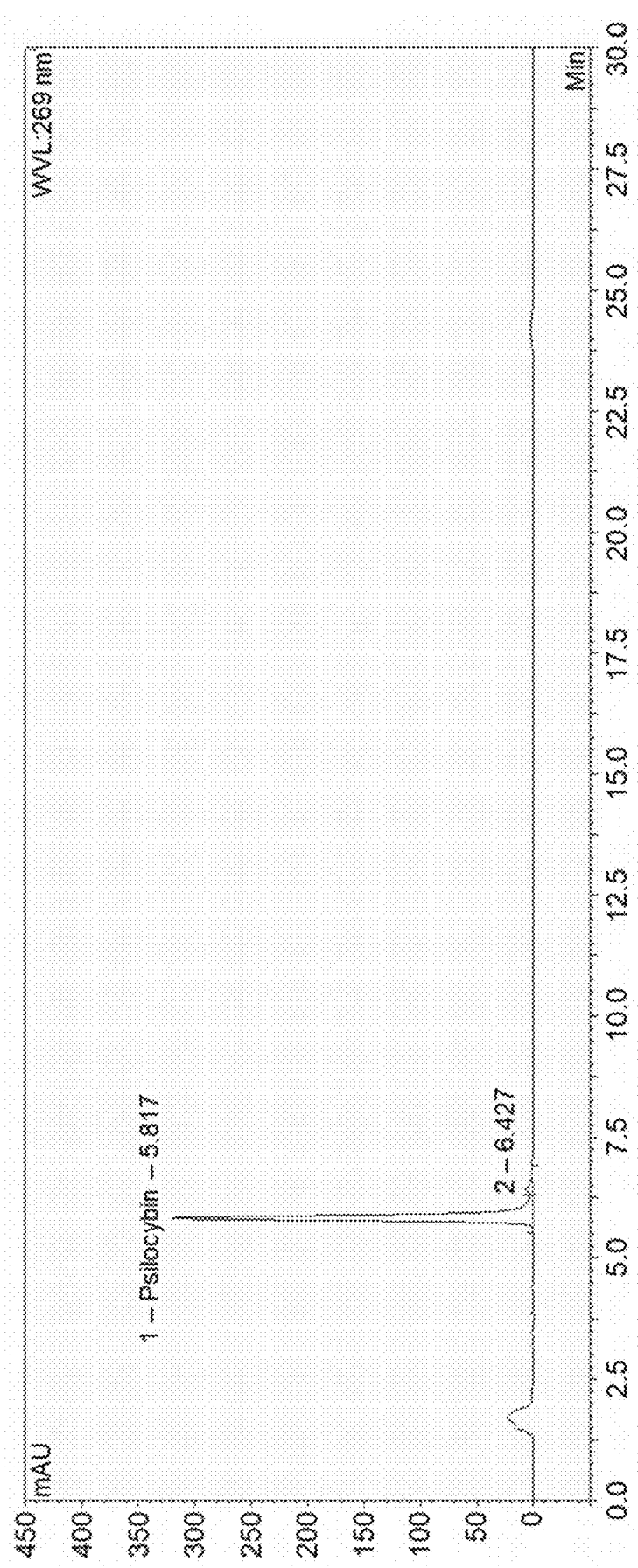
FIG. 21A: Chitosan-tannin (CHT-TAN) film with 20 mg psilocybin (Film 4) diluted in water.
Figure 21B:
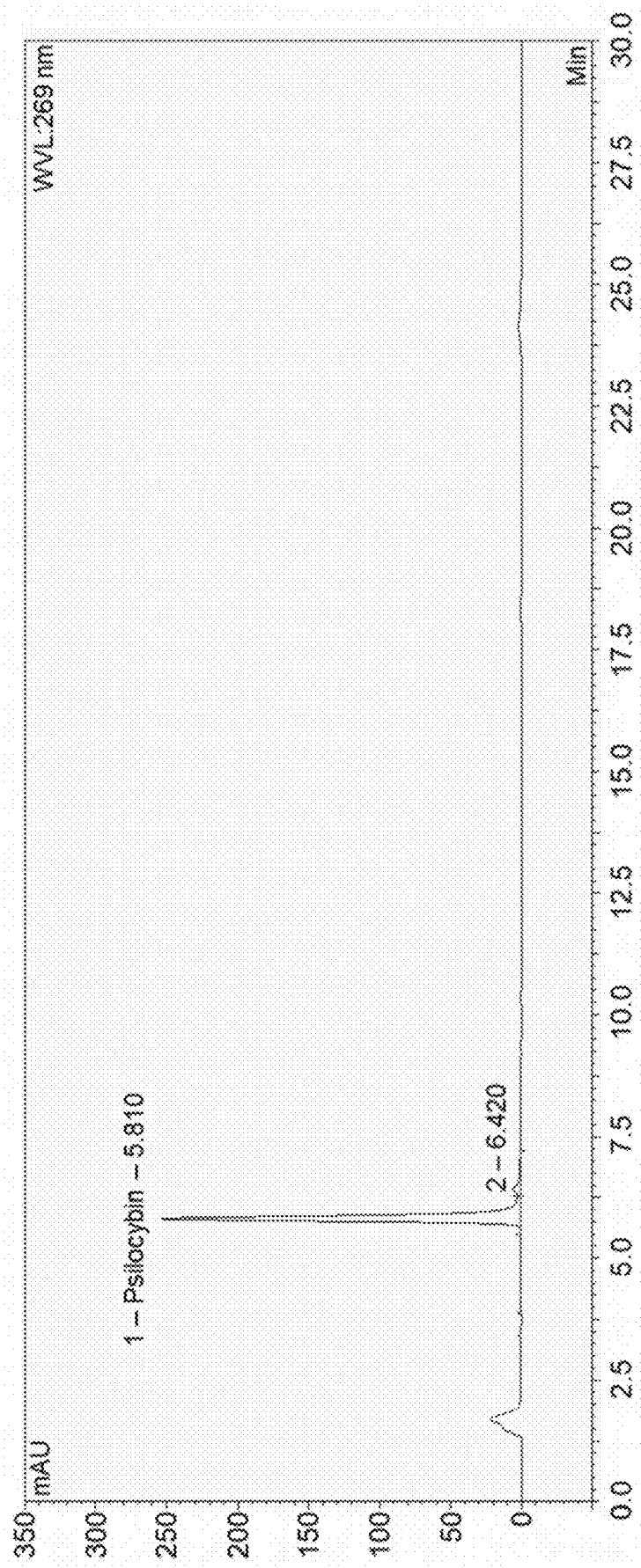
FIG. 21B: Chitosan-tannin (CHT-TAN) film with 20 mg psilocybin (Film 4) diluted in mobile phase.
Figure 22A:
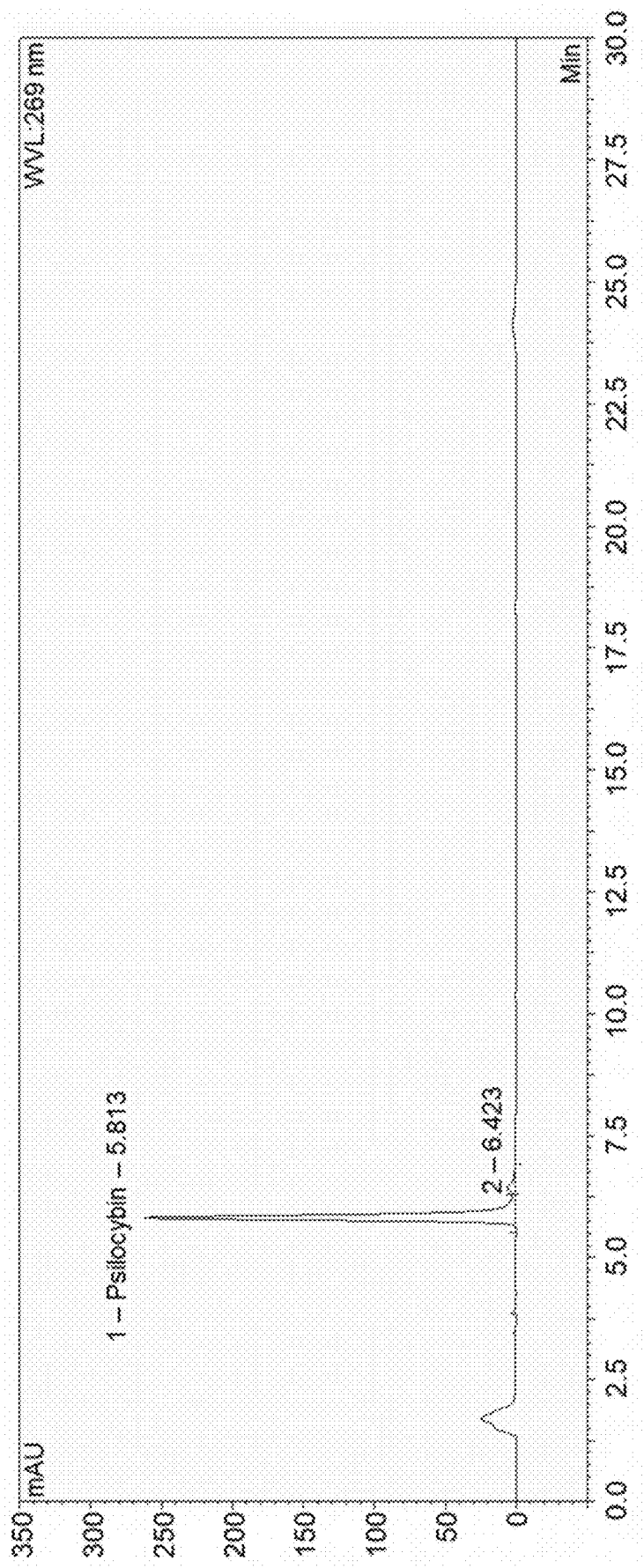
FIG. 22A: Chitosan-tannin (CHT-TAN) film with 20 mg psilocybin (Film 5) diluted in water.
Figure 22B:
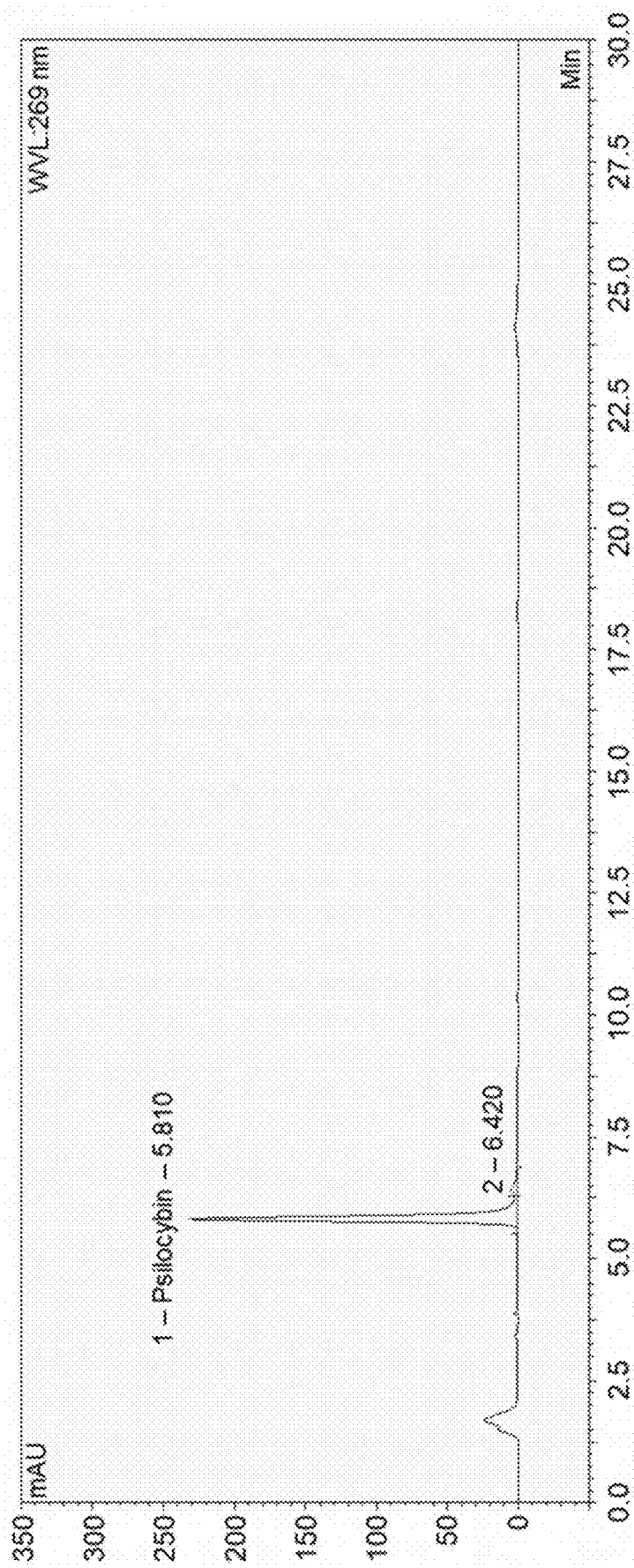
FIG. 22B: Chitosan-tannin (CHT-TAN) film with 20 mg psilocybin (Film 5) diluted in mobile phase.

HPLC results for Film 2 (7.6 mg psilocybin) are shown in FIGS. 19A and 19B. HPLC results for Film 3 (9 mg psilocybin) are shown in FIGS. 20A and 20B. HPLC results for Film 4 (20 mg psilocybin) are shown in FIGS. 21A and 21B. The results show the psilocybin peak (5.8 minutes) separates and is identifiable and quantifiable from closest placebo peak at 6.4 minutes The theoretical amount of psilocybin loaded into Film 4 was 20 mg, and the recovery of psilocybin in the dissolved solution from Film 4 as determined by HLPC was 20.3 mg. HPLC results for Film 5 (20 mg psilocybin) are shown in FIGS. 22A and 22B. The results show the psilocybin peak (5.8 minutes) separates and is identifiable and quantifiable from closest placebo peak at 6.4 minutes The theoretical amount of psilocybin loaded into Film 5 was 20 mg, and the recovery of psilocybin in the dissolved solution from Film 5 as determined by HLPC was 18.2 mg.

Conclusions

Psilocybin (dissolved in water or ethanol) can be incorporated into chitosan-tannin hydrogel solutions, cast into molds, and dried to create a flexible thin film. The film can be dissolved in water (<5 minutes). Psilocybin is released and recovery is 101% with the film in which psilocybin was initially dissolved in water and 91% with the film in which psilocybin was initially dissolved in ethanol. We predict it is possible to solubilize the tannin ingredient in an aqueous ethanol (e.g. 50%, 40%, 30% v/v) solution as opposed to 100% ethanol. We predict it is possible to dry the films as a higher temperature for shorter time duration.

Example 4

Serotonin-Loaded Chitosan-Tannin Composite Films

Serotonin Loading of CHT-TAN Composite Films

A stock solution of chitosan (CHT) (>98.0% deacetylated, Product No. C-M-95-401132, Lot No. 351821, ChitoLytic, Ontario, Canada) at 10 mg/mL was prepared in acetic acid (0.5% v/v). A stock solution of tannin (TAN) (grape seed extract (GSE), TAN'ACTIVE GUT, Batch: 010417, Silvateam, Wilton, CT) at 10 mg/mL was prepared in ethanol. A stock solution of serotonin at 50.0 mg/mL was prepared in water. CHT-TAN composite solutions were prepared as follows: TAN stock solution was added to the CHT stock solution under continuous stirring for 10 min at a weight ratio of 90:10 (CHT:TAN). Then, the serotonin solution was added to the mixture while stirring continuously (yielding 7.00% w/v of the solution). Volume of 30 mL of the CHTL-TAN composite solutions was added to a silicon mold (7.9×5.6×2.5 cm). The samples were placed in an oven at 36° C. for 3 days. See Table

TABLE 8

| | Chitosan Lactate (CHT) | | | Tannin (TAN) | | | Serotonin | | |
|---|---|---|---|---|---|---|---|---|---|
| | Conc. (mg/mL) | Vol. (mL) | Total (mg) | Conc. (mg/mL) | Vol. (mL) | Total (mg) | Conc. (mg/mL) | Vol. (mL) | Total (mg) |
| CHTL:TAN (90:10) 0 mg of Serotonin | 10.0 | 27.0 | 270.0 | 10.0 | 3.0 | 30.0 | 50.0 | 0 | 0 |
| CHTL:TAN (90:10) 22.6 mg of Serotonin | 10.0 | 27.0 | 270.0 | 10.0 | 3.0 | 30.0 | 50.0 | 0.452 | 22.6 |

Chitosan-Tannin (CHT-TAN) Serotonin Film Dissolution

A complete film of approximately 400 mg weight was placed in a beaker containing 100 mL of dd-water and submitted to a slight stirring (100 rpm). At 30, 60, 120, 180, 240, 300, 450, 600, 900, 1200, and 1800 seconds, 500 uL of the dissolution medium was taken and replaced with an equal volume of fresh dd-water. The concentration of Serotonin was determined by HPLC-DAD.

Figure 23:
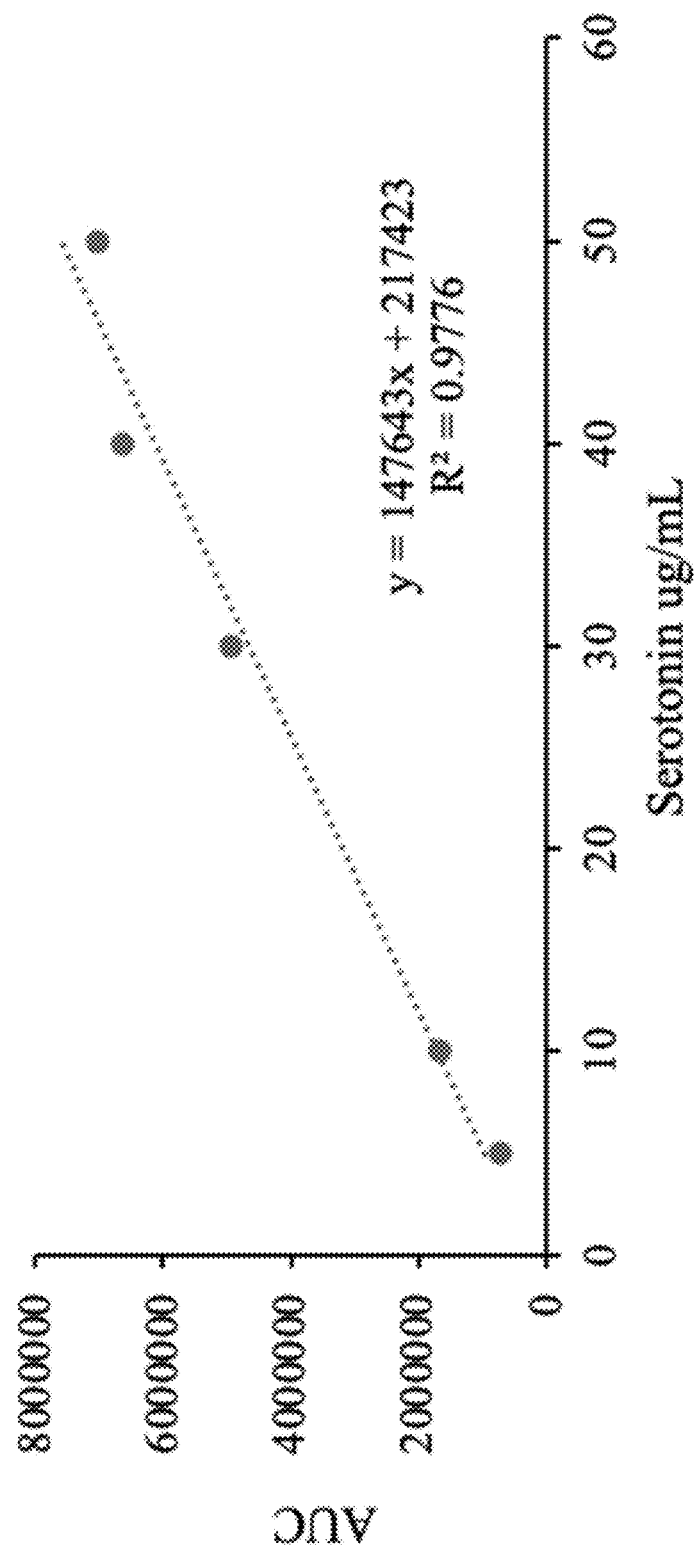
FIG. 23. Standard curve of serotonin.

A standard curve of serotonin in solution is shown in FIG. 23 and Table 9.

TABLE 9

| Serotonin (ug/mL) | AUC |
|---|---|
| 5 | 721300 |
| 10 | 1677639 |
| 30 | 4946028 |
| 40 | 6643911 |
| 50 | 7030060 |

Figure 24A:
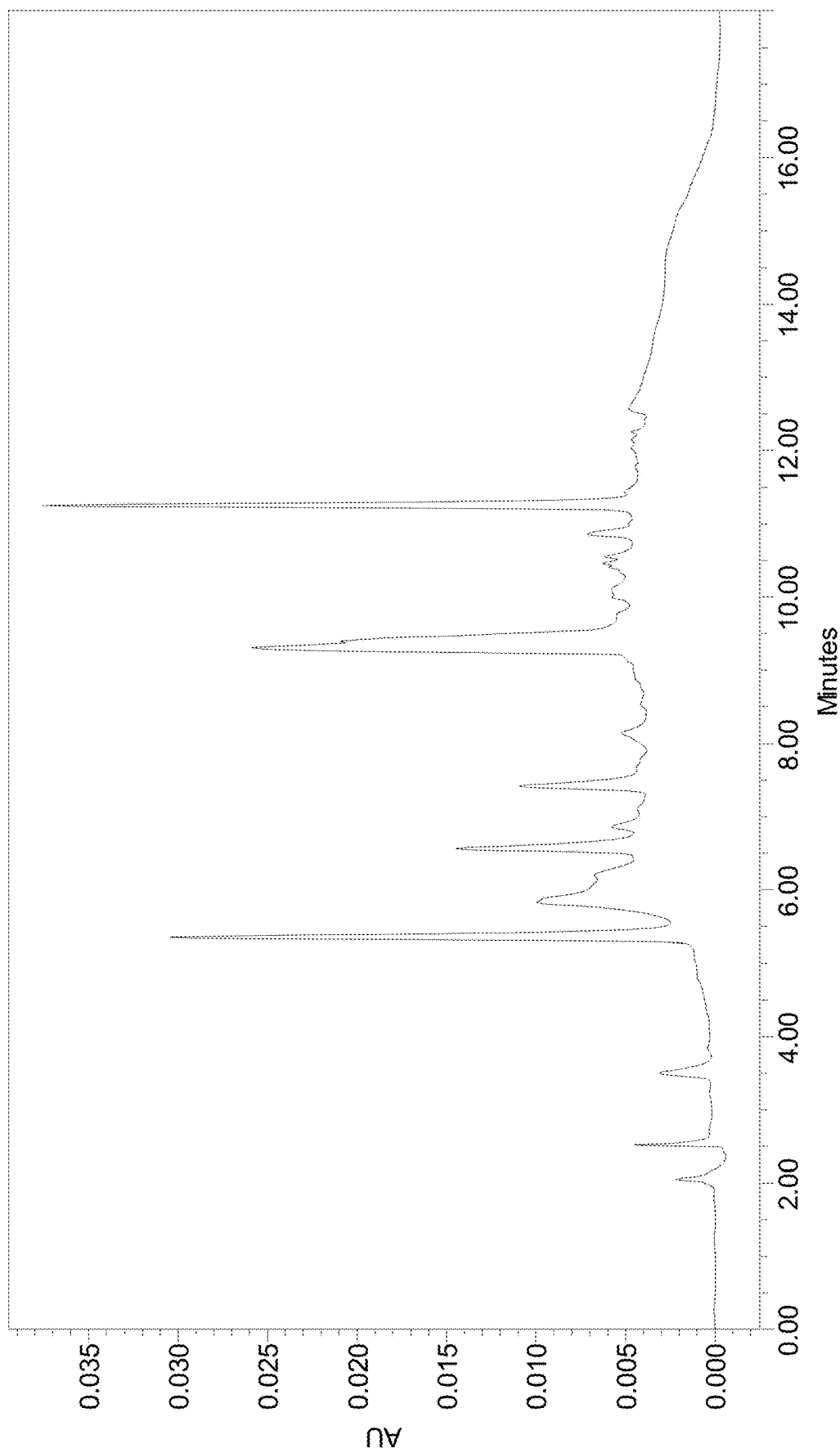
FIG. 24A. HPLC chromatogram of CHTL-TAN (GSE) composite film after dissolution, recorded at 280 nm.
Figure 24B:
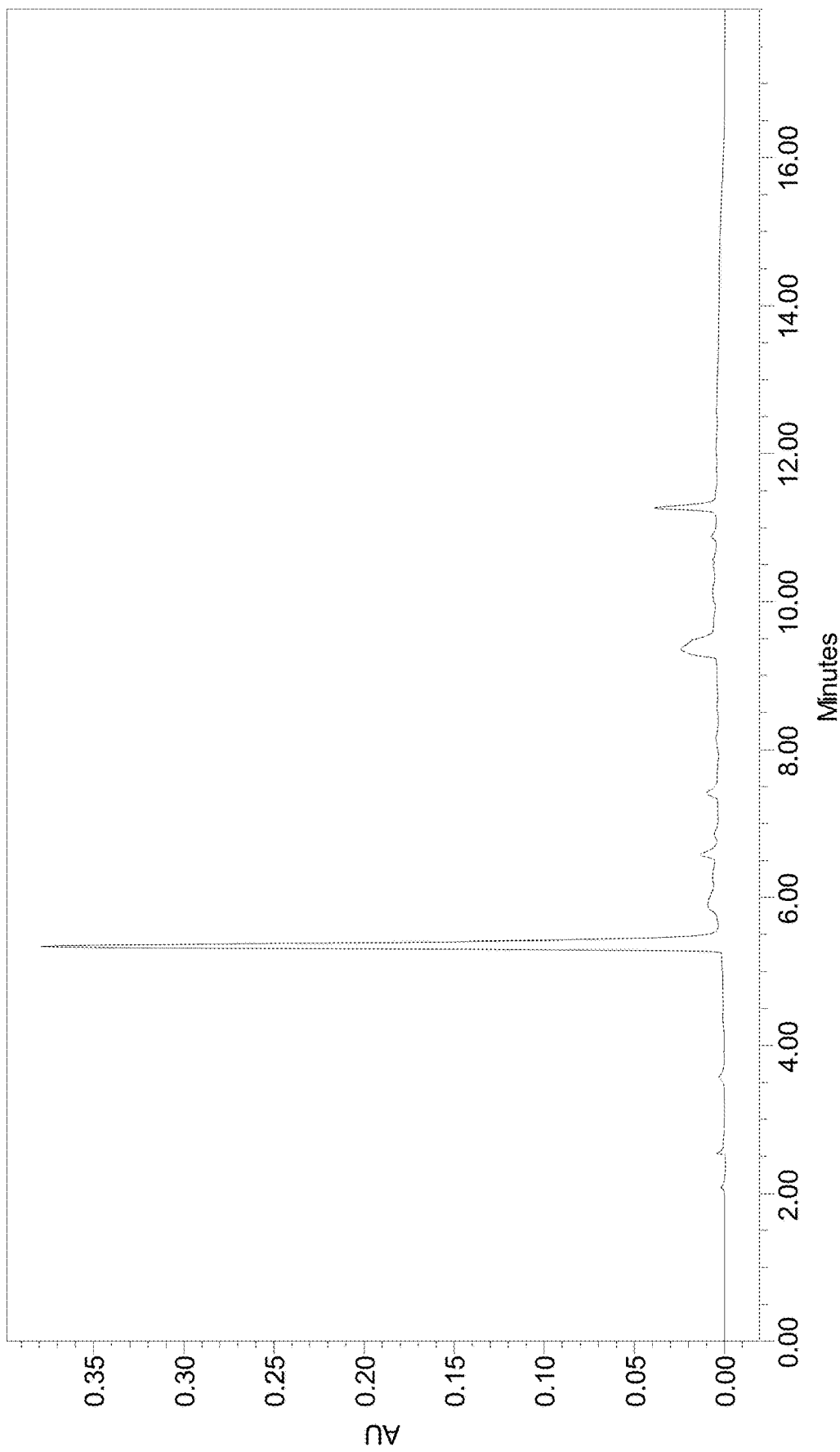
FIG. 24B. HPLC chromatogram of CHT-TAN (GSE) composite film loaded with serotonin after dissolution, recorded at 280 nm.
Figure 25:
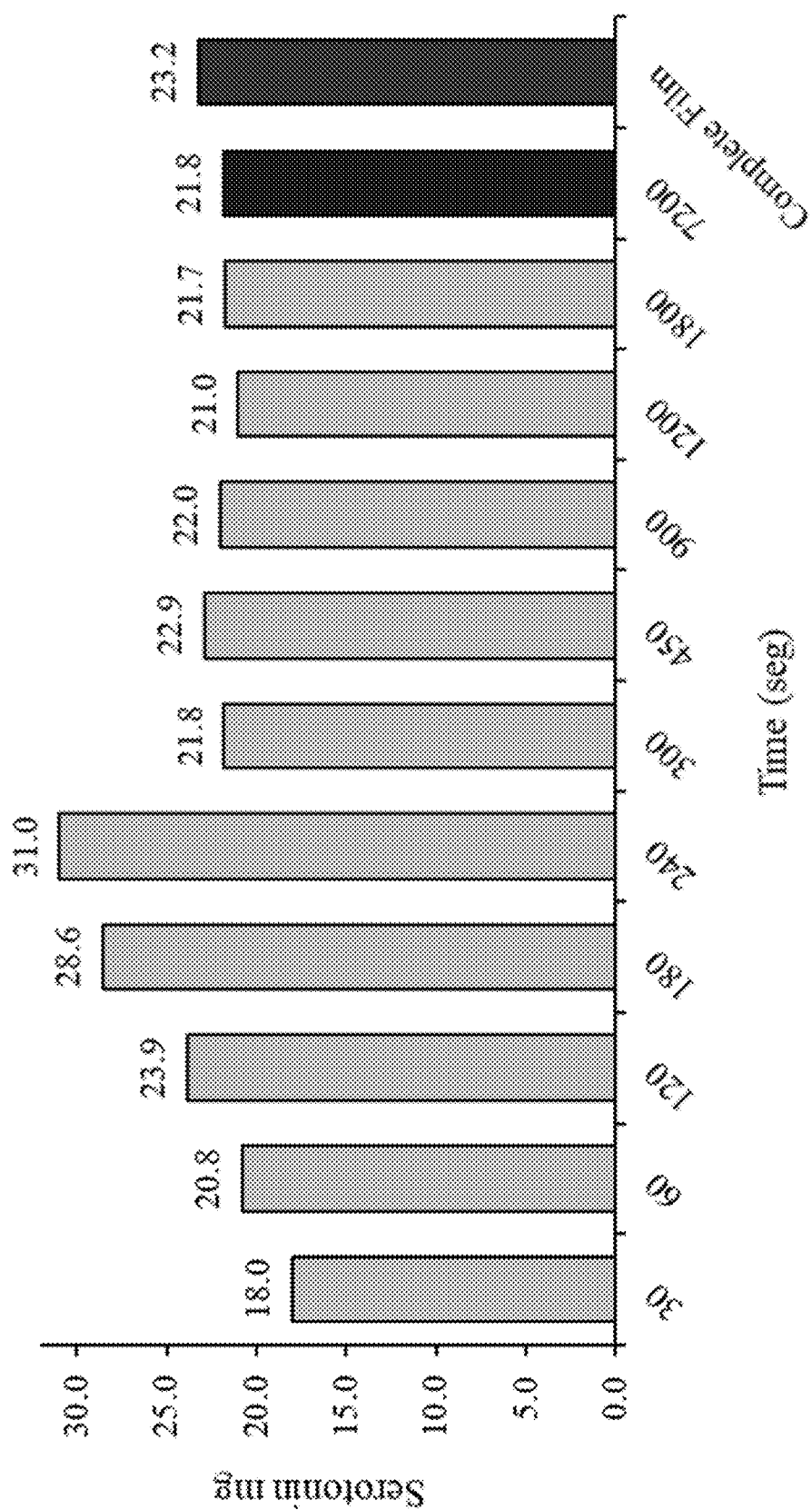
FIG. 25. Serotonin release in mg versus time.
Figure 26:
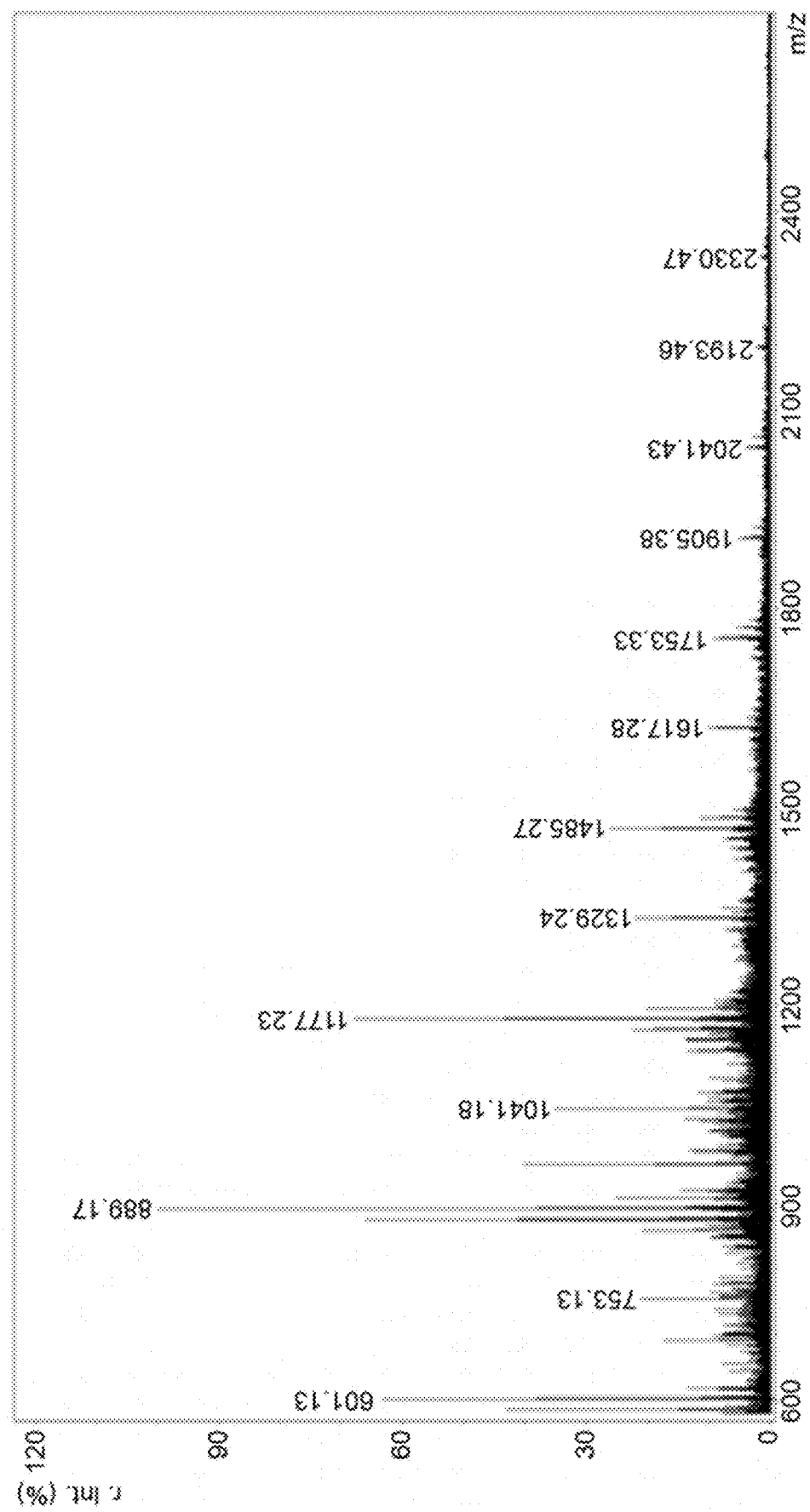
FIG. 26. MALDI-TOF spectra of Tan'Activ GUT gran (Grape seed extract) from SILVA TEAM.

HPLC chromatograms are shown in FIGS. 24A and 24B. The theoretical amount of serotonin loaded into the films were 22.6 mg, and the recovery of serotonin in two samples of dissolved film solutions as determined by HLPC were 21.8 mg (−3.4 percent error) and 23.3 (2.8 percent error). Quantitation of serotonin in solution at each timepoint is shown in FIG. 25.

What is claimed is:

1. A composite composition comprising chitosan lacking lactate moieties, condensed tannin lacking sulfonate moieties, and an active agent, wherein:
   the chitosan lacking lactate moieties has a number average molecular weight of from 125 kDa to 500 kDa;
   the tannin lacking sulfonate moieties has a weight average molecular weight of from 100 Da to 10,000 Da;
   the chitosan lacking lactate moieties and the tannin lacking sulfonate moieties are present in a weight ratio of the chitosan lacking lactate moieties-to-the tannin lacking sulfonate moieties of from 85:15 to 99:1;
   the active agent is selected from the group consisting of serotonin, melatonin, psilocybin, and any combination thereof;
   the active agent is present in the composition in an amount of from 0.001 mg to 500 mg;
   the composition is in a form of a film; and
   the film dissolves in saliva within 4.5 minutes.

2. The composition of claim 1, wherein the composition dissolves in saliva within 2 minutes.

3. A method of administering an active agent to a subject, the method comprising orally administering the composition of claim 1 to the subject.

4. The method of claim 3, wherein the administering comprises oral mucosal administration of the composition to the subject.

5. The method of claim 3, wherein the composition dissolves in a mouth of the subject within 2 minutes.

6. The composition of claim 1, wherein the chitosan lacking lactate moieties has a number average molecular weight of from 200 Da to 350 kDa.

7. The composition of claim 1, wherein the chitosan is a fungal chitosan.

8. The composition of claim 1, wherein the active agent is serotonin.

9. The composition of claim 1, wherein the active agent is melatonin.

10. The composition of claim 1, wherein the active agent is psilocybin.

11. The composition of claim 1, wherein the active agent is present in the composition in an amount of from 0.1 mg to 250 mg.

12. The composition of claim 1, wherein the active agent is present in the composition in an amount of from 0.1 mg to 30 mg.

13. The composition of claim 1, wherein the chitosan lacking lactate moieties and the tannin lacking sulfonate moieties are present in a weight ratio of the chitosan lacking lactate moieties-to-the tannin lacking sulfonate moieties of from 85:15 to 95:5.

14. The composition of claim 13, wherein the chitosan lacking lactate moieties has a number average molecular weight of from 200 Da to 350 kDa.

15. The composition of claim 14, wherein the chitosan is a fungal chitosan.

16. The composition of claim 15, wherein the active agent is serotonin.

17. The composition of claim 15, wherein the active agent is melatonin.

18. The composition of claim 15, wherein the active agent is psilocybin.

19. The composition of claim 15, wherein the active agent is present in the composition in an amount of from 0.1 mg to 250 mg.

20. The composition of claim 15, wherein the active agent is present in the composition in an amount of from 0.1 mg to 250 mg.

* * * * *